(12) United States Patent
Janczewski et al.

(10) Patent No.: US 8,716,420 B2
(45) Date of Patent: May 6, 2014

(54) AMPHIPHILIC POLYMERS AND NANOCRYSTALS COATED THEREWITH

(75) Inventors: Dominik Janczewski, Singapore (SG); Nikodem Tomczak, Singapore (SG); Ming-Yong Han, Singapore (SG); G. Julius Vancso, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 272 days.

(21) Appl. No.: 13/124,113

(22) PCT Filed: Oct. 12, 2009

(86) PCT No.: PCT/SG2009/000374
§ 371 (c)(1),
(2), (4) Date: Aug. 1, 2011

(87) PCT Pub. No.: WO2010/044752
PCT Pub. Date: Apr. 22, 2010

(65) Prior Publication Data
US 2011/0278503 A1 Nov. 17, 2011

Related U.S. Application Data

(60) Provisional application No. 61/104,932, filed on Oct. 13, 2008.

(51) Int. Cl.
C08F 222/06 (2006.01)
C08F 222/14 (2006.01)
C08F 222/22 (2006.01)
C08F 222/20 (2006.01)

(52) U.S. Cl.
USPC ... 526/272; 526/271; 526/318.3; 526/318.41; 526/318.44; 526/318.5

(58) Field of Classification Search
USPC ............ 526/271, 272, 318.3, 318.41, 318.44, 526/318.5
See application file for complete search history.

(56) References Cited

U.S. PATENT DOCUMENTS 3,846,383 A 11/1974 Uyama et al.
4,722,947 A 2/1988 Thanawalla et al.
(Continued)

FOREIGN PATENT DOCUMENTS

JP 57016004 A 1/1982
WO 9623879 A1 8/1996
(Continued)

OTHER PUBLICATIONS

Ariga, K., et al., "Layer-by-layer assembly as a versatile bottom-up nanofabrication technique for exploratory research and realistic . . .", "Phys. Chem. Chem. Phys.", 2007, pp. 2319-2340, vol. 9.

(Continued)

Primary Examiner — Ling Choi
Assistant Examiner — David L Miller
(74) Attorney, Agent, or Firm — Hultquist, PLLC; Steven J. Hultquist; Mary B. Grant

(57) ABSTRACT

An amphiphilic polymer (A) comprising repeat units of the general formulae (I), (II) and (III): or salts thereof, wherein $R^1$ is H or methyl, $R^2$ is an aliphatic moiety with a main chain of 3 to 30 carbon atoms and 0 to 3 heteroatoms selected from the group N, O, S, Se and Si, and $R^3$ is one of (i) an alicyclic moiety with a main chain of 5 to 80 carbon atoms and 0 to 30 heteroatoms (ii) a moiety —Z—$R^4$ wherein $R^4$ is an alicyclic moiety with a main chain of 5 to 80 carbon atoms and 0 to 30 heteroatoms and Z is an aliphatic bridge of 1 to 3 carbon atoms and 0 to 2 heteroatoms, (iii) an aliphatic moiety with a main chain of 3 to 80 carbon atoms and 0 to about 30, and a C≡C group or an azido group.

23 Claims, 18 Drawing Sheets

(56) References Cited

U.S. PATENT DOCUMENTS

| | | | |
|---|---|---|---|
| 5,869,695 | A | 2/1999 | Ulmer et al. |
| 6,316,554 | B1 | 11/2001 | Fridman et al. |
| 2005/0028956 | A1 | 2/2005 | Winslow |
| 2009/0036625 | A1* | 2/2009 | Chang et al. ............. 526/272 |

FOREIGN PATENT DOCUMENTS

| | | |
|---|---|---|
| WO | 0104144 A2 | 1/2001 |
| WO | 03029462 A1 | 4/2003 |
| WO | 2004054923 A1 | 7/2004 |
| WO | 2005019254 A1 | 3/2005 |
| WO | 2005019255 A1 | 3/2005 |
| WO | 2005019256 A2 | 3/2005 |
| WO | 2008121077 A1 | 10/2008 |
| WO | 2009038544 A1 | 3/2009 |

OTHER PUBLICATIONS

Beste, Gerald, et al., "Small antibody-like proteins with prescribed ligand specificities derived from the lipocalin fold", "Proc. Natl. Acad. Sci. USA", Mar. 2, 1999, pp. 1898-1903, vol. 96, No. 5.

Binder, W.H., et al., "Surface-modified nanoparticles via thermal and Cu(I)-mediated click chemistry: Generation of luminescent CdSe . . . ", "J. Mater. Chem.", 2007, pp. 2125-2132, vol. 17.

"Chemical Abstracts No. 106973-21-1", "American Chemical Society", 2009.

"Chemical Abstracts No. 26426-80-2", "American Chemical Society", 2009.

Fernandez-Arguelles, M.T., et al., "Synthesis and Characterization of Polymer-Coated Quantum Dots with Integrated Acceptor Dyes as FRET-Based Nanoprobes", "American Chemical Society", 2007, pp. 2613-2617, vol. 7, No. 9.

Gill, Davinder S. et al., "Biopharmaceutical drug discovery using novel protein scaffolds", "Current Opinion in Biotechnology ", Oct. 19, 2006, pp. 653-658, vol. 17.

Holt, L. et al., "Domain antibodies: proteins for therapy", "Trends in Biotechnology", Nov. 2003, pp. 484-490, vol. 21, No. 11.

Iliades, P. et al., "Triabodies: Single Chain FV Fragments Without a Linker Form Trivalent Trimers", "FEBS Letters", 1997, pp. 437-441, vol. 409.

Janczewski, D., et al., "Designer multi-functional comb-polymers for surface engineering of quantum dots on the nanoscale", "European Polymer Journal", 2009, pp. 3-9, vol. 45.

Kwon, Y., "Quantitative Evaluation of the Relative Cell Permeability of Peptoids and Peptides", "JACS Communications", Jan. 18, 2007, pp. 1508-1509, vol. 129, Publisher: J. Am. Chem. Soc.

Mosavi, Leila K. et al., "The ankyrin repeat as molecular architecture for protein recognition", "Protein Science", 2004, pp. 1435-1448, vol. 13.

Murray, C. B., et al., "Synthesis and characterization of nearly monodisperse CdE (E = S, Se, Te) semiconductor nanocrystallites", "J. Am. Chem. Soc.", 1993, pp. 8706-8715, vol. 115.

Poloukhtine, A. A., et al., "Selective Labeling of Living Cells by a Photo-Triggered Click Reaction", "J. Am. Chem. Soc.", 2009, pp. 15769-15776, vol. 131.

Reed, M.A., "Quantum Dots", "Scientific American", 1993, pp. 118-123.

Rozkiewicz, D.I., et al., "Click Chemistry by Microcontact Printing", "Angew. Chem. Int. Ed.", 2006, pp. 5292-5296, vol. 45.

Silverman, J. et al., "Multivalent avimer proteins eveolved by exon shuffling of a family of human receptor domains", "Nature Biotechnology Letters", Nov. 20, 2005, pp. 1556-1561, vol. 23, No. 12.

Skerra, A., "Engineered protein scaffolds for molecular recognition", "J. Mol. Recognit.", 2000, pp. 167-187, vol. 13.

Stone, E. et al., "The assembly of single domain antibodies into bispecific decavalent molecules", "Journal of Immunological Methods", Nov. 17, 2006, pp. 88-94, vol. 318.

Zhong, Xinhua, et al., "Composition-tunable ZnxCd1-xSe nanocrystals with high luminescence and stability", "J. Am. Chem. Soc.", 2003, pp. 8589-8594, vol. 125.

Zhong, Xinhua, et al., "Alloyed ZnxCd1-xS nanocrystals with highly narrow luminescence spectral width", "J. Am. Chem. Soc.", 2003, pp. 13559-13563, vol. 125.

Janczewski, Dominik, et al., "Designer multi-functional comb-polymers for surface engineering of quantum dots on the nanoscale", "European Polymer Journal", Jan. 2009, pp. 3-9, vol. 45, No. 1 (Abstract Only).

* cited by examiner

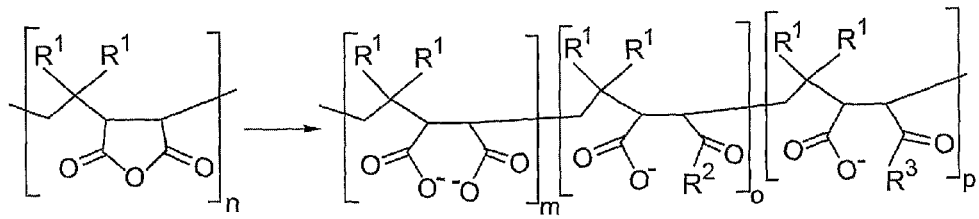
$R^2$ = aliphatic, optionally substituted
Fig. 1
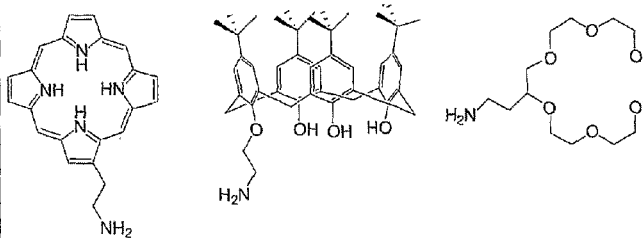

Fig. 1 (continued)

| $R^3H =$ | Application: |
|---|---|
| Various fluorophores, chromophores and dyes e.g.: Coumarin, Rhodamine, Fluoresceine, or any coupled aromatic system, any conductive coupled polymer. 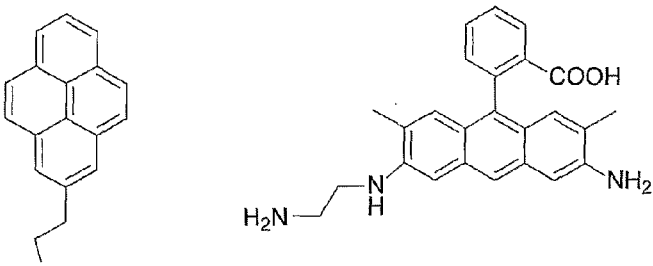 | FRET sensing |
| Various units bearing functions suitable for click chemistry like azide or acetylene e.g.: 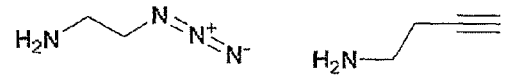 | 2D and 3D structure fabrication, patterning with QDs |

Receptors based on glycolamides
for $Ln^{3+}$ K ~ $10^5$; RH =

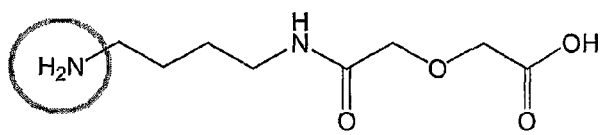

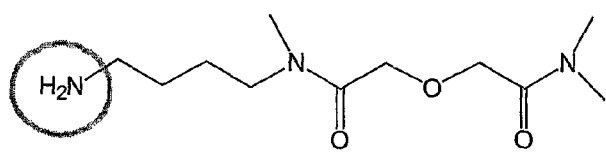

Fig. 2A

Fig. 2C Receptors based on Kryptofix-22 for $Ln^{3+}$ $K \sim 10^{10}$; RH =

= attachment to backbone (cont. on next page)

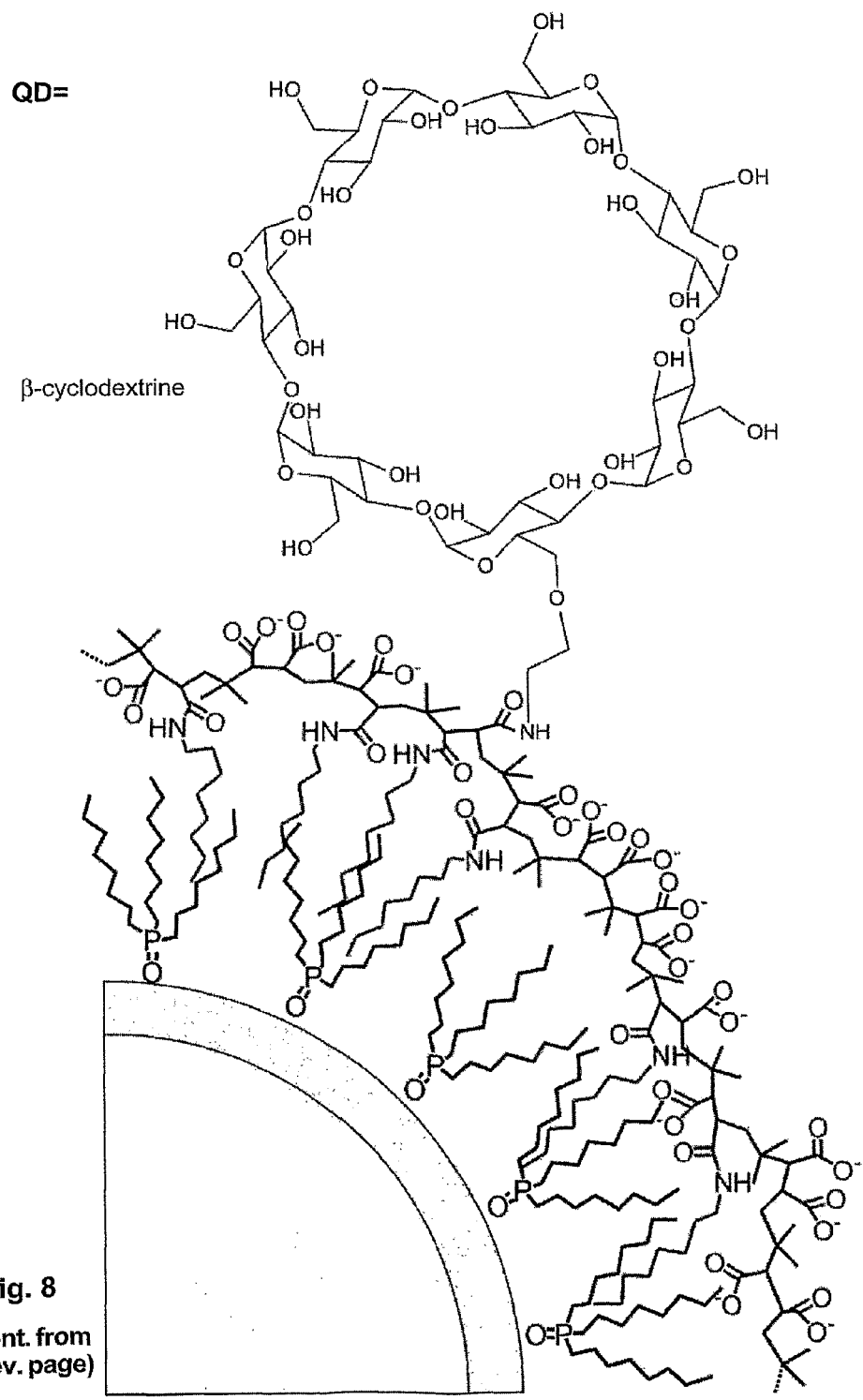
Fig. 8 (cont. from prev. page)

Fig. 11
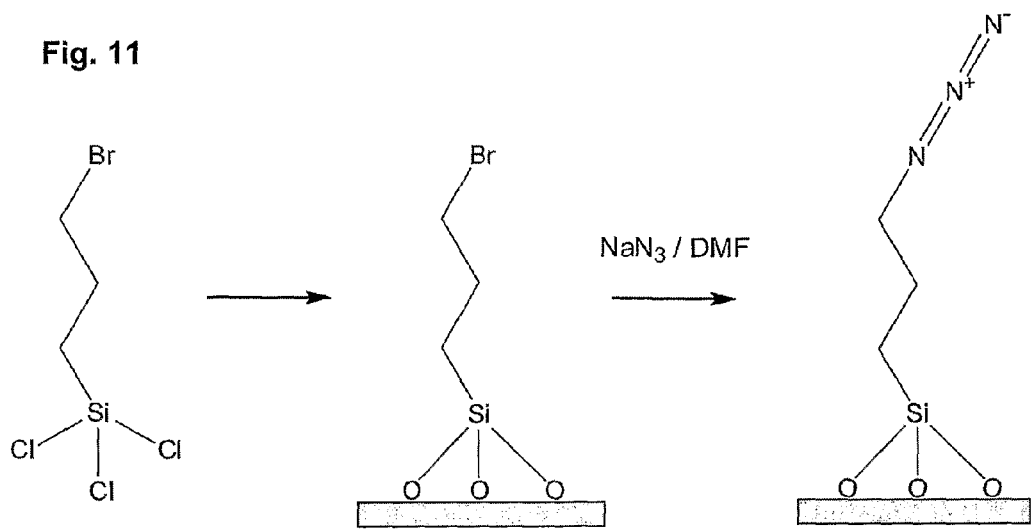
Fig. 12

AMPHIPHILIC POLYMERS AND NANOCRYSTALS COATED THEREWITH

CROSS-REFERENCE TO RELATED APPLICATIONS

This is a U.S. national phase under the provisions of 35 U.S.C. §371 of International Patent Application No. PCT/SG09/00374 filed Oct. 12, 2009, which in turn claims the benefit of priority of an application for "Functional Amphiphilic Polymers-Coated Nanoparticles For 'Click' Chemistry-Based Sensing" filed on Oct. 13, 2008 with the United States Patent and Trademark Office, and there duly assigned U.S. Provisional Patent Application No. 61/104,932. The contents of said U.S. Provisional Patent Application No. 61/104,932 filed on Oct. 13, 2008 are incorporated herein by reference for all purposes, including an incorporation of any element or part of the description, claims or drawings not contained herein and referred to in Rule 20.5(a) of the PCT, pursuant to Rule 4.18 of the PCT. The disclosure of International Patent Application No. PCT/SG09/00374 filed Oct. 12, 2009 is also incorporated herein by reference for all purposes, including an incorporation of any element or part of the description, claims or drawing not contained herein.

FIELD OF THE INVENTION

The present invention relates to novel amphiphilic polymers, in particular amphiphilic polymers suitable for a coating of a nanocrystal. Respective nanocrystals can be used in sensing, 2D and 3D patterning, or a combination thereof.

BACKGROUND OF THE INVENTION

Highly luminescent semiconductor nanocrystals, usually referred to as quantum dots (QDs) with their unique size/composition-tunable narrow emission and broad absorption spectra have drawn great attention in the last decade due to their promising application in optoelectronics and biology. In particular, nanoparticles functionalized with various chemical groups have found many applications in sensing, nanofabrication and biolabeling, among others. For many of these applications the quantum dots have to be soluble in water.

Hydrophobic quantum dots can be solubilised in water either by exchanging hydrophobic TOPO ligands at the quantum dot surface with hydrophilic ligands or by using amphiphilic polymers, which can have both hydrophobic-hydrophobic interaction with hydrophobic ligands on the surface of quantum dots and hydrophilic interaction with water molecules in the medium. The use of amphiphilic polymers has some important advantages over the ligand exchange approach such as the omission of the ligand exchange step and the easy introduction of functionality without affecting the surface of the quantum dots, which could result in deterioration of their optical properties.

Recently, a family of amphiphilic polymers which allows solubilisation and easy functionalization of TOPO-terminated quantum dots has been synthesized and characterized. It allows the transformation of hydrophobic quantum dots into hydrophilic quantum dots for various bio-applications. This family of amphiphilic polymers allows convenient control of the type and number of hydrophobic units in the backbone chain and to optimize polymers to provide water-soluble quantum dots, as well as to easily functionalize the quantum dots without the use of coupling agents. The multi-point hydrophobic attachment of polymers to the hydrophobic layer on quantum dots provides sufficient shell stability in water for an extended period of time without cross-linking.

The amphiphilic polymeric material is synthesized by grafting different side chains with nucleophilic character into a polymeric backbone containing repeating anhydride unit. Upon anhydride ring opening one obtains amphiphilic chain with pendant (both) carboxylic and alkyl chains. As shown in FIG. 1, a series of amphiphilic polymers were synthesised by grafting n-octylamine to poly(isobutylene-alt-maleic anhydride) at different molar ratios. The grafted alkyl chains (like for example n-octylamine chain) have hydrophobic character and serve as anchoring points for attachment to the TOPO terminated quantum dot surface.

There is, however, still a need for more sophisticated water-soluble nano-particles or nanoparticle composites, in particular for use in sensing or nanofabrication.

Accordingly it is an object of the present invention to provide water-soluble nanoparticles that are suitable for sensing and/or immobilization, ideally including 2D and 3D patterning. This object is solved by providing an amphiphilic polymer according to claim 1.

SUMMARY OF THE INVENTION

In a first aspect the present invention provides an amphiphilic polymer (A) that includes repeat units of the general formulae (I), (II) and (III) or salts thereof:

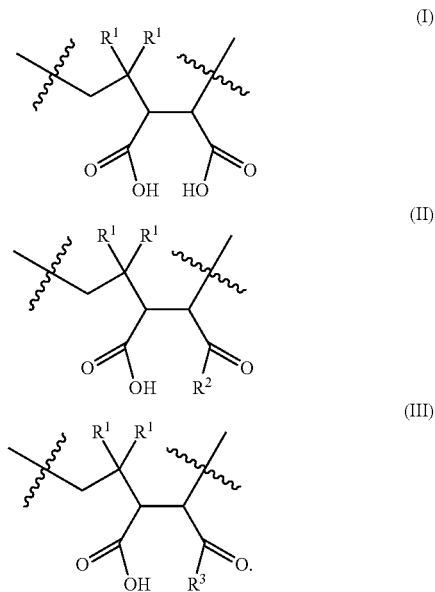

The repeat unit of general formula (I) is included in the amphiphilic polymer with a number of m units, while the repeat unit of general formula (II) is included in the amphiphilic polymer with a number of o units and repeat unit of general formula (III) is included in the amphiphilic polymer with a number of p units. Each of m, o and p is an independently selected integer from about 3 to about 400. The sum of m+o+p is selected to be in the range from about 10 to about 10000. $R^1$ in repeat units (I)-(III) is one of H and methyl. $R^2$ in repeat unit (II) is an aliphatic moiety, which has a main chain of about 3 to about 30 carbon atoms and 0 to about 3 heteroatoms. A respective heteroatom may be one of N, O, S, Se and Si. $R^3$ in repeat unit (III) is one of (i) an alicyclic moiety, a moiety —Z—$R^4$ and (iii) an aliphatic moiety. Where $R^3$ is (i) an alicyclic moiety it has a main chain of about 5 to about 80 carbon atoms and 0 to about 30 heteroatoms. A respective heteroatom may be one of N, O, S, Se and Si. Where $R^3$ is (ii) a moiety —Z—$R^4$, $R^4$ is an alicyclic moiety with a main chain of about 5 to about 80 carbon atoms and 0 to about 30 heteroatoms. A respective heteroatom may be one of N, O, S, Se and Si. Z is an aliphatic bridge with a main chain of 1 to about 3 carbon atoms and 0 to about 2 heteroatoms. A respective heteroatom may be one of N, O, S, Se and Si. Where $R^3$ is (iii) an aliphatic moiety, it has a main chain of about 3 to about 80 carbon atoms and 0 to about 30 heteroatoms. A respective heteroatom may be one of N, O, S, Se and Si. Where $R^3$ is an aliphatic moiety, it further has a C≡C group or an azido group.

In some embodiments the amphiphilic polymer (A) further comprises a repeat unit of the general formula (IV):

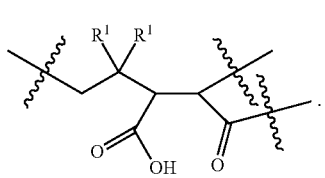

(IV)

To distinguish an amphiphilic polymer that include a repeat unit of formula (IV) from other embodiments, such a polymer will in the following be denoted (B). The repeat unit of general formula (IV) is in such embodiments included in the amphiphilic polymer with a number of r units. R is an integer independently selected in the range from 1 to about 400. The sum of p+r is selected in the range from about 3 to about 400. $R^1$ in repeat unit (IV) is one of H and methyl. The unit (IV) of the polymer is covalently coupled further matter, which is one of a surface, a further amphiphilic polymer (B'), and a sensing molecule. It is coupled to such matter via a bridge that includes an aliphatic moiety and a triazole ring. The aliphatic moiety has a main chain of about 3 to about 80 carbon atoms and 0 to about 20 heteroatoms. The bridge is typically obtained by the reaction of the C≡C group or the azido group of the aliphatic moiety $R^3$ with a C≡C group or an azido group, respectively, on further matter, e.g. the surface, the further polymer or the sensing molecule.

A respective sensing molecule may for instance be one of a peptide, a protein, a nucleic acid, a saccharide, a polysaccharide, and a lipid. The further amphiphilic polymer (B') may be a polymer to which the above definition of the polymer (B) of these embodiments applies. However, moieties $R^1$, $R^2$, and $R^4$, as well as the numbers of the units present, i.e. m, o, p and r, are selected independently from those moieties and integers selected for the polymer (B).

In a second aspect the present invention provides a water-soluble nanocrystal. The water-soluble nanocrystal includes on its surface via non-covalent or covalent interaction an amphiphilic polymer according to the first aspect.

In a third aspect the present invention provides a plurality of water-soluble nanocrystals. A nanocrystal of the plurality of water-soluble nanocrystals include on their surface via non-covalent or covalent interaction an amphiphilic polymer (B) (supra). This amphiphilic polymer (B) includes repeat units of the general formulae (I), (II), (III) and (IV) or salts thereof:

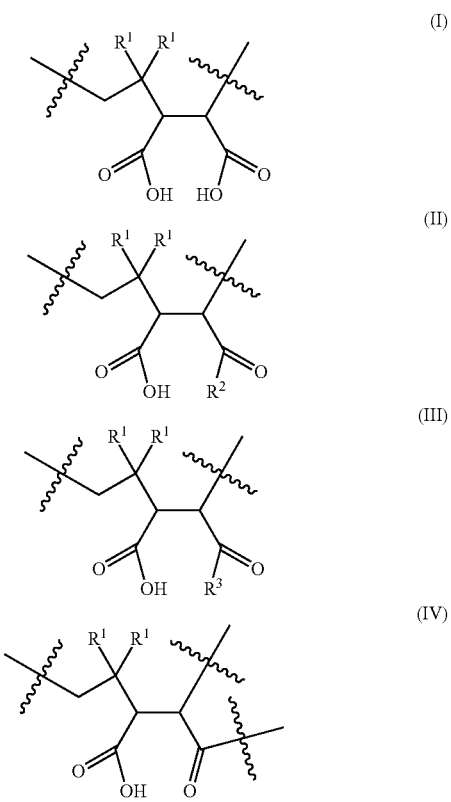

The repeat unit of general formula (I) is included in the amphiphilic polymer with a number of m units. The repeat unit of general formula (II) is included in the amphiphilic polymer with a number of o units. The repeat unit of general formula (III) is included in the amphiphilic polymer with a number of p units. The repeat unit of general formula (IV) is included in the amphiphilic polymer with a number of r units. Each of m, o, p, and r is an integer independently selected from one another. Each integer of m, o and p is selected in the range from about 3 to about 400. The integer of r is an independently selected even integer, which is selected in the range from 1 to about 400. The selection is taken such that the sum of p+r is in the range from about 3 to about 400. The sum of m+o+p+r is selected in the range from about 10 to about 10000. $R^1$ in repeat units (I)-(IV) is H or methyl. $R^2$ in repeat unit (II) is an aliphatic moiety. This aliphatic moiety defining $R^2$ has main chain of about 3 to about 30 carbon atoms and 0 to about 3 heteroatoms. A respective heteroatom may be one of N, O, S, Se and Si. $R^3$ in repeat unit (III) is an aliphatic moiety. This aliphatic moiety defining $R^3$ has a main chain of about 3 to about 80 carbon atoms. The aliphatic moiety defining $R^3$ further has a C≡C group or an azido group. Two water-soluble nanocrystals of the plurality of nanocrystals are coupled via a bridge D. The bridge D is covalently bonded to a unit (IV) of a polymer (B) that is included on the surface of a first nanocrystal. It is also covalently bonded to a unit (IV) of a polymer (B) that is included on the surface of a second nanocrystal. Accordingly, the bridge covalently links the amphiphilic polymer (B) of the first nanocrystal and amphiphilic polymer (B) of the second nanocrystal, thereby coupling the two nanocrystals. The bridge D is of the structure —Y—$R^5$—Y'—. $R^5$ of this bridge D is an arylaliphatic or arylalicyclic bridge. This arylaliphatic or arylalicyclic bridge includes a triazole ring. Y and Y' of this bridge D are each independently selected an aliphatic bridge with a main chain of 1 to about 80 carbon atoms and 0 to about 20 heteroatoms. A respective heteroatom may be one of N, O, S, Se and Si. In some embodiments the bridge D is of the structure —Y—$R^5$—Y'—. Y' of this bridge D is, as Y, an aliphatic bridge with a main chain of 1 to about 80 carbon atoms and 0 to about 20 heteroatoms. Y' is independently selected from the bridge Y.

In a fourth aspect the present invention provides a plurality of water-soluble nanocrystals immobilized on a surface. The nanocrystals of the plurality of nanocrystals include on their surface via non-covalent or covalent interaction an amphiphilic polymer (B). The amphiphilic polymer (B) includes repeat units as defined in terms of the third aspect. These repeat units are accordingly of the general formulae (I), (II), (III) and (IV) or salts thereof:

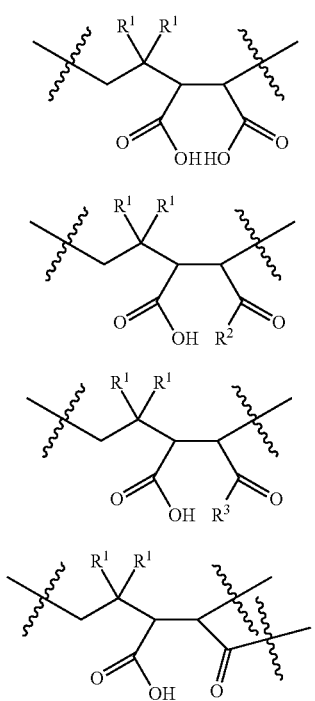

The repeat unit of general formula (I) is included in the amphiphilic polymer with a number of m units. The repeat unit of general formula (II) is included in the amphiphilic polymer with a number of o units. The repeat unit of general formula (III) is included in the amphiphilic polymer with a number of p units. The repeat unit of general formula (IV) is included in the amphiphilic polymer with a number of r units. Each of m, o, p, and r is an integer independently selected from one another. Each integer of m, o and p is selected in the range from about 3 to about 400. The integer of r is an independently selected even integer, which is selected in the range from 1 to about 400. The selection is taken such that the sum of p+r is in the range from about 3 to about 400. The sum of m+o+p+r is selected in the range from about 10 to about 10000. $R^1$ in repeat units (I)-(IV) is H or methyl. $R^2$ in repeat unit (II) is an aliphatic moiety. This aliphatic moiety defining $R^2$ has main chain of about 3 to about 30 carbon atoms and 0 to about 3 heteroatoms. A respective heteroatom may be one of N, O, S, Se and Si. $R^3$ in repeat unit (III) is an aliphatic moiety. This aliphatic moiety defining $R^3$ has a main chain of about 3 to about 80 carbon atoms. The aliphatic moiety defining $R^3$ further has a C≡C group or an azido group. The nanocrystals of the plurality of nanocrystals are coupled to the surface via a bridge D. The bridge D is covalently bonded to a unit (IV) of a the polymer B, which is included on the surface of the nanocrystal, and to the surface. The bridge D is of the structure -$G^1$-$R^5$-$G^2$-. $G^1$ and $G^2$ of the bridge D are independent from one another an aliphatic bridge of 1 to about 80 carbon atoms and 0 to about 20 heteroatoms. A respective heteroatom may be one of N, O, S, Se and Si. $R^5$ is an arylaliphatic or arylalicyclic bridge that includes a triazole ring. The bridge D is obtained by a reaction involving the C≡C group or the azido group of the aliphatic moiety $R^3$ and a C≡C group or an azido group on the surface.

In a fifth aspect the present invention provides a process of forming an amphiphilic polymer (A) according to the first aspect. The process includes providing a maleic anhydride polymer of general formula (V):

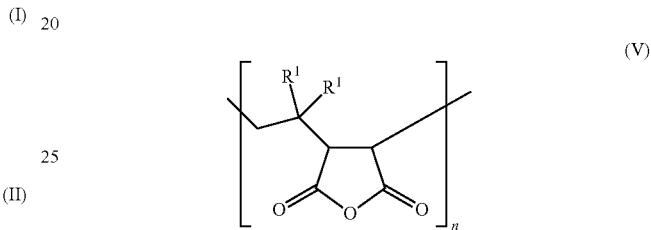

In general formula (V) n is an integer from about 10 to about 10000. $R^1$ in general formula (V) is H or methyl. The process further includes reacting the maleic anhydride polymer of general formula (V) in a suitable solvent with a first compound and with a second compound. The first compound is a monofunctional aliphatic compound. This monofunctional aliphatic compound carries a functional group. The functional group is capable of forming a linkage with an anhydride. The first compound, being a monofunctional aliphatic compound, has an alkyl chain of about 3 to about 20 carbon atoms and 0 to about 2 heteroatoms. A respective heteroatom may be one of N, O, S, Se and Si. The second compound is an alicyclic or aliphatic compound that carries a functional group. The functional group is capable of forming a linkage with an anhydride. Where the second compound is an alicyclic compound, it has a main chain of about 5 to about 80 carbon atoms and 0 to about 30 heteroatoms selected from the group N, O, S, Se and Si. Where the second compound is an aliphatic compound, it is either (i) an aliphatic bridge having 1 to about 3 carbon atoms substituted with an alicyclic moiety or (ii) has a main chain of about 3 to about 80 carbon atoms and 0 to about 20 hetero-atoms. Where the aliphatic compound is an aliphatic bridge, its main chain may further have 0 to about 2 heteroatoms. A respective heteroatom may in both cases be one of N, O, S, Se and Si. The alicyclic moiety with which the aliphatic compound is substituted is a moiety $R^4$. The alicyclic moiety $R^4$ typically has a main chain of about 5 to about 80 carbon atoms and 0 to about 30 heteroatoms. A respective heteroatom may be one of N, O, S, Se and Si. Where the aliphatic compound has a main chain of about 3 to about 80 carbon atoms (and 0 to about 20 heteroatoms, supra) it carries, in addition to the functional group that is capable of forming a linkage with an anhydride, a C≡C group or an azido group.

In a sixth aspect the present invention provides a method of forming a water-soluble nanocrystal. The method includes providing a nanocrystal in a suitable solvent. The method further includes contacting the nanocrystal with an amphiphilic polymer (A) according to the first aspect. The method also includes allowing non-covalent or covalent interaction between the amphiphilic polymer and the nanocrystal to occur. Thereby a water-soluble nanocrystal is formed.

In a seventh aspect the present invention provides the use of a plurality of water-soluble nanocrystals according to the third aspect. The plurality of water-soluble nanocrystals is used to covalently cover a surface with the nanocrystals. The water-soluble nanocrystals used have an amphiphilic polymer with a repeat unit (III), in which $R^3$ is an aliphatic moiety with a main chain of about 3 to about 80 carbon atoms and a C≡C group or an azido group (cf. above). In some embodiments a plurality of azido groups or C≡C groups may be immobilized on the surface. Thereby anchorage sites are provided, which are capable of undergoing a reaction with the C≡C groups or the azido groups, respectively, of the water-soluble nanocrystals.

In this regard the invention also provides a method of covalently covering a surface with a plurality of water-soluble nanocrystals according to the third aspect. The method includes immobilizing a plurality of azido groups or C≡C groups on the surface. The method further includes providing a plurality of water-soluble nanocrystals. The nanocrystals of this plurality of nanocrystals have an amphiphilic polymer with a repeat unit (III), in which $R^3$ is an aliphatic moiety with a main chain of about 3 to about 80 carbon atoms and a C≡C group or an azido group (cf. above), respectively. Where a plurality of azido groups is immobilized on the surface, $R^3$ of the amphiphilic polymer is an aliphatic moiety that has a C≡C group. Where a plurality of C≡C groups is immobilized on the surface, $R^3$ of the amphiphilic polymer is an aliphatic moiety that has an azido group. The method further includes contacting the surface, on which the plurality of azido groups or C≡C groups is immobilized, with the water-soluble nanocrystals.

In an eighth aspect the present invention provides the use of a water-soluble nanocrystal according to the second aspect for detection purposes. The nanocrystal is in particular used in the detection of one of an ion, a peptide, a protein, a nucleic acid, a saccharide, a polysaccharide, a cell and a virus.

BRIEF DESCRIPTION OF THE DRAWINGS

The invention will be better understood with reference to the detailed description when considered in conjunction with the non-limiting examples and the accompanying drawings.

FIG. 1 depicts a general scheme of the formation and the overall structure of polymers that has previously been used in the coating of quantum dots (cf. WO2009/038544), and that is also underlying the compounds of the present invention. The present invention provides novel moieties that can be used as "$R^3$" and confers new properties to the respective polymers, allowing their use in new applications. Exemplary effects and applicability of side chains $R^3$ of a corresponding polymer with a corresponding polymer immobilized thereon are also shown.

FIG. 11 shows a glass or silicon oxide surface (1) functionalization with azide functional groups.

FIG. 12 is a confocal fluorescent microscope image of glass slide surface covered with functionalized quantum dots.

DETAILED DESCRIPTION OF THE INVENTION

Figure 2B:
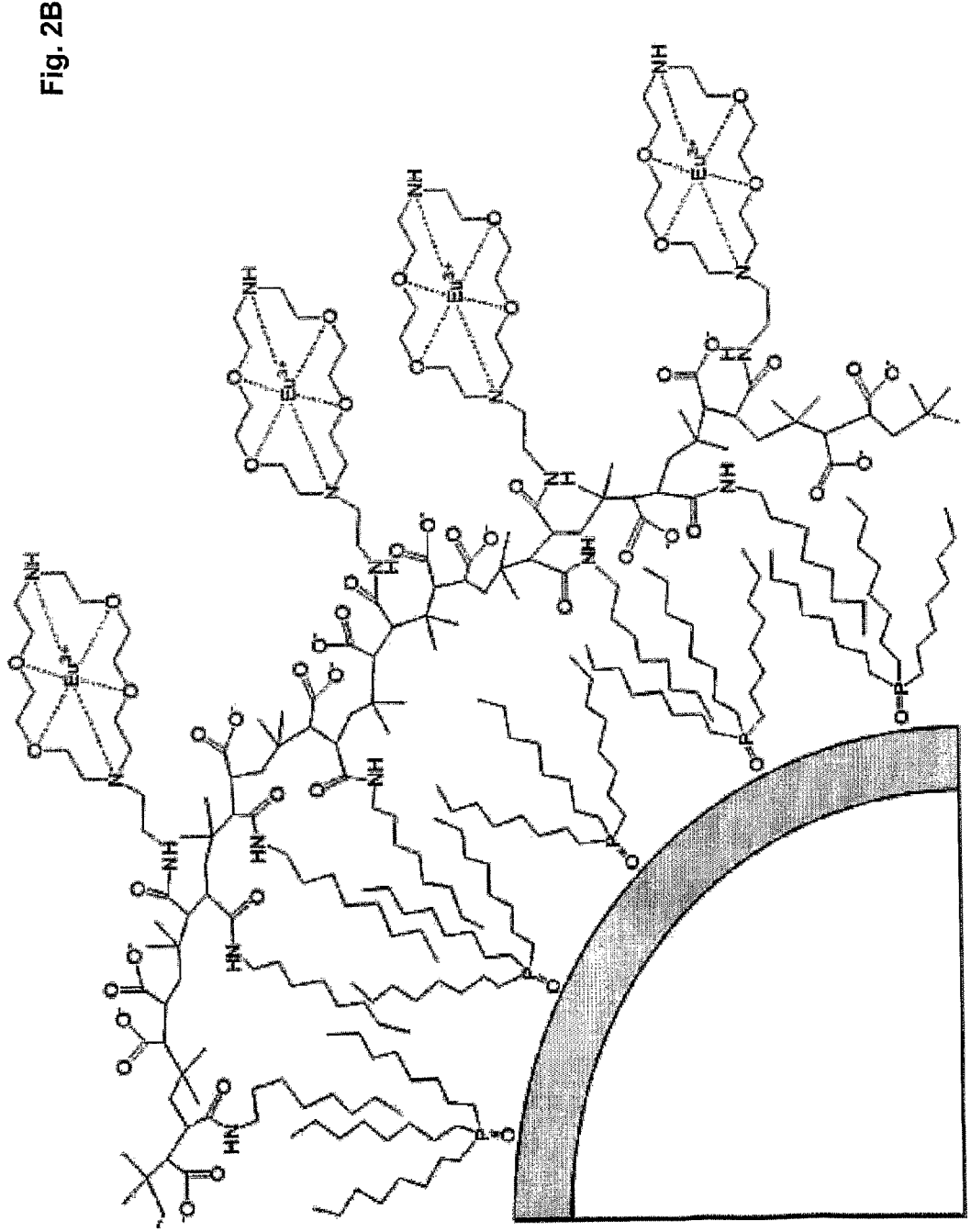
FIG. 2 depicts examples of moieties included in the polymers that render quantum dots equipped therewith suitable for sensing applications. A: receptor moieties based on glycolamides; B, C: receptor moieties based on Kryptofix-22, in FIG. 2B depicted in the form immobilized on a quantum dot. The Kryptofix receptor moiety grafted onto the polymeric shell allows for sensing of Lanthanide ions, like $Eu^{3+}$ or $Gd^{3+}$, or sensing anions by time-resolved FRET (fluorescence resonance energy transfer).
Figure 3:
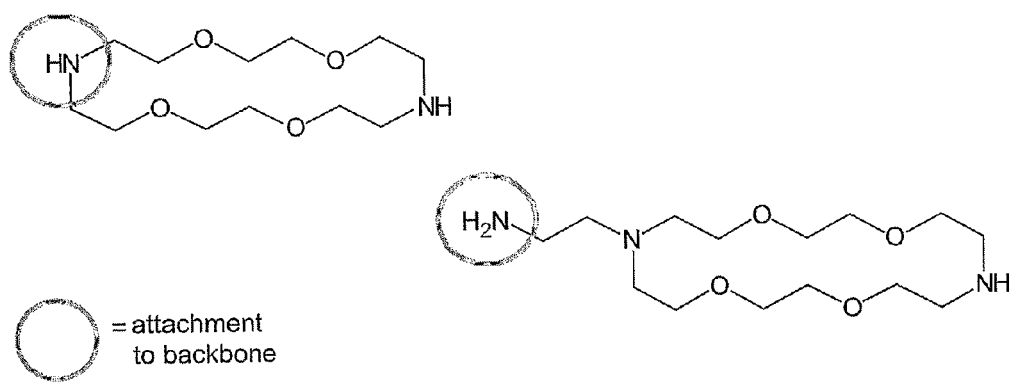
FIG. 3 depicts schematically the synthesis of a polymer functionalized with a Kryptofix-22 receptor moiety.
Figure 3:
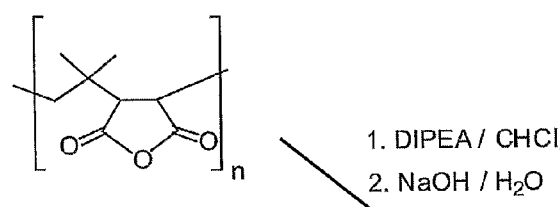
Figure 3:
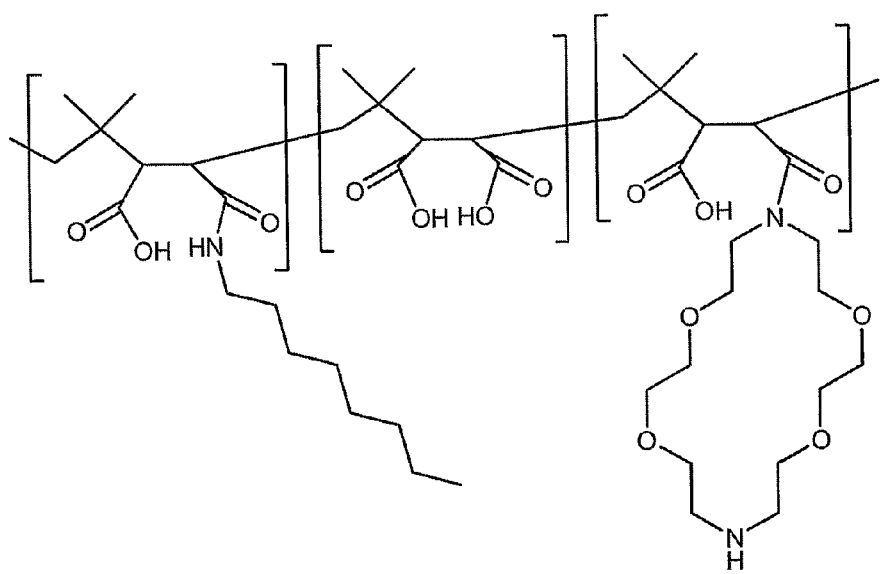
Figure 4:
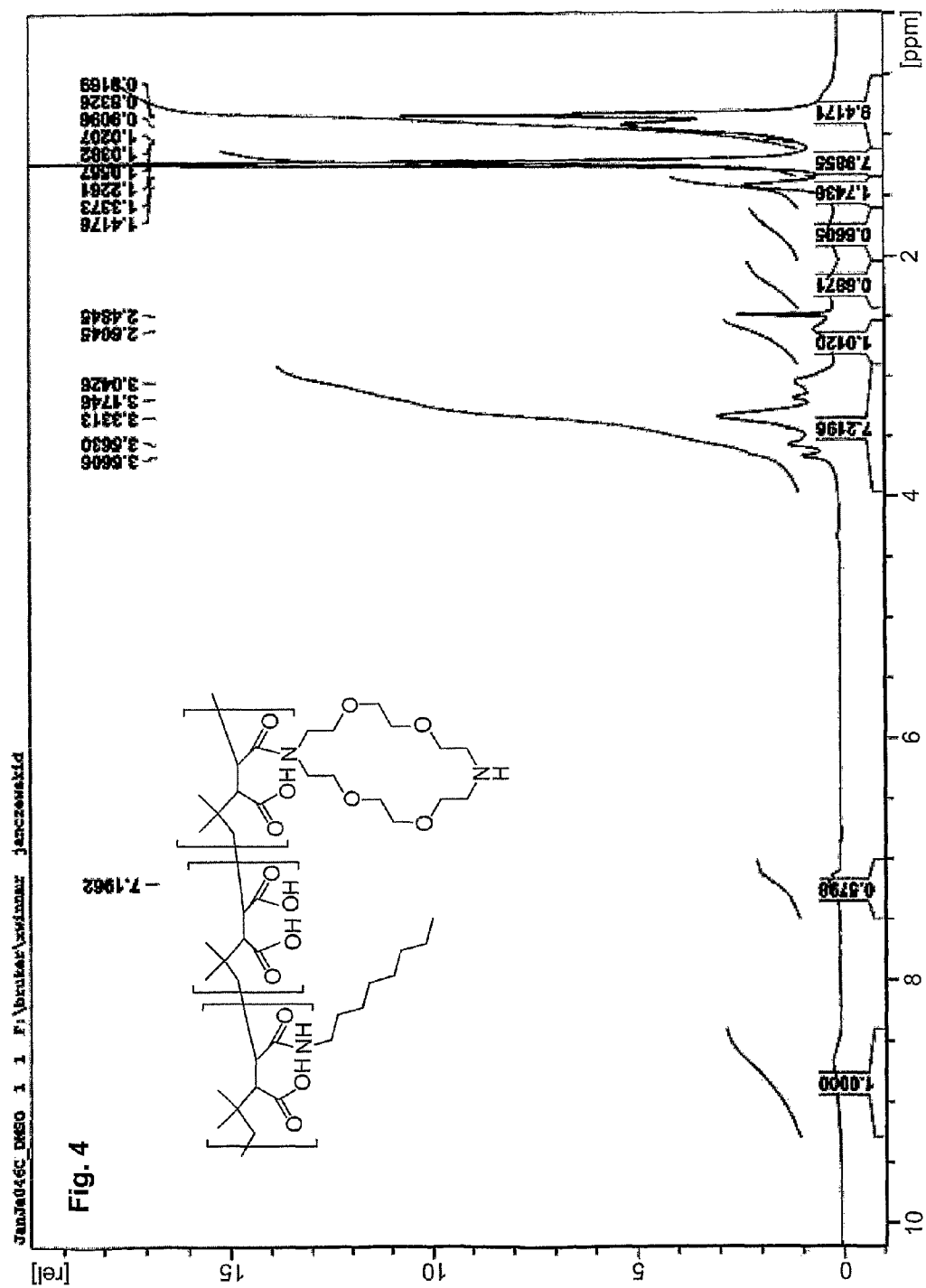
FIG. 4 depicts a $^1H$ NMR spectrum of a polymer with a Kryptofix-22 moiety wherein the ratio of the three units depicted in FIG. 1 and FIG. 3 (free acid/moiety attached to polymer backbone), i.e. m/o/p in FIG. 1 is 17/6.37/1, or 69.9%/26.1%/4.1%.

The present invention relates inter alia to an amphiphilic polymer as well as to a process of the formation of such a polymer. It also relates to an amphiphilic particle coating. The term amphiphilic refers to a polymer that is soluble in both polar and non-polar fluids. It also encompasses multiphase polymers albeit a polymer according to the invention is typically used in only one phase and may be employed to solubilise matter in a desired phase, including to stabilize a phase interface and for phase-transfer purposes. The amphiphilic properties of the polymer are due to the presence of both polar and non-polar moieties within the same polymer. In this regard the polymer may be of surfactant nature. Accordingly, the polar properties of a polymer according to the invention are based on polar moieties. One such moiety are —COOH side groups, in particular in the form of charged COO⁻ groups, that the hydrocarbon backbone of the polymer carries. Generally, a surfactant molecule includes a polar, typically hydrophilic, headgroup attached to a non-polar, typically hydrocarbon, moiety. Non-polar moieties of the polymer include the hydrocarbon backbone as well as aliphatic moieties that the hydrocarbon backbone carries The term "aliphatic" means, unless otherwise stated, a straight or branched hydrocarbon chain, which may be saturated, i.e. alkyl or alkylene, or mono- or poly-unsaturated and include heteroatoms (see above). An unsaturated aliphatic group contains one or more double and/or triple bonds (alkenyl or alkynyl moieties). The branches of the hydrocarbon chain may include linear chains as well as non-aromatic cyclic elements. The (main) chain of an aliphatic moiety (including bridge), may, unless otherwise stated, be of any length, and contain any number of branches. Typically, the hydrocarbon (main) chain includes 1 to about 5, to about 10, to about 15, to about 20, to about 30 or to about 40 carbon atoms. Examples of alkenyl radicals are straight-chain or branched hydrocarbon radicals which contain one or more double bonds. Alkenyl radicals normally contain about two to about twenty carbon atoms and one or more, for instance two, double bonds, such as about two to about ten carbon atoms, and one double bond. Alkynyl radicals normally contain about two to about twenty carbon atoms and one or more, for example two, triple bonds, such as two to ten carbon atoms, and one triple bond. Examples of alkynyl radicals are straight-chain or branched hydrocarbon radicals which contain one or more triple bonds. Examples of alkyl groups are methyl, ethyl, propyl, butyl, pentyl, hexyl, heptyl, octyl, nonyl, decyl, the n isomers of these radicals, isopropyl, isobutyl, isopentyl, neopentyl, sec.-butyl, tert.-butyl, neopentyl and 3,3-dimethylbutyl. Both the main chain as well as the branches may furthermore contain heteroatoms as for instance N, O, S, Se or Si or carbon atoms may be replaced by these heteroatoms.

The term "alicyclic" may also be referred to as "cycloaliphatic" and means, unless stated otherwise, a non-aromatic cyclic moiety (e.g. hydrocarbon moiety), which may be saturated or mono- or poly-unsaturated. The cyclic hydrocarbon moiety may also include fused cyclic ring systems such as decalin and may also be substituted with non-aromatic cyclic as well as chain elements. The main chain of the cyclic hydrocarbon moiety may, unless otherwise stated, be of any length and contain any number of non-aromatic cyclic and chain elements. Typically, the hydrocarbon (main) chain includes 3, 4, 5, 6, 7 or 8 main chain atoms in one cycle. Examples of such moieties include, but are not limited to, cyclopentyl, cyclohexyl, cycloheptyl, or cyclooctyl. Both the cyclic hydrocarbon moiety and, if present, any cyclic and chain substituents may furthermore contain heteroatoms, as for instance N, O, S, Se or Si, or a carbon atom may be replaced by these heteroatoms. The term "alicyclic" also includes cycloalkenyl moieties that are unsaturated cyclic hydrocarbons, which generally contain about three to about eight ring carbon atoms, for example five or six ring carbon atoms. Cycloalkenyl radicals typically have a double bond in the respective ring system. Cycloalkenyl radicals may in turn be substituted. Examples of such moieties include, but are not limited to, cyclohexenyl, cyclooctenyl or cyclodecenyl.

In contrast thereto, the term "aromatic" means an at least essentially planar cyclic hydrocarbon moiety of conjugated double bonds, which may be a single ring or include multiple condensed (fused) or covalently linked rings, for example, 2, 3 or 4 fused rings. The term aromatic also includes alkylaryl. Typically, the hydrocarbon (main) chain includes 5, 6, 7 or 8 main chain atoms in one cycle. Examples of such moieties include, but are not limited to, cyclopentadienyl, phenyl, napthalenyl-, [10]annulenyl-(1,3,5,7,9-cyclodecapentaenyl-), [12]annulenyl-, [8]annulenyl-, phenalene (perinaphthene), 1,9-dihydropyrene, chrysene (1,2-benzophenanthrene). An example of an alkylaryl moiety is benzyl. The main chain of the cyclic hydrocarbon moiety may, unless otherwise stated, be of any length and contain any number of heteroatoms, as for instance N, O and S. Such a heteroaromatic moiety may for example be a 5- to 7-membered unsaturated heterocycle which has one or more heteroatoms from the series O, N, S. Examples of such heteroaromatic moieties (which are known to the person skilled in the art) include, but are not limited to, furanyl-, thiophenyl-, naphtyl-, naphthofuranyl-, anthrathiophenyl-, pyridinyl-, pyrrolyl-, quinolinyl, naphthoquinolinyl-, quinoxalinyl-, indolyl-, benzindolyl-, imidazolyl-, oxazolyl-, oxoninyl-, oxepinyl-, benzoxepinyl-, azepinyl-, thiepinyl-, selenepinyl-, thioninyl-, azecinyl-, (azacyclodecapentaenyl-), diazecinyl-, azacyclododeca-1,3, 5,7,9,11-hexaene-5,9-diyl-, azozinyl-, diazocinyl-, benzazocinyl-, azecinyl-, azaundecinyl-, thia[11]annulenyl-, oxacyclotrideca-2,4,6,8,10,12-hexaenyl- or triazaanthracenyl-moieties.

By the term "arylaliphatic" is meant a hydrocarbon moiety, in which one or more aromatic moieties are substituted with one or more aliphatic groups. Thus the term "arylaliphatic" also includes hydrocarbon moieties, in which two or more aryl groups are connected via one or more aliphatic chain or chains of any length, for instance a methylene group. Typically, the hydrocarbon (main) chain includes 5, 6, 7 or 8 main chain atoms in each ring of the aromatic moiety. Examples of arylaliphatic moieties such as alkylaryl moieties include, but are not limited, to 1-ethyl-naphthalene, 1,1'-methylenebisbenzene, 9-isopropylanthracene, 1,2,3-trimethyl-benzene, 4-phenyl-2-buten-1-ol, 7-chloro-3-(1-methylethyl)-quinoline, 3-heptyl-furan, 6-[2-(2,5-diethylphenyl)ethyl]-4-ethyl-quinazoline or, 7,8-dibutyl-5,6-diethyl-isoquinoline.

Each of the terms "aliphatic", "alicyclic", "aromatic" and "arylaliphatic" as used herein is meant to include both substituted and unsubstituted forms of the respective moiety. Substituents my be any functional group, as for example, but not limited to, amino, amido, azido, carbonyl, carboxyl, cyano, isocyano, dithiane, halogen, hydroxyl, nitro, organometal, organoboron, seleno, silyl, silano, sulfonyl, thio, thiocyano, trifluoromethyl sulfonyl, p-toluenesulfonyl, bromobenzenesulfonyl, nitrobenzenesulfonyl, and methanesulfonyl.

The aliphatic and the optional alicyclic moieties, which the hydrocarbon backbone carries, may carry further moieties such as side chains. Such further moieties may be an aliphatic, alicyclic, aromatic, arylaliphatic or arylalicyclic group that typically is of a main chain length of 1 to about 10, to about 15 or to about 20 carbon atoms. These further moieties may also carry functional groups (supra).

The hydrocarbon backbone carries a plurality of a first moiety and of a second moiety. The first moiety is an aliphatic moiety with a main chain of about 3 to about 20 carbon atoms, including about 5 to about 20 carbon atoms, about 7 to about 20 carbon atoms, such as 3, 4, 5, 6, 7, 8, 9, 10, 11, 12, 13, 14, 15, 16, 17, 18, 19 or 20 carbon atoms or about 5 to about 15 carbon atoms. Further, the first aliphatic moiety has 0 to about 3 heteroatoms, including 1, 2 or 3 heteroatoms, such as N, O, S, Se or Si. An illustrative example of a suitable first aliphatic moiety is an alkyl moiety with a heteroatom, via which it is bonded to a carbonyl group carried by the aliphatic backbone of the polymer. Instead of a free carboxyl group the backbone thus carries an ester, a thio ester, a seleno ester or an amido group. In one embodiment the first aliphatic moiety is linked to the backbone via an amide bond which is formed by reacting the respective amine with the maleic anhydride polymer and is defined by an unbranched alkyl moiety, such as an n-octyl moiety. The first moiety is in the following also termed "$R^2$".

The second moiety may be alicyclic or aliphatic. Where the second moiety is alicyclic it has a main chain of about 3 to about 100, 4 to about 100 or 5 to about 100 carbon atoms, such as 5 to about 80, 5 to about 70, 5 to about 60, 5 to about 50, 5 to about 40, 5 to about 30 or 5 to about 20 carbon atoms carbon atoms, including 5, 6, 7, 8, 9, 10, 11, 12, 13, 14, 15, 16, 17, 18, 19, 20, 12, 22, 23, 24, 25, 26, 27, 28, 29 or 30 carbon atoms. The alicyclic moiety may further have 0 to about 40 heteroatoms, such as 0 to about 35, 0 to about 30, 1 to about 35, 1 to about 30, 0 to about 25, 0 to about 20, 0 to about 15 or 0 to about 10 heteroatoms. The second moiety may also be a cyclic moiety bound to a carbonyl group attached to the polymer backbone via an aliphatic bridge of up to 3 carbon atoms and up to 3 heteroatoms. This aliphatic bridge, e.g. a methylene, an ethylene, a propylene or an isopropylene bridge is in the following also termed "Z". A respective alicyclic moiety, whether directly bound to the carboxy group attached to the polymer backbone or linked thereto via a bridge Z, is in the following also termed "$R^4$".

Where the second moiety is aliphatic it has a main chain of about 2 to about 100, 3 to about 100 or 4 to about 100 carbon atoms, such as 3 to about 80, 2 to about 80, 3 to about 70, 3 to about 60, 3 to about 50, 3 to about 40, 3 to about 30 or 3 to about 20 carbon atoms carbon atoms, including 3, 4, 5, 6, 7, 8, 9, 10, 11, 12, 13, 14, 15, 16, 17, 18, 19, 20, 12, 22, 23, 24, 25, 26, 27, 28, 29 or 30 carbon atoms. The aliphatic moiety may further have 0 to about 40 heteroatoms, such as 0 to about 35, 0 to about 30, 1 to about 35, 1 to about 30, 0 to about 25, 0 to about 20, 0 to about 15 or 0 to about 10 heteroatoms. Where the second moiety is an aliphatic moiety, it further has a C≡C group or a azido group. Both the C≡C group and the azido group may be terminal groups of a chain included in the aliphatic moiety, e.g. its main chain. The third moiety, including an embodiment where it includes an alicyclic moiety $R^4$, is in the following also termed "$R^3$".

In some embodiments the polymer backbone only carries first and second moieties as defined above. In some embodiments some of the second moieties are modified to form a link (see below). Such a modified second moiety may also be taken to define a third moiety. In some embodiments the polymer backbone carries additional, e.g. third, optionally fourth or more moieties.

When viewing the background of the amphiphilic polymer of the invention as including iterative 3,4-functionalized butyl or 2,2-dimethyl-butyl units, the polymer may be taken to include a plurality of different repeat units. Each repeat unit may have two vicinal carboxy groups, or one carboxy group and one vicinal group that may be a keto group, an amide group, an ester group, a thioester group, a selenoester group or a silylester group.

The first repeat unit may accordingly be taken to be represented by the general formulae (I) or (Ia):

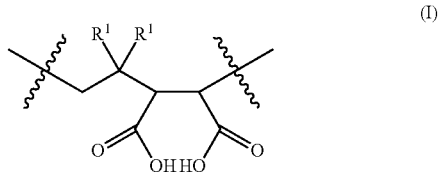

(I)

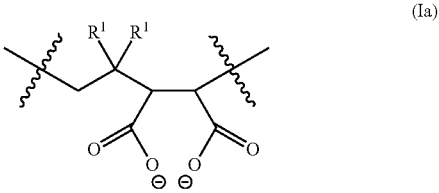

(Ia)

in which $R^1$ is H or methyl.

The second repeat unit may be taken to be represented by the general formulae (II) or (IIa):

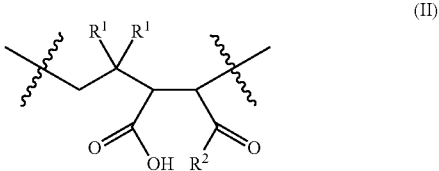

(II)

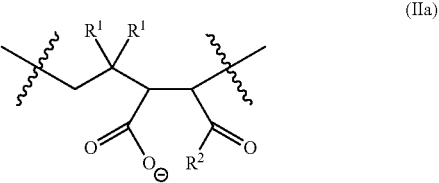

(IIa)

In formula (II) $R^1$ is H or methyl and $R^2$ is an aliphatic moiety with a main chain of about 3 to about 20 carbon atoms and is the first moiety as defined above.

The third repeat unit may be taken to be represented by the general formulae (III) or (IIIa):

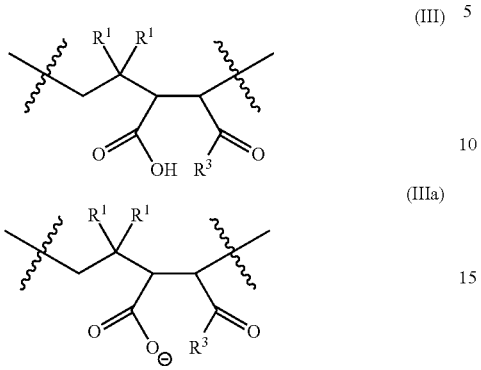

As can be taken from the above, formulas (Ia), (IIa), (IIIa) merely show a salt of the corresponding carboxylic groups. It is understood that the representation of a carboxylic group includes any salt from thereof (the counter ion thus not being depicted above). Therefore representations of salt forms are in the following generally omitted, unless it appears beneficial in terms of clarity. In formula (III) $R^1$ is H or methyl and $R^3$ is one of an alicyclic or aliphatic moiety as defined above. Accordingly, $R^3$ is in some embodiments an alicyclic moiety $R^4$, in which case the third repeat unit can also be represented by the following general formula:

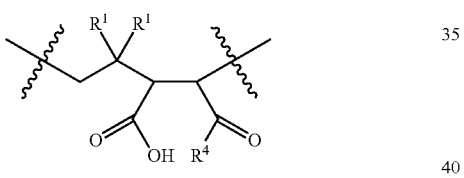

In some of these embodiments the alicyclic moiety includes a heteroatom, via which the alicyclic moiety is bound to the carbonyl group attached to the backbone of the polymer, thereby defining an amide group, an ester group, a thioester group, a selenoester group or a silylester group. In embodiments of an amide group, i.e. where the alicyclic moiety is bound to the carbonyl group attached to the backbone via a nitrogen atom included in the alicyclic moiety, the third repeat unit can also be represented by the following general formula:

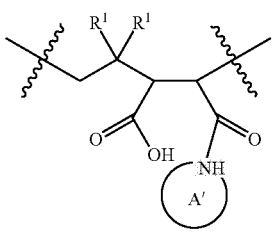

in which A' represents the residual portion of the alicyclic moiety $R^4$. In embodiments of an ester group, i.e. where the alicyclic moiety is bound to the carbonyl group via an oxygen atom of the alicyclic moiety, the third repeat unit can also be represented by the following general formula:

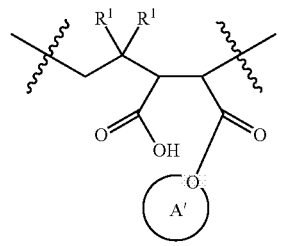

In embodiments of a selenyl ester group, i.e. where the alicyclic moiety is bound to the carbonyl group via a selenium atom, the third repeat unit can also be represented by the following general formula:

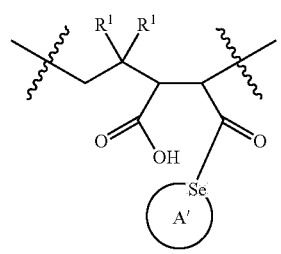

As explained above, a respective alicyclic moiety may in some embodiments be linked to the carbonyl group via a bridge Z. In such embodiments the third repeat unit can also be represented by the following general formula:

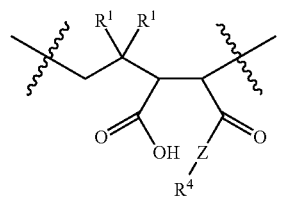

In some embodiments the bridge Z includes a heteroatom, e.g. N, O, Se, S or Si, via which the bridge Z is bound to the carbonyl group attached to the backbone. As three illustrative examples, the bridge Z may be —N—$CH_2$—, —O—$CH_2$—$CH_2$—, or —Se—$CH_2$—$CH(CH_3)$—$CH_2$—. In some embodiments the alicyclic moiety includes a heteroatom, via which the alicyclic moiety is bound to the bridge Z. Such a heteroatom may be a nitrogen atom, a sulphur atom, a selenium atom or a silicon atom. As two illustrative examples with such a heteroatom being N or O, the third repeat unit may in such embodiments be represented by one of the following formulas:

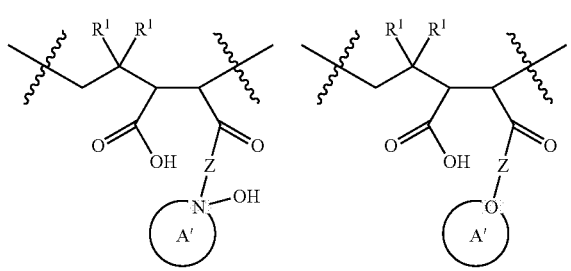

As explained above, the third moiety $R^3$ may be an aliphatic moiety, which has a C≡C group or an azido group. Accordingly, in some of these embodiments $R^3$ may be sketched as indicated by the following formulas,

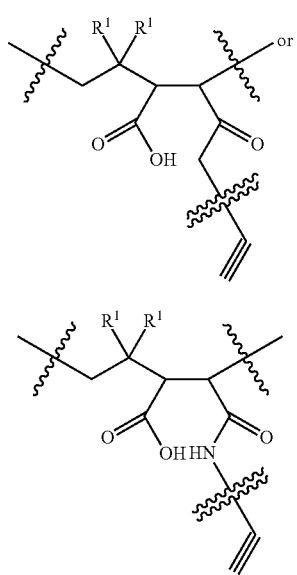

(IVa)

(IVb)

with a terminal C≡C group or as

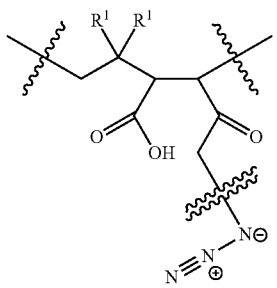

(IVc)

with a terminal azido group. In these sketchy representations ⸺ indicates that an aliphatic radical with a main chain of up to about 80 carbon atoms has been omitted for sake of clarity. In the case of formula (IVa) ⸺ may also represent a covalent bond, whereas in formula (IVb) it represents at least one missing carbon atom and in formula (IVc) at least two missing carbon atoms. As depicted in formula (IVb), in some embodiments the bridge Z includes a heteroatom, e.g. N, O, Se, S or Si, via which the bridge Z is bound to the to the carbonyl group attached to the backbone. In some of these embodiments $R^3$ may be sketched as indicated by the following formulas,

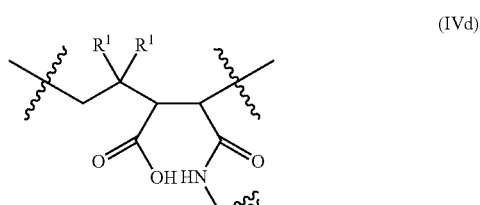

(IVd)

(IVe)

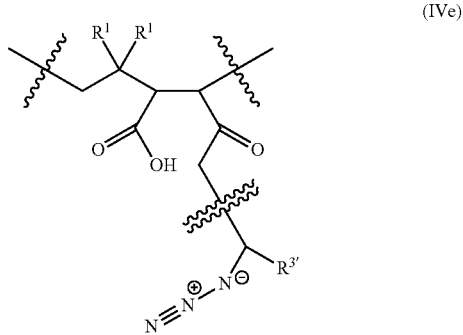

with an internal, i.e. non-terminal C≡C group or azido group, respectively. $R^{3'}$ in formulas (IVd) and (IVe) represents the portion of $R^3$ that continues beyond the depicted C≡C group or azido group. It is thus the portion of $R^{3'}$ that completes $R^3$ to an aliphatic moiety that has a main chain of about 3 to about 80 carbon atoms and 0 to about 30 heteroatoms.

The amphiphilic polymer according to the invention is generally a random polymer in that it includes the repeat units in random order. The first of three repeat units, i.e. the repeat unit of general formula (I),

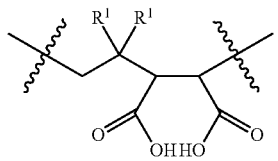

is present in the amphiphilic polymer in m units. The second of the three repeat units, i.e. the repeat unit of general formula (II),

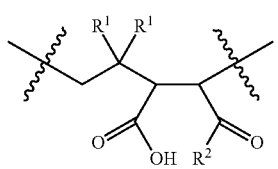

is present in the amphiphilic polymer in o units. The third of the three repeat units, i.e. the repeat unit of general formula (III),

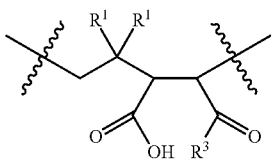

is present in the amphiphilic polymer in p units.

In formula (II) each of m, o and p is an independently selected integer from 1 to about 400, including from 2 to about 400 or about 3 to about 400, such as about 4 to about 400, about 3 to about 350, about 2 to about 300, about 3 to about 300, about 3 to about 250, about 3 to about 200, about 2 to about 200, about 3 to about 150, about 2 to about 150, about 3 to about 200, about 1 to about 200, about 3 to about 100, about 2 to about 100, about 1 to about 100, about 3 to about 50, about 2 to about 50, about 1 to about 50 or about 4 to about 50. As further illustrations, m may in some embodiments be selected in the range from about 5 to about 50, such as about 10 to about 45 including about 10 to about 43, whereas p may for instance be selected in the range from about 3 to about 40, such as about 3 to about 35 or about 3 to about 30, and p may for example be selected in the range from 3 to about 30, such as from 3 to about 25 or from 3 to about 20. The sum of m+o+p is selected in the range from about 10 to about 10000, including about 10 to about 8000, about 10 to about 6000, about 10 to about 5000, about 10 to about 4000, about 10 to about 2000, about 10 to about 1000, about 10 to about 750, about 10 to about 600, about 10 to about 400, about 10 to about 250, about 10 to about 150, about 10 to about 100, about 15 to about 150, about 20 to about 150, about 15 to about 100, or about 20 to about 100. In some embodiments each of m, o and p is an independently selected integer from about 2 to about 300, including from about 3 to about 300, about 3 to about 250, about 3 to about 200, about 3 to about 150 or about 2 to about 200, about 3 to about 100, about 2 to about 100, about 3 to about 80, about 2 to about 80, about 3 to about 40 or about 2 to about 40 and the sum of (m+o+p) is selected in the range from about 6 to about 400, including from about 10 to about 400, from about 10 to about 350, from about 10 to about 300, from about 10 to about 250, from about 10 to about 200, from about 6 to about 200, from about 10 to about 150, from about 6 to about 150, from about 10 to about 100, from about 6 to about 100, from about 10 to about 50 or from about 6 to about 50. In one embodiment the sum of (m+o+p) is 50. In another embodiment the sum of (m+o+p) is 32. In yet another embodiment the sum of (m+o+p) is 48. The ratio of m/(o+p) may be selected in the range from 0 to about 25, such as from 0 to about 20, from 0 to about 15, from 0 to about 12, from 0 to about 10, from 0 to about 8, from about 0 to about 6, to about 4, to about 3 or to about 2. In one embodiment the ratio of m/(o+p) is about 1.

The amphiphilic polymer may in some embodiments be of the general formula (VI):

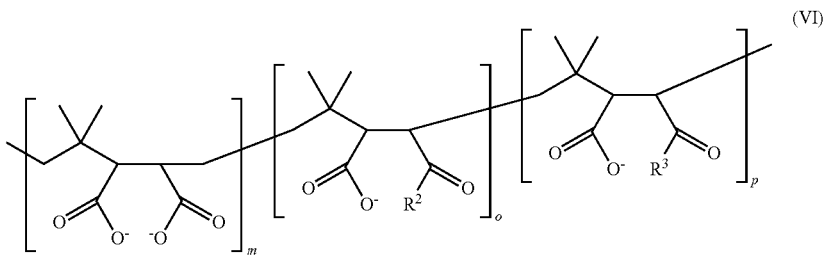

In formula (VI) each of m, o and p is an independently selected integer from 0 to about 400, as defined above. As mentioned above, the individual repeat units are generally arranged in random order in the polymer. Accordingly the brackets in formula (VI) merely serve in distinguishing the individual repeat units without indicating any blocks thereof. A polymer according to the invention may therefore encompass any sequence of these units. As an illustrative example a respective sequence may include the following arrangement of units:

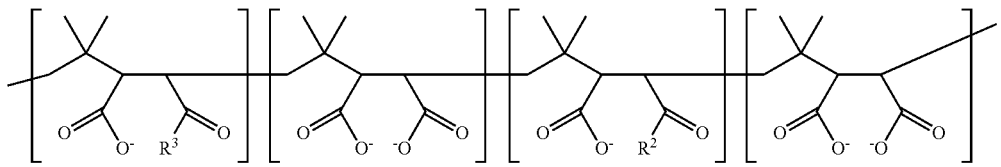

An amphiphilic polymer according to the invention may be prepared by the process described herein. The amphiphilic polymer is in some embodiments at least essentially free of branches and cross-links. In embodiments where $R^3$ is an alicyclic moiety ($R^4$) or a moiety —Z—$R^4$, the backbone of the polymer is generally a straight chain without any branches and cross-links. In embodiments where $R^3$ is an aliphatic moiety, its C=C group, e.g. terminal C=C group, or azido group, e.g. C=C group azido group, is available for any crosslinking or branching. This can be achieved in a coupling reaction with a compound or moiety that has a functional group suitable for undergoing a reaction with a C≡C group or azido group, such that a linkage is formed, which is generally a covalent linkage.

Both reaction partners, that is, a respective C≡C group and an azido group, may be terminal groups of a chain included in the aliphatic moiety, e.g. its main chain. It is noted in this regard that a position along a chain, i.e. a non-terminal position may involve steric hindrance by neighboring portions of the moiety, including functional groups. In such embodiments a reaction of a C≡C group or azido group in such an internal position may be slower when compared to a terminal C≡C group or azido group. In such embodiments a reaction may occur only with a certain fraction of the pairs of C≡C groups and azido groups, with the fraction being smaller than terminal groups when exposed to the same reaction conditions. Accordingly, it may be required to more carefully optimize reaction conditions when a non-terminal C≡C group or azido group, or a pair of such non-terminal groups is included in the compounds used.

Among the coupling methods, Huisgen 1,3-dipolar cycloaddition reactions ("click chemistry") have attracted much attention. The term "click chemistry" as used herein thus refers to such cycloaddition reactions and in particular to the cycloaddition of an azide and an alkyne—a reaction that may be in some embodiments be carried out under the catalysis of Cu(I) or under exposure to microwaves. The azido group can be taken to define the 1.3 dipole, the alkyne can then be termed a "dipolarophile". Examples of further groups that are suitable for 1,3-dipolar cycloadditions in that they provide a 1.3 dipole include, but are not limited to, a nitrilylide, a nitril imine, a nitril oxide, a diazo alkane, an azomethinylide, an azoxy group, a nitro group and a carbonyloxide. Examples of further groups that are suitable for 1,3-dipolar cycloadditions in that they provide a "dipolarophile" include, but are not limited to, an alkene, a carbonyl group and a nitrile group. These reactions have been applied to many different systems including nanoparticles. The required functionality on the quantum dot surface has been obtained via exchange of surface ligands [Binder, W H, et al., *J. Mater. Chem* (2007) 17, 2125-2132; Sun, EY, et al., *Molecular Imaging* (2006) 5, 2,122-128). However, the ligand exchange methods have several drawbacks related to the worsening of quantum dot luminescence properties and these methods are restricted to the incorporation of one particular functionality on the surface of the quantum dots.

In some embodiments the amphiphilic polymer is a polymer (B), which can be represented by the general formula (VII)

This polymer includes an additional repeat unit of general formulae (IV) or (IVa)

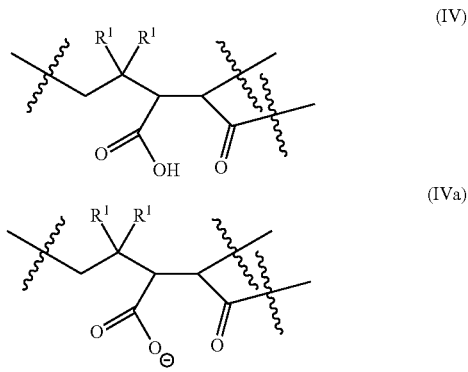

and is a reaction product of the polymer (A) defined above. The repeat unit of formula (IV) provides a branching or a linking site. Accordingly, in the repeat unit of formula (IV) $R^1$ is H or methyl. The repeat unit of general formula (IV) is included in the amphiphilic polymer (B) with a number of r units. R is an independently selected integer, selected in the range from 1 to about 400. The sum of p+r (cf. above) is selected in the range from about 1 to about 400, including from 2 to about 400 or about 3 to about 400, such as about 4 to about 400, about 3 to about 350, about 2 to about 300, about 3 to about 300, about 3 to about 250, about 3 to about 200, about 2 to about 200, about 3 to about 150, about 2 to about 150, about 3 to about 200, about 1 to about 200, about 3 to about 100, about 2 to about 100, about 1 to about 100, about 3 to about 50, about 2 to about 50, about 1 to about 50 or about 4 to about 50. As further illustrations, sum of p+r may in some embodiments be selected in the range from about 3 to about 40, such as about 3 to about 35, from about 3 to about 30, from 3 to about 25, from 3 to about 20 or about 5 to about 50, such as about 10 to about 45 including about 10 to about 43. Hence, the sum of m+o+p+r is selected in the range from about 10 to about 10000, including about 10 to about 8000, about 10 to about 6000, about 10 to about 5000, about 10 to about 4000, about 10 to about 2000, about 10 to about 1000, about 10 to about 750, about 10 to about 600, about 10 to about 400, about 10 to about 250, about 10 to about 150, about 10 to about 100, about 15 to about 150, about 20 to about 150, about 15 to about 100, or about 20 to about 100. In one embodiment the sum of (m+o+p+r) is 50. In another embodiment the sum of (m+o+p+r) is 32. In yet another embodiment the sum of (m+o+p+r) is 48. The ratio of m/(o+p+r) may be selected in the range from 0 to about 25, such as from 0 to about 20, from 0 to about 15, from 0 to about 12, from 0 to about 10, from 0 to about 8, from 0 to about 6, to about 4, to about 3 or to about 2. In one embodiment the ratio of m/(o+p+r) is about 1.

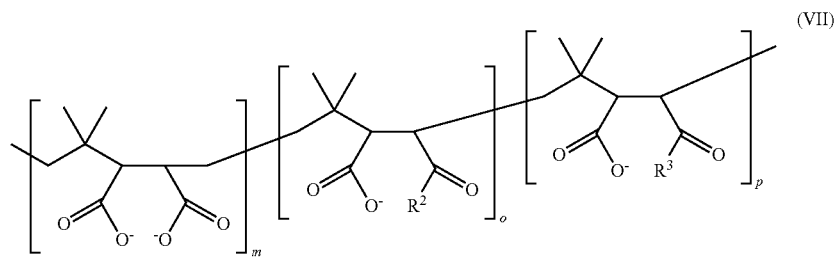

The unit (IV) of the polymer is covalently coupled to further matter such as a surface, a further polymer and a sensing molecule. The unit (IV) is coupled to such matter via a bridge that includes an aliphatic moiety with a main chain of about 3 to about 80 carbon atoms and 0 to about 20 heteroatoms. A respective heteroatom may be one of N, O, S, Se and Si. The bridge further includes a triazole ring. In some embodiments the bridge is represented by the formula

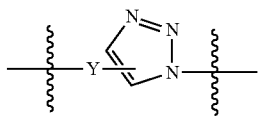

In this formula Y is an aliphatic moiety with a main chain of 1 to about 100, 1 to about 100 or 2 to about 100 carbon atoms, such as 1 to about 80, 2 to about 80, 1 to about 70, 1 to about 60, 1 to about 50, 1 to about 40, 1 to about 30 or 1 to about 20 carbon atoms, including 2, 3, 4, 5, 6, 7, 8, 9, 10, 11, 12, 13, 14, 15, 16, 17, 18, 19, 20, 12, 22, 23, 24, 25, 26, 27, 28, 29 or 30 carbon atoms. The aliphatic moiety may further have 0 to about 40 heteroatoms, such as 0 to about 35, 0 to about 30, 1 to about 35, 1 to about 30, 0 to about 25, 0 to about 20, 0 to about 15 or 0 to about 10 heteroatoms. FIG. 14 depicts two exemplary reaction products which may define a respective bridge that includes a triazole ring.

The bridge is obtained by a reaction involving the C≡C group or the azido group of the aliphatic moiety $R^3$ and a C≡C group or a azido group on the surface, the further polymer or the sensing molecule. In some embodiments the bridge couples the polymer (B) to a protein, to a nucleic acid molecule, to a low molecular weight organic compound (including a pharmaceutically active compound), a lipid, a saccharide, a polysaccharide, a cell and a virus.

In some embodiments the bridge couples the polymer (B) to a receptor molecule or moiety, a capture molecule or to a chromophore. Any sort of receptor/capture molecule/moiety or chromophore can be grafted onto the polymeric backbone as long as it has a suitable functional group that can be coupled, possibly via a bifunctional linking molecule, to a C≡C group or azido group. Illustrative examples include nucleophilic functional groups such as an amino group —$NH_2$ or a hydroxyl group —OH. Such receptor molecules include but are not limited to ionophores, peptide receptors, nucleic acid receptors, and monosaccharide receptors and polysaccharide receptors, for instance calixarenes, cavitands, porphirines, cryptands, crown ethers, cyclodextrines, peptides, polysacharides, immunoglobulins, nucleic acid molecules including DNA and RNA strands, diamides, other ionophores, chromophores or conductive polymers. FIG. 6 illustrates some examples of receptor/capture molecules which can be grafted onto the polymer (B).

In some embodiments the bridge couples the polymer (B) to an immunoglobulin (antibody), a fragment thereof or a proteinaceous binding molecule with antibody-like functions. Examples of (recombinant) antibody fragments are Fab fragments, Fv fragments, single-chain Fv fragments (scFv), diabodies, triabodies (Iliades, P., et al., *FEBS Lett* (1997) 409, 437-441), decabodies (Stone, E., et al., *Journal of Immunological Methods* (2007) 318, 88-94) and other domain antibodies (Holt, L. J., et al., *Trends Biotechnol.* (2003), 21, 11, 484-490). Single-chain Fv fragments are for instance fusions of variable regions from one heavy chain and one light chain of an immunoglobulin molecule. An example of a proteinaceous binding molecule with antibody-like functions is a mutein based on a polypeptide of the lipocalin family (WO 2003/029462; WO 2005/019254; WO 2005/019255; WO 2005/019256; Beste et al., *Proc. Natl. Acad. Sci. USA* (1999) 96, 1898-1903). Lipocalins, such as the bilin binding protein, the human neutrophil gelatinase-associated lipocalin, human Apolipoprotein D, human tear lipocalin, or glycodelin, possess natural ligand-binding sites that can be modified so that they bind to selected small protein regions known as haptens. Other non-limiting examples of further proteinaceous binding molecules so-called glubodies (see WO 96/23879), proteins based on the ankyrin scaffold (Mosavi, L. K., et al., *Protein Science* (2004) 13, 6, 1435-1448) or the crystalline scaffold (WO 2001/04144), the proteins described by Skerra (*J. Mol. Recognit.* (2000) 13, 167-187), AdNectins, tetranectins, avimers and peptoids. Avimers contain so called A-domains that occur as strings of multiple domains in several cell surface receptors (Silverman, J, et al., *Nature Biotechnology* (2005) 23, 1556-1561). Adnectins, derived from a domain of human fibronectin, contain three loops that can be engineered for immuno-globulin-like binding to targets (Gill, D. S. & Damle, N. K., *Current Opinion in Biotechnology* (2006) 17, 653-658). Tetranectins, derived from the respective human homotrimeric protein, likewise contain loop regions in a C-type lectin domain that can be engineered for desired binding (ibid.). Peptoids, which can act as protein ligands, are oligo(N-alkyl) glycines that differ from peptides in that the side chain is connected to the amide nitrogen rather than the α carbon atom. Peptoids are typically resistant to proteases and other modifying enzymes and can have a much higher cell permeability than peptides (see e.g. Kwon, Y.-U., and Kodadek, T., *J. Am. Chem. Soc.* (2007) 129, 1508-1509). Where desired, a modifying agent may be used that further increases the affinity of the respective moiety for any or a certain form, class etc. of target matter.

In some embodiments the bridge couples the polymer (B) to a further polymer. In some embodiments the further polymer is a further amphiphilic polymer (B') that includes the same repeat units as the polymer (B). Accordingly, the amphiphilic polymer (B') may likewise include repeat units of the general formulae (I), (II), (III) and (IV)

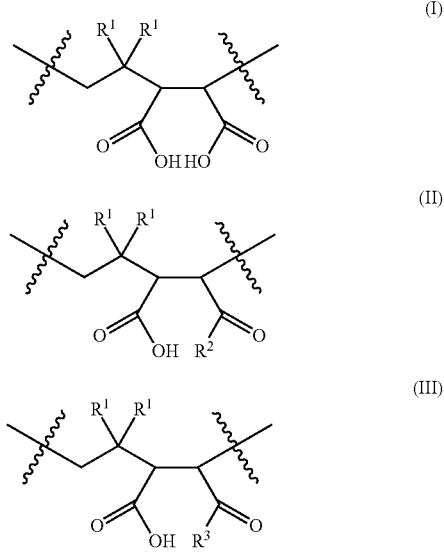

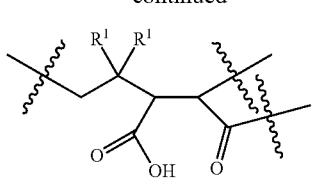
(IV)

or salts thereof. The repeat unit of general formula (I) is included in the amphiphilic polymer with a number of m units. The repeat units of general formulae (I), (II), (III) and (IV) are independently selected from the repeat units of general formulae (I), (II), (III) and (IV) of the amphiphilic polymer (B). The repeat units of general formulae (I), (II), (III) and (IV) of the amphiphilic polymer (B') are present numbers that correspond to those defined above for polymer (B). Accordingly, the repeat unit of general formula (I) is included in the amphiphilic polymer with a number of m units, the repeat unit of general formula (II) with a number of o units, the repeat unit of general formula (III) with a number of p units, and the repeat unit of general formula (IV) with a number of r units (see above). In one embodiment the repeat units of polymer (B) and the repeat units of polymer (B') are present in the same numbers. In other embodiments at least one repeat unit is present in different numbers when polymer (B) and polymer (B') are compared. Each of m, o and p of polymer (B') is an independently selected integer from about 3 to about 400. As for polymer (B), r is an independently selected integer from 1 to about 400. The sum of p+r is selected in the range from about 3 to about 400, while the sum of m+o+p+r is selected in the range from about 10 to about 10000. $R^1$ in repeat units (I)-(IV) is H or methyl. $R^2$ in repeat unit (II) is an aliphatic moiety with a main chain of about 3 to about 30 carbon atoms and 0 to about 3 heteroatoms, the heteroatoms being as defined above. $R^3$ in repeat unit (III) is an aliphatic moiety with a main chain of about 3 to about 80 carbon atoms and 0 to about 30 heteroatoms, the heteroatoms being as defined above. $R^3$ further has a C≡C group or an azido group.

The unit (IV) of the amphiphilic polymer (B') is covalently coupled to the amphiphilic polymer (B) via a bridge. Generally this bridge includes an aliphatic moiety with a main chain of about 3 to about 80 carbon atoms and 0 to about 20 heteroatoms. A respective heteroatom may be one of N, O, S, Se and Si. The bridge further includes a triazole ring. In some embodiments the bridge is represented by the formula

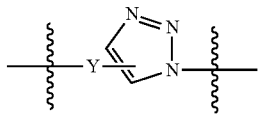

In this formula Y is an aliphatic moiety with a main chain of 1 to about 100, 1 to about 100 or 2 to about 100 carbon atoms, such as 1 to about 80, 2 to about 80, 1 to about 70, 1 to about 60, 1 to about 50, 1 to about 40, 1 to about 30 or 1 to about 20 carbon atoms, including 2, 3, 4, 5, 6, 7, 8, 9, 10, 11, 12, 13, 14, 15, 16, 17, 18, 19, 20, 12, 22, 23, 24, 25, 26, 27, 28, 29 or 30 carbon atoms. The aliphatic moiety may further have 0 to about 40 heteroatoms, such as 0 to about 35, 0 to about 30, 1 to about 35, 1 to about 30, 0 to about 25, 0 to about 20, 0 to about 15 or 0 to about 10 heteroatoms.

In this regard the invention also relates to an amphiphilic polymer (B") that includes one or more branches. The amphiphilic polymer (B") includes repeat units of the general formulae (I), (II), (III) and (IV):

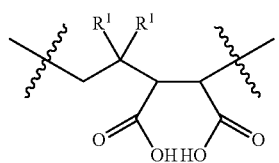
(I)

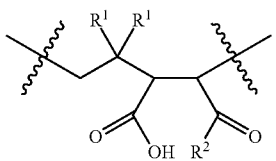
(II)

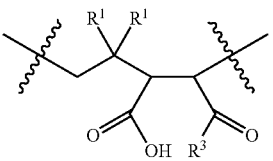
(III)

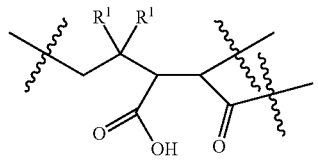
(IV)

or salts thereof. The repeat unit of general formula (I) is included in the amphiphilic polymer with a number of m units. The repeat unit of general formula (II) is v in the amphiphilic polymer with a number of o units. The repeat unit of general formula (III) is included in the amphiphilic polymer with a number of p units. The repeat unit of general formula (IV) is included in the amphiphilic polymer with a number of q units. Each of m, o and p are an independently selected integer from about 3 to about 1500. In contrast thereto, q is an independently selected even integer from 2 to about 1500. Further, the sum of p+q is selected in the range from about 3 to about 1500. The sum of m+o+p+q is selected in the range from about 10 to about 50000. $R^1$ in repeat units (I)-(IV) is H or methyl. $R^2$ in repeat unit (II) is an aliphatic moiety with a main chain of about of about 3 to about 30 carbon atoms and 0 to about 3 heteroatoms, the heteroatoms being as defined above. $R^3$ in repeat unit (III) is an aliphatic moiety with a main chain of about 3 to about 80 carbon atoms and 0 to about 30 heteroatoms, the heteroatoms being as defined above. $R^3$ further has a C≡C group or an azido group. Two units (IV) of the polymer (B") are covalently coupled via a bridge.

Generally this bridge includes an aliphatic moiety with a main chain of about 3 to about 80 carbon atoms and 0 to about 20 heteroatoms. A respective heteroatom may be one of N, O, S, Se and Si. The bridge further includes a triazole ring. In some embodiments the bridge is represented by the formula

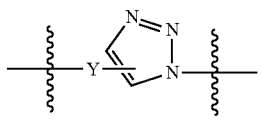

thereby defining a branch of the amphiphilic polymer (B"). In this formula Y is as defined above. In some embodiments the bridge is of the structure —Y—R⁵—Y—. R⁵ is an aryla-liphatic or arylalicyclic bridge that includes a triazole ring. Y' is, independently selected from Y, an aliphatic moiety with a main chain of 1 to about 100, 1 to about 100 or 2 to about 100 carbon atoms, such as 1 to about 80, 2 to about 80, 1 to about 70, 1 to about 60, 1 to about 50, 1 to about 40, 1 to about 30 or 1 to about 20 carbon atoms, including 2, 3, 4, 5, 6, 7, 8, 9, 10, 11, 12, 13, 14, 15, 16, 17, 18, 19, 20, 12, 22, 23, 24, 25, 26, 27, 28, 29 or 30 carbon atoms. The aliphatic moiety may further have 0 to about 40 heteroatoms, such as 0 to about 35, 0 to about 30, 1 to about 35, 1 to about 30, 0 to about 25, 0 to about 20, 0 to about 15 or 0 to about 10 heteroatoms.

In some embodiments a respective bridge couples the polymer (B) to a surface. The surface may be any surface such as the surface of solid matter, e.g. a solid slide, the surface of a cell or the surface of a virus particle. In some embodiments the surface is the surface of a nanocrystal. In order to allow the formation of such a bridge, the matter to which the polymer is to be coupled is provided with azido groups or alkyne functions. This may be achieved via any functional group present on the surface by a transformation or a coupling reaction. As an illustrative example, a thio-ether-bond may be formed on the surface, for example by using co functionalized thiols. Any suitable molecule that is capable of linking a selected nanocrystal to e.g. a bifunctional molecule having a alkyne or azido group may be used to immobilise the same on a nanocrystal. If desired, an additional (bifunctional) linking agent such as ethyl-3-dimethylaminocarbodiimide, N-(3-aminopropyl) 3-mercapto-benzamide, 3-aminopropyl-trimethoxysilane, 3-mercaptopropyl-trimethoxysilane, 3-(trimethoxysilyl) propyl-maleimide, or 3-(trimethoxysilyl) propylhydrazide may be used. Prior to reaction with the linking agent, the surface of the nanocrystals can be modified, for example by treatment with glacial mercaptoacetic acid, in order to generate free mercaptoacetic groups which can then employed for covalently coupling with a linking agent. It is understood that in other embodiments a moiety with aa alkyne or azido group may be directly synthesized on the respective surface, for example using photoactivation and deactivation.

In the process of forming an amphiphilic polymer according to the invention a maleic anhydride polymer of formula (V) is used as a reactant, which forms the hydrophilic backbone on the amphiphilic polymer:

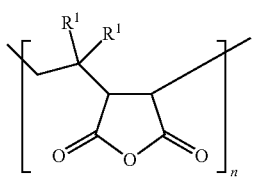

(V)

The maleic anhydride polymer may be the commercially available poly(isobutylene-alt-maleic anhydride) of Chemical Abstracts No. 26426-80-2, also termed isobutylene-maleic acid anhydride copolymer. It is inter alia available under the names BM 30AE20, Fibersorb™ SA 7200H, IB 6, KI Gel and Isobam®. It is available from e.g. Sigma-Aldrich (St. Louis, Mo., USA) or SinoChemexper Company (Shanghai, PRC). The maleic anhydride polymer may also be poly(ethylene-alt-maleic anhydride) of Chemical Abstracts No. 106973-21-1, also termed ethylene-maleic anhydride alternating copolymer. It is for example available from Rutherford Chemicals (Bayonne, N.J.) under product code 27109P, as well as under the names ZeMac® E 400 or ZeMac® E 60. In formula (I) above n may be any integer from about 10 to about 10000, such as about 10 to about 5000, about 10 to about 2000, about 10 to about 1000, about 20 to about 1000, about 10 to about 800, about 20 to about 800, such as about 10 to about 400. In one embodiment n is 50. In one embodiment n is 32. The above examples of maleic anhydride polymers are not to be considered as being limiting but every available maleic anhydride polymer (and also those yet to be synthesized), in particular a maleic anhydride polymer which may be prepared according to standard procedures as described are suitable to be used in the present invention. Respective maleic anhydride polymers may for instance be formed following the procedures described in U.S. Pat. Nos. 3,846,383 and 6,316,554. A general standard procedure used in the art is also summarized in the abstract of Frank, H. P., *Makro-molekulare Chemie* (1968) 114, 113-121 and involves the free-radical copolymerisation of maleic anhydride with an olefin in the presence of e.g. a peroxide.

As further reactants two at least monofunctional compounds are used. In the course of the process one of the compounds is converted to the first moiety R² described above. The other compound is converted into the second moiety R³ (supra). One functional group—if more than one is present—of each of the two compounds is capable of forming a linkage with an anhydride. The first compound is a monofunctional aliphatic compound. The first compound has an alkyl chain of about 3 to about 30 carbon atoms and 0 to about 2 heteroatoms. A respective heteroatom may be one of N, O, S, Se and Si. The second compound is an alicyclic or an aliphatic compound. If it is an alicyclic compound it has a main chain of about 5 to about 80 carbon atoms and 0 to about 30 heteroatoms. A respective heteroatom may be one of N, O, S, Se and Si. If the second compound is an aliphatic compound it may be (i) an aliphatic bridge of a lower alkyl chain bound to an alicyclic moiety, or (ii) it may have a main chain of up to 80 carbon atoms. If the second compound is an aliphatic bridge of a lower alkyl chain bound to an alicyclic moiety, it may be an aliphatic bridge of 1 to about 3 carbon atoms and 0 to about 2 heteroatoms. Again, a respective heteroatom may be one of N, O, S, Se and Si. This lower alkyl chain is substituted with an alicyclic moiety R⁴. The alicyclic moiety R⁴ is as defined above, i.e. it has a main chain of about 5 to about 80 carbon atoms and 0 to about 40 heteroatoms, e.g. 0 to about 30 heteroatoms. If the second compound is aliphatic with a main chain of up to 80 carbon atoms, it has a main chain of about 3 to about 80 carbon atoms. It may further include 0 to about 20 heteroatoms. Again, a respective heteroatom may be one of N, O, S, Se and Si. In addition to the functional group that is capable of forming a linkage with an anhydride it has a C≡C group or an azido group.

The reaction of a fraction of the anhydride rings with one of the compounds leads to the formation of the hydrophobic side chains that can interact with the hydrophobic surface of nanoparticles as described herein. The first compound, being aliphatic, may in some embodiments react with at least about 25% of the available anhydride rings, such as at least about 35%, at least about 50%, at least about 70% or at least about 75%. The second compound, being aliphatic or alicyclic, may in some embodiments react with at least about 5% of the available anhydride rings, such as at least about 8%, at least about 10%, at least about 15%, at least about 20% or at least about 25%.

The functional group of either of the two compounds that is capable of forming a linkage with an anhydride may be selected from, but is not limited to, an amino group, a hydroxyl group, a thiol group, a selenol group, a halogen group, an ether group, a thioether group or the like. The first compound has an alkyl chain of about 2 to about 30 carbon atoms, such as about 3 to about 30 carbon atoms, 2 to about 20 carbon atoms, or about 3 to about 20 carbon atoms, including about 5 to about 30 carbon atoms, about 5 to about 25 carbon atoms, about 5 to about 20 carbon atoms, about 5 to about 15 carbon atoms, about 7 to about 20 carbon atoms, such as 2, 3, 4, 5, 6, 7, 8, 9, 10, 11, 12, 13, 14, 15, 16, 17, 18, 19, 20, 12, 22, 23, 24 or 25 carbon atoms. Further, the first compound has 0 to about 2 heteroatoms, such as one heteroatom. The heteroatoms may for instance be N, O, S, Se or Si. Examples of suitable compounds with one functional group include, but are not limited to, alkylamines, wherein the alkyl group is as defined above. In one embodiment the alkylamine may be n-propylamine, n-butylamine, n-pentylamine, n-hexylamine, n-octylamine or n-dodecylamine.

The second compound may have or include an alicyclic moiety $R^4$ as defined above. It may also be aliphatic with an alkyl chain of about 3 to about 80 carbon atoms, including of about 3 to about 70 carbon atoms, about 3 to about 60 carbon atoms, of about 3 to about 40 carbon atoms, of about 10 to about 80 carbon atoms, of about 10 to about 60 carbon atoms, of about 25 to about 60 carbon atoms, of about 10 to about 40 carbon atoms, of about 3 to about 20 carbon atoms or about 3 to about 10 carbon atoms, such as 3, 4, 5, 6, 7, 8, 9, 10, 11, 12, 13, 14, 15, 16, 17, 18, 19, 20, 24, 25, 26, 27, 28, 29, 30, 31, 32, 33, 34, 35, 36, 37, 38, 39, 40, 41, 42, 43 or 44 carbon atoms. Further, where the second compound is a respective aliphatic compound, it may have 0 to about 40 heteroatoms, including 1 to about 40 heteroatoms, about 2 to about 40 heteroatoms, 0 to about 30 heteroatoms, about 2 to about 30 heteroatoms or about 0 to about 5 heteroatoms such as 1, 2, 3, 4, 5, 6, 7, 8, 9, 10, 11, 12, 13, 14, 15, 16, 17, 18, 19, 20, 21, 22, 25, 26, 27, 28, 29, 30, 31, 32, 33, 34, 35, 36, 37, 38, 39, 40, 41, 42 or 43 heteroatoms, such as N or O.

In the process of forming an amphiphilic polymer according to the invention the reaction between the maleic anhydride polymers of formula (V) (supra), the first compound and the second compound may be carried out in the presence of a base. Generally, any base suitable for the intended purpose may be used. In one embodiment the base is a nucleophilic base. A nucleophilic base is a base having basic properties as well as nucleophilic properties. Illustrative examples include, but are not limited to, lithium diisopropylamide, lithium tetramethylpiperidide, diisopropylethyl amine (Hünig's base), 1,5-diazabicyclo[4.3.0]-non-5-ene, 1,8-diazabicyclo[5.4.0]undec-7-ene, a bis(trimethylsilyl)amide, a hexamethyldisilazane and bismesitylmagnesium. As explained above, in some embodiments the second compound has a C≡C group or an azido group. These groups do generally not react to a significant extent, or do not react to a detectable extent, under suitable reaction conditions.

While it has been previously shown that poly(isobutylene-alt-maleic anhydride) is capable of undergoing a reaction with an aliphatic amine (abstract of Japanese patent application JP 57016004, Fernandez-Arguelles, M. T., et al., *Nano Letters* (2008) 7, 9, 2613-2617), the present inventors found that furthermore bi-, and higher functionalized compounds can be used as additional reactants in a one-pot synthesis. It is generally possible to control the reaction conditions in such a manner that the bi- or higher functionalized compound is allowed to undergo only one reaction, thereby forming only one link to the hydrocarbon backbone of the polymer. Remaining functional groups of the bi- or higher functionalized compound are subsequently available for coupling and cross-linking reactions. In this respect the hydrocarbon backbone of the amphiphilic polymer may additionally carry polar side groups and side chains having an alkyl chain of about 3 to about 80 carbon atoms and 0 to about 40 heteroatoms selected from N and O, the side chains having a crosslinkable group. Such a crosslinkable group may be an amino group, a hydroxyl group or a group containing a C=C bond, such as a terminal group —CH=CH$_2$. The crosslinkable group may be the same or different from remaining groups of the at least bifunctional compound. In embodiments where the functional groups are the same, those functional groups that are not allowed to react with the maleic acid anhydride polymer may be shielded from participating in a poly-merisation process. A large number of protecting groups, which are well known to those skilled in the art, is available for various functional groups. As an illustrative example, hydroxyl groups may be protected by an isopropylidene group. Such a protective group may be removed after polymerisation and thus the functional groups) that is/are no longer shielded are available for a coupling-, crosslinking or copolymerisation reaction. For example, the isopropylidene protective group shielding a hydroxyl group may be removed by acid treatment. Those skilled in the art will furthermore be aware that such protective groups may have to be introduced well in advance during the synthesis of such a bi- or higher functionalized compound.

In another embodiment the present invention provides a method of forming a water-soluble nanocrystal.

The term nanocrystal as used in the present invention may be considered as any nanomaterial with at least one dimension of for example ≤about 100 nm and that is single-crystalline. These materials are of huge technological interest since many of their electrical and thermodynamic properties show strong size dependence and can therefore be controlled through careful manufacturing processes. Semiconductor nanocrystals in the sub-10 nm size range are often referred to as quantum dots.

In accordance with the invention, any suitable type of nanocrystal (quantum dot) can be rendered water soluble, so as long as the surface of the nanocrystal can interact, for example, via hydrophobic interactions or van-der-Waals interactions, with an amphiphilic polymer as described herein. In this context, the terms "nanocrystal" and "quantum dot" may be used interchangeably.

A well established route that can be used to prepare high-quality semiconductor quantum dots is the decomposition of molecular precursors at high temperatures in a coordinating solvent (for an overview of previous techniques see e.g. Reed, M. A., *Scientific American* (1993), January, 118-123), possibly, in the presence of a negative ion source, e.g., TOP/Se, TOP/S, etc. This process was developed in 1993 by Murray et al. (*J. Am. Chem. Soc.* (1993), 115, 8706-8715) and yields quantum dots of CdE (E=Se, S, and Te). It involves the formation of a solution of dimethylcadmium in tri-n-octylphosphine (TOP) and a solution of the corresponding chalcogenide in TOP. The solutions are combined and rapidly injected into tri-n-octylphosphine oxide (TOPO) at high temperatures (~200° C.-300° C.). Thereby TOP/TOPO capped nano-crystals are obtained. The capping agent allows particle solubility in organic solvents, and plays a crucial role in preventing particle aggregation and electronically passivating the semiconductor surface. This so-called TOPO method permits the production of highly monodisperse nanoparticles in quantities of hundreds of milligrams in one single experiment.

In one embodiment, suitable nanocrystals have a nanocrystal core that includes a metal (M1) alone. For this purpose, M1 may be selected from the group consisting of an element of main group II, subgroup VIIA, subgroup VIIIA, subgroup IB, subgroup IIB, main group III or main group IV of the periodic system of the elements (PSE). Accordingly, the nanocrystal core may consist of only the metal element M1; the non-metal element A or B, as defined below, is absent. In this embodiment, the nanocrystal consists only of a pure metal from any of the above groups of the PSE, such as gold, silver, copper (subgroup Ib), titanium (subgroup IVb), terbium (subgroup IIIb), cobalt, platinum, rhodium, ruthenium (subgroup VIIIb), lead (main group IV) or an alloy thereof.

In another embodiment, the nanocrystal core used in the present invention may include two elements. Accordingly, the nanocrystal core may be a binary nanocrystal alloy that includes two metal elements, M1 and M2, such as any well-known core-shell nanocrystal formed from metals such as Zn, Cd, Hg, Mg, Mn, Ga, In, Al, Fe, Co, Ni, Cu, Ag, Au and Au.

Another type of binary nanocrystals suitable in the present invention may include one metal element M1, and at least one element A selected from main group V or main group VI of the PSE. Accordingly, the one type of nanocrystal suitable for use presently has the formula M1A. Examples of such nanocrystals may be group II-VI semiconductor nanocrystals (i.e. nanocrystals including a metal from main group II or subgroup IIB, and an element from main group VI) wherein the core and/or the shell includes CdS, CdSe, CdTe, MgTe, ZnS, ZnSe, ZnTe, HgS, HgSe, or HgTe. The nanocrystal core may also be any group III-V semiconductor nanocrystal (i.e. nanocrystals including a metal from main group III and an element from main group V). The core and/or the shell includes GaN, GaP, GaAs, GaSb, InN, InP, InAs, InSb, AlN, AlP, AlAs, AlSb. Specific examples of core shell nanocrystals that can be used in the present invention include, but are not limited to, (CdSe)-nanocrystals having a ZnS shell, as well as (CdS)-nanocrystals having ZnS shell.

The invention is not limited to the use of the above-described core-shell nanocrystals. In another embodiment, the nanocrystal of the invention can have a core consisting of a homogeneous ternary alloy having the composition $M1_{1-x}M2_xA$, wherein
(a) M1 and M2 are independently selected from an element of subgroup IIb, subgroup VIIa, subgroup VIIIa, subgroup Ib or main group II of the periodic system of the elements (PSE), when A represents an element of the main group VI of the PSE, or
(b) M1 and M2 are both selected from an element of the main group (III) of the PSE, when A represents an element of the main group (V) of the PSE.

In another embodiment nanocrystals consisting of a homogeneous quaternary alloy can be used. Quaternary alloys of this type have the composition $M1_{1-x}M2_xA_yB_{1-y}$, wherein
(a) M1 and M2 are independently selected from an element of subgroup IIb, subgroup VIIa, subgroup VIIIa, subgroup Ib or main group II of the periodic system of the elements (PSE), when A and B both represent an element of the main group VI of the PSE, or
(b) M1 and M2 are independently selected from an element of the main group (III) of the PSE, when A and B both represent an element of the main group (V) of the PSE.

Examples of this type of homogenous ternary or quaternary nanocrystals have been described, for instance, in Zhong et al, J. Am. Chem. Soc (2003) 125, 8598-8594, Zhong et al, J. Am. Chem. Soc (2003) 125, 13559-13553, or the International patent application WO 2004/054923.

Such ternary nanocrystals are obtainable by a process that includes forming a binary nanocrystal M1A by
  i. heating a reaction mixture containing the element M1 in a form suitable for the generation of a nanocrystal to a suitable temperature T1, adding at this temperature the element A in a form suitable for the generation of a nanocrystal, heating the reaction mixture for a sufficient period of time at a temperature suitable for forming said binary nanocrystal M1A and then allowing the reaction mixture to cool, and
  ii. reheating the reaction mixture, without precipitating or isolating the formed binary nanocrystal M1A, to a suitable temperature T2, adding to the reaction mixture at this temperature a sufficient quantity of the element M2 in a form suitable for the generation of a nanocrystal, then heating the reaction mixture for a sufficient period of time at a temperature suitable for forming said ternary nanocrystal $M1_{1-x}M2_xA$ and then allowing the reaction mixture to cool to room temperature, and isolating the ternary nanocrystal $M1_{1-x}M2_xA$.

In these ternary nanocrystals, the index x may have a value of $0.001<x<0.999$, for example of $0.01<x<0.99$, $0.1<x<0.9$ or of $0.5<x<0.95$. In other embodiments, x can have a value between about 0.2 or about 0.3 to about 0.8 or about 0.9. In quaternary nanocrystals, y may have a value of $0.001<y<0.999$, for example of $0.01<y<0.99$, or of $0.1<x<0.95$ or between about 0.2 and about 0.8.

In such II-VI ternary nanocrystals, the elements M1 and M2 included therein may be independently selected from the group consisting of Zn, Cd and Hg. The element A of the group VI of the PSE in these ternary alloys is preferably selected from the group consisting of S, Se and Te. Thus, all combinations of these elements M1, M2 and A are within the scope of the invention. In illustrative embodiments nanocrystals used in the present invention have the composition $Zn_xCd_{1-x}Se$, $Zn_xCd_{1-x}S$, $Zn_xCd_{1-x}Te$, $Hg_xCd_{1-x}Se$, $Hg_xCd_{1-x}Te$, $Hg_xCd_{1-x}S$, $Zn_xHg_{1-x}Se$, $Zn_xHg_{1-x}Te$, and $Zn_xHg_{1-x}S$.

In some illustrative embodiments, x as used in the above chemical formulas has a value of $0.10<x<0.90$ or $0.15<x<0.85$, and more preferably a value of $0.2<x<0.8$. In particularly preferred embodiments, the nanocrystals have the composition $Zn_xCd_{1-x}S$ and $Zn_xCd_{1-x}Se$. Such nanocrystals are preferred in which x has a value of $0.10<x<0.95$, and more preferably a value of $0.2<x<0.8$.

In certain embodiments in which the nanocrystal core is made from III-V nanocrystals of the invention, each of the elements M1 and M2 are independently selected from Ga and In. The element A may be selected from P, As and Sb. All possible combinations of these elements M1, M2 and A are within the scope of the invention. In some illustrative embodiments, nanocrystals have the composition $Ga_xIn_{1-x}P$, $Ga_xIn_{1-x}As$ and $Ga_xIn_{1-x}As$.

In one embodiment the nanocrystal includes semiconducting material, wherein as explained above the semiconducting material may include at least one of a metal and a metalloid.

In a method of the present invention the nanocrystal may first be provided in a suitable solvent or mixtures of such solvents. Suitable in this respect means that the nanocrystal should be soluble in the respective solvent. Examples of such solvents are, but not limited to, aprotic solvents and/or non-polar solvents, such as an aprotic non-polar solvent. The latter may be selected from hexane, heptane, cyclohexane, benzene, toluene, pyridine, dichloromethane, chloroform, carbon tetrachloride, carbon disulfide, dioxane, diethyl ether, diisopropylether, ethylene glycol monobutyl ether and tetrahydrofuran. The solvent may be removed after non-covalent or covalent interaction between the amphiphilic polymer and the nanocrystal has been allowed to occur.

In the method of the present invention the nanocrystal is contacted with an amphiphilic polymer according to the invention. As a result, the amphiphilic material is wrapped around the nanocrystal. In one embodiment the nanocrystal has a coordinating solvent via non-covalent interaction on its surface, wherein the solvent may include one or more aliphatic side chains. This coordinating solvent is exchanged for the amphiphilic polymer upon contacting the nanocrystal and the amphiphilic polymer. The amphiphilic polymer is fixed to the nanocrystals via non-covalent or covalent interaction. Such interaction may be, but is not limited to, a coordinative bond, a Casimir interaction, a hydrophobic interaction, hydrogen bonding, a solvation force and a Van-der-Waals interaction. To obtain a covalent interaction the polymer may include an additional repeat unit with a functional group that can undergo a chemical reaction with a functional group immobilized on the surface of the nano-crystal. Any suitable pair of functional groups and corresponding coupling reaction may be selected as long as the structure of the further repeat units (I), (II), (III) and optionally (IV) remains at least essentially intact. As two illustrative examples, the reaction of a halogen and an alcohol moiety (yielding an ether bridge) or a cross-coupling reaction such as a palladium catalyzed Heck coupling between an unsaturated halogenide and an alkene may be employed.

In one embodiment the amphiphilic polymer is added to the nanocrystal in a suitable solvent. A suitable solvent may be a polar solvent, such as a polar protic solvent. A protic solvent is a solvent that has, for example, a hydrogen atom bound to an oxygen as in a hydroxyl group or a nitrogen as in an amine group. More generally, any molecular solvent which contains dissociable $H^+$, such as hydrogen fluoride, is called a protic solvent. The molecules of such solvents can donate an $H^+$ (proton). Examples for polar protic solvents may be, but are not limited to, water, methanol, ethanol or acetic acid. In one embodiment of the present invention water may be used.

In the above procedure any organic solvent provided with the nanocrystal may be replaced by an aqueous solution after being contacted with the amphiphilic polymer of the invention. In one embodiment upon phase transfer to an aqueous solution the remaining anhydride rings open to yield negatively charged carboxyl groups, which provide electrostatic repulsion resulting in a stable dispersion of the nanocrystals.

In one embodiment of the present invention the method of forming a water-soluble nanocrystal includes providing a nanocrystal in a suitable solvent. In the method the nanocrystal is contacted with an amphiphilic polymer (A) as defined above. The amphiphilic polymer includes a hydrocarbon backbone with polar side groups, and non-polar aliphatic and optionally alicyclic moieties (supra). These moieties of the polymer thus allow non-covalent interactions between the amphiphilic polymer and the nanocrystal, thereby forming a water-soluble nanocrystal. The polymer may further include additional moieties that allow the formation of covalent interactions between the amphiphilic polymer and the nanocrystal.

Hence, using the process of the present invention described above it is possible to transfer nanocrystals into water. In addition, where alkyne or azido groups are present in the amphiphilic polymer (A), these groups allow the formation of cross-links to form a (further) polymer or a polymeric network. This cross-linking may be effected in various ways. For example, the C≡C or azido groups may be allowed to be cross-linked by reacting the amphiphilic polymer with an at least bifunctional (monomeric) compound. The at least bifunctional monomeric compound may be water soluble. The bifunctional (monomeric) compound may in turn be allowed to react with a further polymer such as an amphiphilic polymer (A'), which is of a structure and composition as defined for polymer (A), albeit values and groups selected independently thereof. In another embodiment the cross-linking is effected by allowing a reaction to occur between C≡C groups of a polymer (A) and azido groups of a polymer (A'). An 1,3-dipolar cycloaddition reaction that involves an alkyne and an azide yields an 1,2,3-triazole ring as depicted in FIG. 14. The reaction, which may be carried out under catalysis of copper(I), in particular formed in situ, thus leads to the formation of an amphiphilic polymer B as defined above. Such a polymer includes a branch providing repeat unit (IV) (supra) that is bonded to a bridge, which includes an 1,2,3-triazole ring.

As a result a polymer meshwork may be formed, wherein for example nano-crystals, as described herein, may be embedded as described above, may provide additional properties to the system, such as stability, solubility properties, polymer processability or catalytic properties. A meshwork in this respect may be a 3-dimensional system. In such a meshwork the amount of nanocrystals in the amphiphilic polymer may be in the range from about 0.01% (v/v) to about 50% (v/v), including from about 0.05% (v/v) to about 50% (v/v), such as about 0.05% (v/v) to about 40% (v/v), about 1% (v/v) to about 30% (v/v), about 1% (v/v) to about 25% (v/v). In typical embodiment the amphiphilic polymer in this system has repeat units (IV) as defined above, with the repeat units (IV) having been formed by a Huisgen 1,3-dipolar cycloaddition reactions ("click chemistry").

Among the coupling methods, Huisgen 1,3-dipolar cycloaddition reactions ("click chemistry") have previously attracted much attention. These reactions have been applied to many different systems including nanoparticles. However, the required functionality on the quantum dot surface was obtained via exchange of surface ligands. [Binder, W H, et al., *J. Mater. Chem.* (2007) 17, 2125-2132; Sun, E Y, Josephson, L, Weissleder, R, *Molecular Imaging* (2006) 5, 2, 122-128]. The ligand exchange methods have several drawbacks related to the worsening of quantum dot luminescence properties and these methods are restricted to the incorporation of one particular functionality on the surface of the quantum dots.

The present invention accordingly also relates to a water-soluble nanocrystal. The water-soluble nanocrystal includes on its surface via non-covalent or covalent interaction an amphiphilic polymer as defined above. As noted above, in some embodiments the polymer present on the surface of nanocrystal is a receptor moiety.

Semiconductor nanocrystals in the sub-10 nm size range, i.e. quantum dots, are bright fluorescence emitters with high quantum yields, high molar extinction coefficients over a wide range of wavelengths and high photostability. Quantum dots are therefore promising tools for sensing applications, found superior to traditional organic dyes. In addition, quantum dots provide the ability to optimize spectral overlap by size-tuning the QD photoluminescence, broad excitation spectra and large one- and two-photon absorption cross sections. A promising technique for the development of quantum dot nanosensors is the use of fluorescence (or Förster) resonance energy transfer (FRET). FRET is unique in providing fluorescence signals sensitive to molecular conformation, association, and separation in the range of 1-10 nm. It is well suited for events occurring at the nanometer scale, such as numerous biological processes. The water soluble polymers of the invention are well suited to provide quantum dots tailored for corresponding sensing applications. Specific sensing units can be attached to the QD sphere via the selection of the monomer units used, and where applicable by matter linked thereto via a cycloaddition reaction. Those skilled in the art will appreciate the fact that large bulky molecules such as ionophores complexating ions, such as ionized lanthanides, can be present on the surface of the QDs as shown in FIG. 2. The scope of receptor molecules that can be provided is largely limited when using conventional ligand exchange reactions. Furthermore, apart from sensing of anions via complexation reactions or via disturbance of FRET pathways, functionalized QDs according to the invention can be also used in magnetic resonance imaging (MRI) when complexating paramagnetic ions (such as $Gd^{3+}$). This is of particular interest for dual imaging (fluorescence and MRI) in clinical medicine.

QDs can for instance be used for highly sensitive cellular imaging or for in vitro imaging of pre-labeled cells. Quantum dots can also be used for delivering siRNA molecules into cells. Current research explores the use of quantum dots acting as the inorganic fluorophore for intra-operative detection of tumours using fluorescence spectroscopy.

In this regard the water-soluble nanocrystals of the invention allow immobilization of a large variety of receptor molecules for a large spectrum of analyte molecules. As an illustrative example, in embodiments where the moiety $R^3$ is or includes an alicyclic moiety $R^4$, e.g. in the form of a moiety —Z—$R^4$, the alicyclic moiety may be Kryptofix -22. A QD with an amphiphilic polymer bearing a Kryptofix-22 function can be used in metal recognition application. According to the method of the invention a respective polymer can be synthesised by grafting Kryptofix-22 together with an aliphatic monofunctional compound, e.g. n-octyl-amine, to poly (isobutylene-alt-maleic anhydride). The grafted alkyl chains, such as n-octyl-amine chains, are of non-polar and thus hydrophobic character and serve as an anchoring point for attachment to the TOPO terminated QD surface. The Kryptofix-22 function is an ionophore which can undergo complexation with selected ions to allow the study of the interaction between the QD and e.g. metal ions. As illustrated in the Examples, a straightforward nucleophilic reaction can for instance be carried out in the presence of additional non nucleophilic base such as diisopropylethyl amine (DIPEA).

Figure 5:
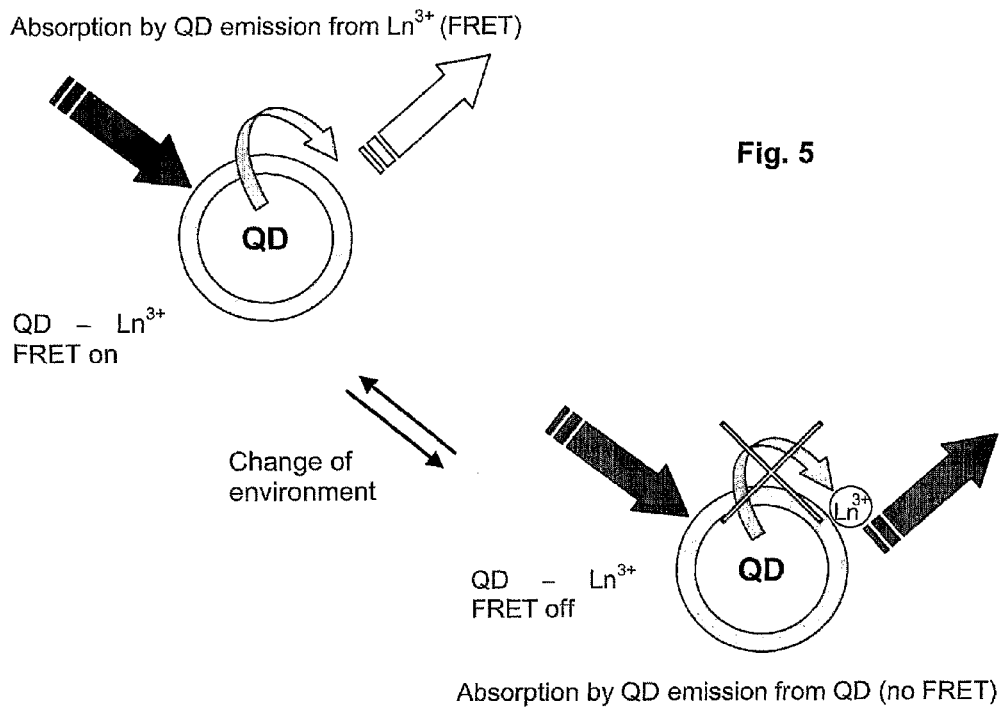
FIG. 5 illustrates the use of a quantum dot functionalized with the Kryptofix-22 receptor moiety in FRET-sensing. The Kryptofix-22 receptor moiety allows for sensing of Lanthanide ions, e.g. $Ln^{3+}$. Luminescent lanthanides ($Ln^{3+}$, $Eu^{3+}$, $Gd^{3+}$, $Tb^{3+}$ or $La^{3+}$) are immobilized on a quantum dot via a suitable receptor moiety.
Figure 6A:
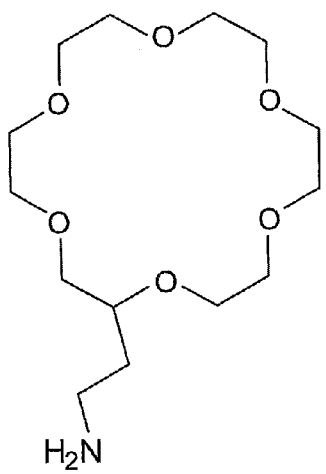
FIG. 6 depicts illustrative examples of receptor moieties that may be included in a polymer according to the invention (A: an 18-crown-6 moiety; B: a Calix[4]arene moiety having p-tert.-butyl substituents; C: a cyclodextrin moiety; D: a porphyrin moiety.
Figure 6B:
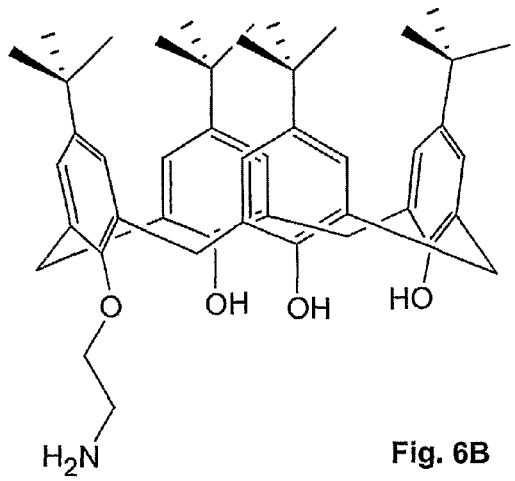
Figure 6C:
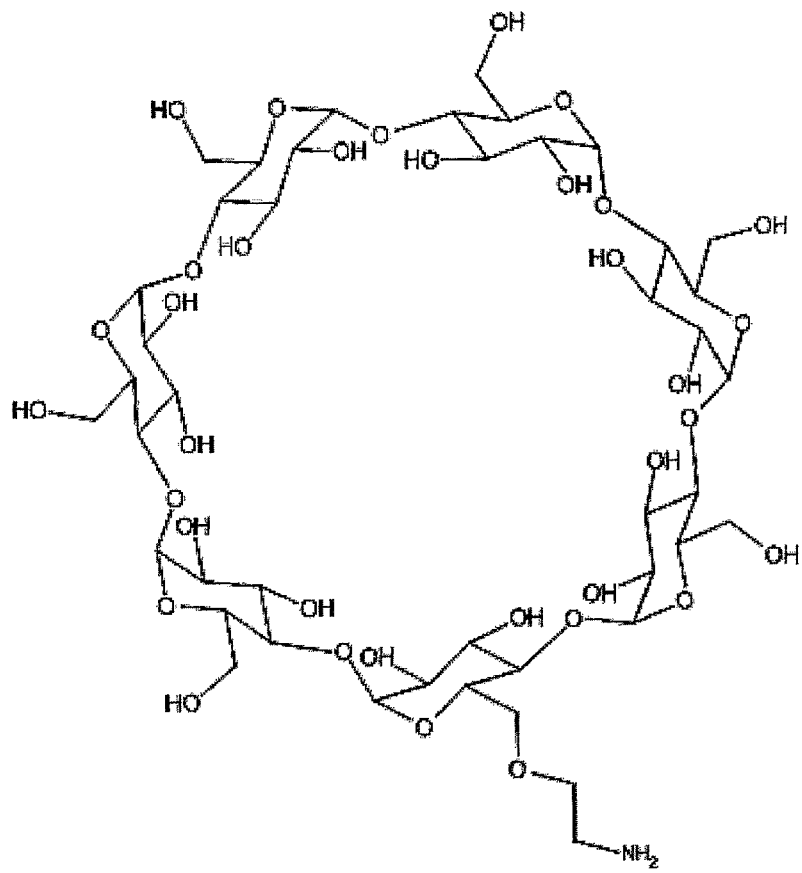
Figure 6D:
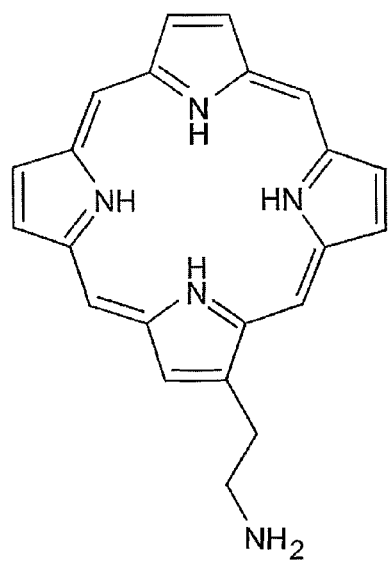
Figure 7:
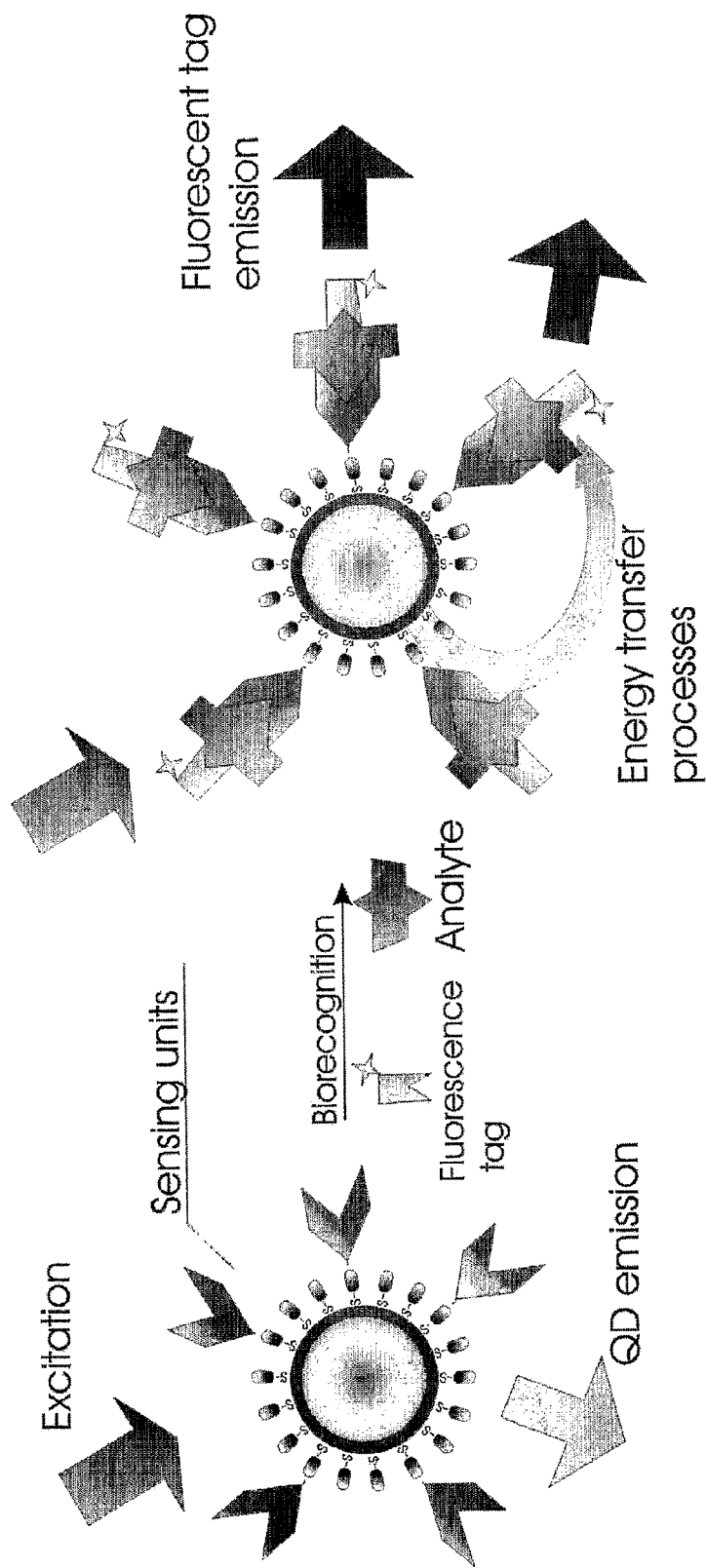
FIG. 7 illustrates FRET-based sensing using a quantum dot, on which a polymer with a suitable receptor moiety is immobilized. Sensing action is triggered by an external stimulus such as a change of temperature or pH or the presence of an analyte.

Hence, using the present invention quantum dots can be formed, on which receptor moieties or molecules are immobilized that are bound to e.g. luminescent Lanthanides $Ln^{3+}$ ($Eu^{3+}$, $Gd^{3+}$, $Tb^{3+}$, $La^{3+}$). Such QDs can be used in medical biodiagnostic, cell bioimaging, multimode imaging, in-vitro and in-vivo sensing, and chemical sensing applications. As already mentioned above, the use of such QDs provides several advantages, including low photobleaching rates of $Ln^{3+}$ and QDs, a high sensitivity of FRET with regard to the changes in the surroundings/the environment, a high sensitivity to counterions, pH, and solvent (cf. FIG. 5) and a large Förster radius (~7-11 nm). FIG. 5 illustrates the sensitivity of the FRET-sensing with QDs that have a Krptofix-22 receptor moiety on their surface, bound to $Ln^{3+}$ ions. It is noted that changes in the vicinity/in the environment result in different emissions observed.

Figure 8:
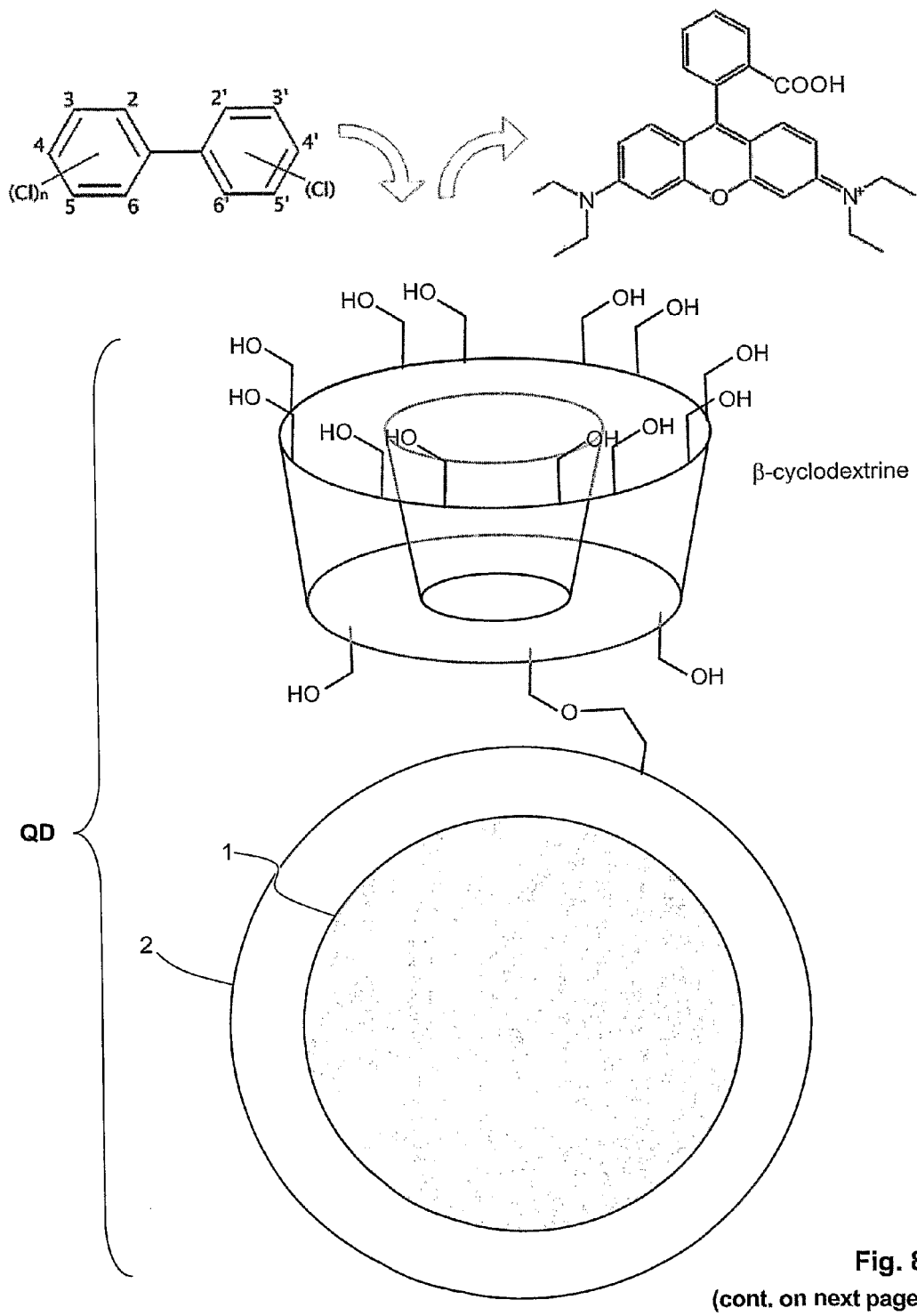
FIG. 8 illustrates the detection of one or more polychlorinated biphenyls (PCBs) using a quantum dot (1) on which a polymer (2) with a cylodextrine moiety is immobilized. The QD with a polymer is sketched and abbreviated "QD" on the first page of the figure, and further illustrated on the second page thereof. Before application in detection the cylodextrine moieties of the polymer are loaded with an organic chromophore. The PCB replaces the chromophore due to higher affinity to the cyclodextrine ligand.
Figure 9:
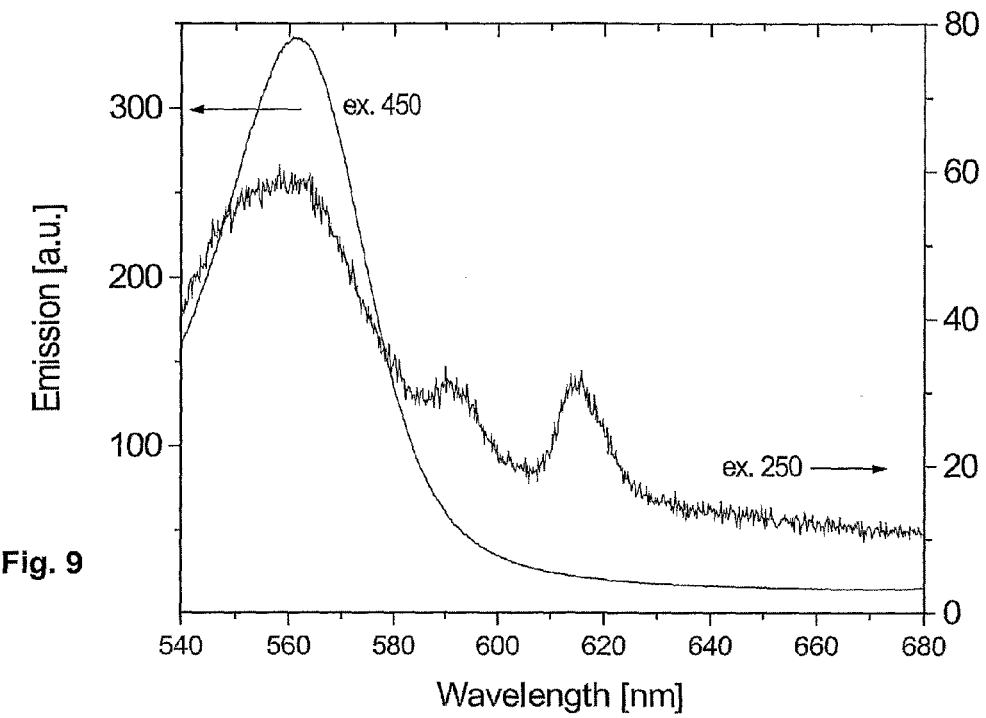
FIG. 9 depicts the emission spectra of a quantum dot on which a polymer with a Kryptofix receptor moiety is immobilized. The QD/polymer assembly is excited at 250 and 450 nm.

A further illustrative example are QDs functionalized with cyclodextrin for sensing of polichlorinatedbiphenyls (PCB). The obtained QDs provide an example of QDs coupled to a receptor suitable for a sensing process. The synthesis of an amphiphilic polymer bearing cyclodextrin receptors is described in the Examples below. In use, i.e. in the sensing system, the cyclodextrin is loaded with an organic chromophore, which is released when the analyte (PCB) is present in the environment. Quantitative determination of analyte concentration can be performed by monitoring the QD emission (when FRET is present) or the chromophore emission decay (when there is no FRET and the QD serves as the internal standard for the concentration) (see FIG. 8).

Sensing can be carried out in solution (surface-coated QDs suspended in water), in a polymeric matrix (polymeric micro spheres serving as a sensing device), or on a surface. In the latter case surface-coated quantum dots may be deposited on a surface directly, or they may be encapsulated in a polymeric film. Additionally, such surface-functionalized QDs with covalently attached recognition receptors can be used for nanofabrication.

As explained above, a [3+2] cycloaddition reaction allows for a wide range of receptor molecules or moities that can be linked to the QDs of the invention via alkyne or azido groups, including terminal alkyne or azido groups, where the moiety $R^3$ is an aliphatic compound with a main chain of about 3 to about 80 carbon atoms. Alkyne and in particular azido groups can be obtained from a variety of functional groups well within the skill of the skilled artisan. As an illustrative example, an azide can be obtained by reacting an alcohol or an alkene with $HN_3$. An alkyne can for instance be obtained by 1,2-elimination of an alkene derivative or by reacting a functional groups such as a halogen group with an acetylide. Furthermore, a bifunctional compound, which may for instance carry an azido or alkyne group and another functional group suitable for a coupling reaction, including sulfo-SMC, sulfo-SMCC, NHS or sulfo-NHS, may be used to provide alkyne or azido groups. Such an approach may for instance be chosen in cases where a direct conversion of a functional group into a desired C≡C or azido group appears difficult.

Figure 14A:
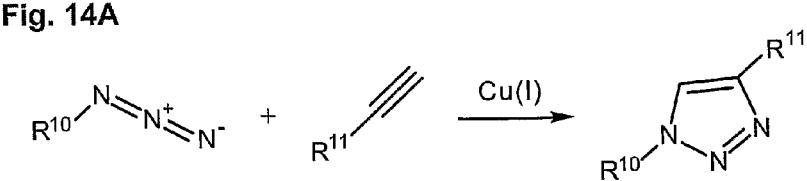
FIG. 14A is an illustration of a Huisgen cycloaddition between an azido group and a C≡C group. One of $R^{10}$ and $R^{11}$ may be a residual portion of a polymer (A) according to the invention, positioned in a repeat unit (III) thereof, and the other one of $R^{10}$ and $R^{11}$ may be a further compound or a bridge on a surface (cf. the description for details).
Figure 14B:
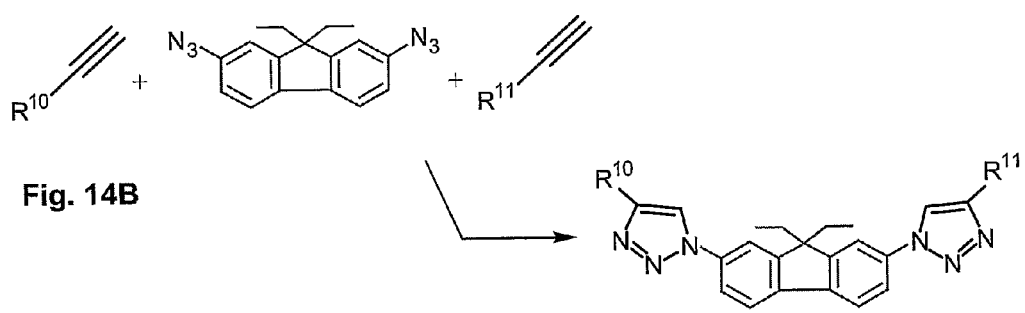
FIG. 14B is an illustration of a further Huisgen cycloaddition of two C≡C groups, which are being coupled using a bifunctional compound with two azido groups. See FIG. 14A for the definition of $R^{10}$ and $R^{11}$.
Figure 14C:
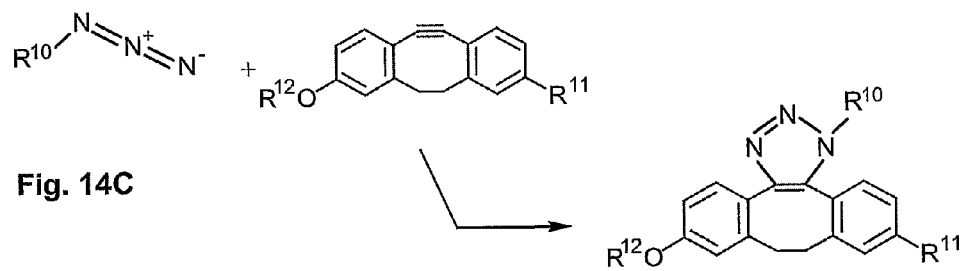
FIG. 14C depicts yet a further example of a Huisgen cycloaddition between an azido group and a C≡C group. A 4-dibenzocyclooctynoxy compound with $R^{12}$=aryl, alkyl, cycloalkyl, or arylalkyl with a main chain of 1 to about 20 carbon atoms and 0 to about 5 heteroatoms is used as the alkyne. This alkyne can be formed in situ from the corresponding cyclopropenone compound (FIG. 14D).
Figure 14D:
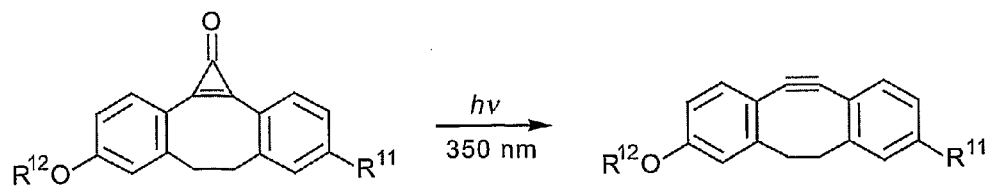

In some embodiments a receptor/capture molecule or moiety may be linked to a bridging moiety with a functional group that can be converted into an azido or alkyne group. The bridging moiety may be coupled to a further moiety such as a label or a further nanocrystal according to the invention. It may also include an additional functional group for coupling with another molecule or with a surface. An illustrative example of such a bridging moiety is a derivative of 4-dibenzocyclooctynol as described by Poloukhtine et al. (*J. Am. Chem. Soc.* (2009) doi: 10.1021/ja9054096) (see also FIG. 14C). Such a dibenzocyclooctyne compound can be formed in situ from a cyclopropenone as depicted in FIG. 14D (ibid.), thereby allowing a photochemically triggered click reaction. Decarbonylation of the cyclo-propenone can be achieved within few hundred picoseconds upon irradiation with 350 nm light. Thereby a cosslinking to the surface of a living cell is achievable (ibid).

Figure 10A:
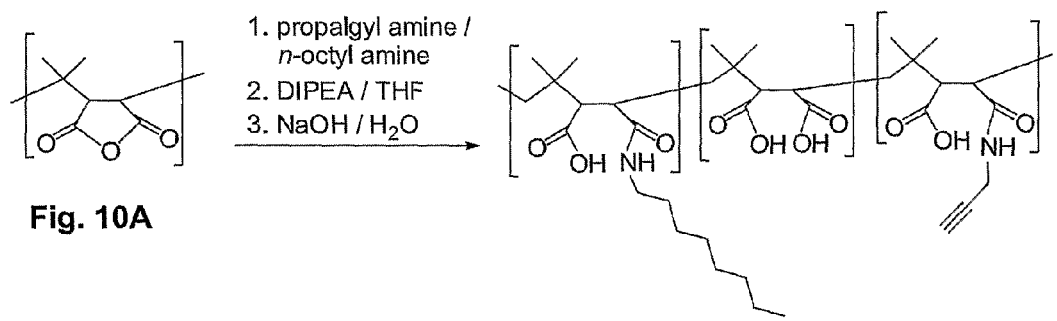
FIG. 10 depicts the synthesis of polymers functionalized with azide (A) and acetylene (B) functionalities.
Figure 10B:
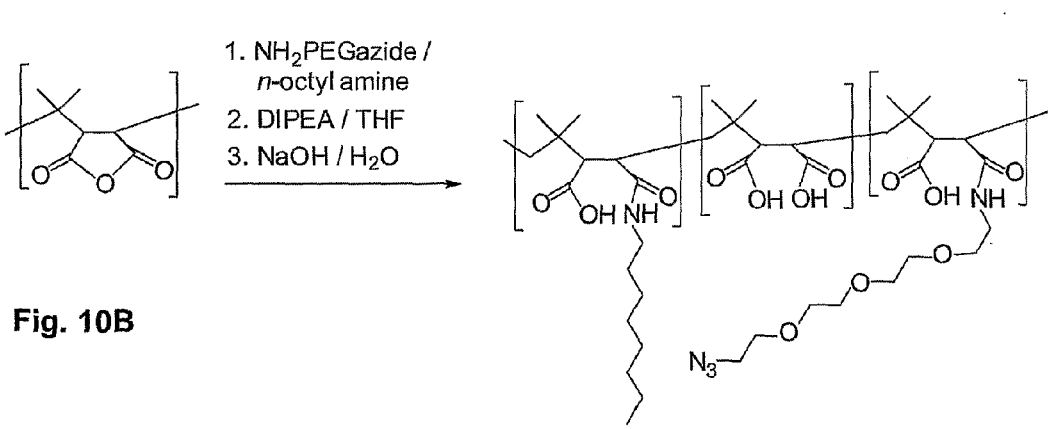

FIG. 10 illustrates the one-pot synthetic method to attach one or each of the "click chemistry" precursors (i.e. azide and acetylene functionalities) onto the amphiphilic polymer coatings. Coating of these amphiphilic polymers onto TOPO-terminated QDs gives water soluble azide- or acetylene-functionalized QDs. These QDs can be attached to each other, or to nanomaterials or receptors. Examples of suitable receptors for sensing applications include but are not limited to ionophores, peptide receptors, nucleic acid receptors and mono- and polysaccharides receptors, for example calixarenes, cavitands, porphirines, cryptands, crown ethers, cyclodextrines, other ionophores, or chromophores (see also above, cf. also FIG. 6 for examples.

Further examples of capture molecules are molecules that have a high affinity for a certain metal ion, e.g. metal chelator compounds. Examples of suitable metal chelators are ethylenediamine, ethylenediaminetetraacetic acid (EDTA), ethylene glycol tetraacetic acid (EGTA), diethylenetriaminepentaacetic acid (DTPA), N,N-bis(carboxymethyl)glycine (also called nitrilotriacetic acid, NTA), 1,2-bis(o-aminophenoxy) ethane-N,N,N',N'-tetraacetic acid (BAPTA), 2,3-dimercapto-1-propanol (dimmercaprol), porphine or heme. A respective metal ion may define a receptor molecule for a peptide of a defined sequence, which may also be included in a protein. In line with the standard method of immobilised metal affinity chromatography used in the art, for example an oligohistidine tag of a respective peptide or protein is capable of forming a complex with copper ($Cu^{2+}$), nickel ($Ni^{2+}$), cobalt ($Co^{2+}$), or zinc ($Zn^{2+}$) ions, which can for instance be presented by means of the chelator nitrilotriacetic acid (NTA).

A further example of a capture molecule with specificity for a selected analyte molecule are avidin or streptavidin that form a complex with a biotin moiety. A further example of a capture moiety is an affinity tag. Examples of an affinity tag include, but are not limited to biotin, dinitrophenol or digoxigenin, oligohistidine, polyhistidine, an immuno-globulin domain, maltose-binding protein, glutathione-S-transferase (GST), calmodulin binding peptide (CBP), FLAG'-peptide, the T7 epitope (Ala-Ser-Met-Thr-Gly-Gly-Gln-Gln-Met-Gly), maltose binding protein (MBP), the HSV epitope of the sequence Gln-Pro-Glu-Leu-Ala-Pro-Glu-Asp-Pro-Glu-Asp of herpes simplex virus glycoprotein D, the hemagglutinin (HA) epitope of the sequence Tyr-Pro-Tyr-Asp-Val-Pro-Asp-Tyr-Ala or the "myc" epitope of the transcription factor c-myc of the sequence Glu-Gln-Lys-Leu-Ile-Ser-Glu-Glu-Asp-Leu.

The broad availability of receptor molecules or moieties that can be immobilized on QDs using the present invention allows for the detection of various target molecules. Examples of a suitable target molecule include, but are not limited to, a peptide, a polypeptide, a protein, a peptoid, a nucleic acid molecule, a metabolite, a drug molecule, a drug candidate molecule, a drug metabolite, a lipid, a carbohydrate, a vitamin, a synthetic polymer, a cell, a microorganism, a virus or any combination thereof, to name a few.

As explained above, in some embodiments there is a polymer (B) immobilized on the surface of a nanocrystal. The polymer (B) includes repeat units (IV) that are linked to a bridge. This bridge may provide a link to other matter, such as receptor moieties or a further polymer (B') immobilized on another nanocrystal. In some embodiments this bridge provides a link to a surface (supra). The surface may be any surface such as the surface of solid matter, e.g. a solid slide, as well as the surface of a cell or the surface of a virus particle. As also explained above, the formation of such a bridge can be achieved by providing azido groups or terminal alkyne functions on the matter to which the nanocrystal with a polymer is to be coupled. Hence, the present invention also provides a nanocrystal with a polymer as defined above immobilized thereon, coupled to a surface.

In some embodiments the invention provides a plurality of water-soluble nanocrystals. Accordingly, in some embodiments a plurality of water-soluble nanocrystals immobilized on a surface is provided. The surface is in some embodiments a metal or metalloid surface. The nanocrystals of the plurality of nanocrystals include on their surface via non-covalent or covalent interaction an amphiphilic polymer (B) as defined above. The amphiphilic polymer (B) has repeat units of general formula (I) in a number of m units. It further has repeat unit of general formula (II) in a number of o units. It has repeat units of general formula (III) in a number of p units. Further, a repeat unit of general formula (IV) is included in the amphiphilic polymer with a number of r units (see above for further details). The repeat unit (III) includes a moiety $R^3$ that is an aliphatic moiety (supra). This aliphatic moiety has a terminal C≡C group or a terminal azido group. A unit (IV) of a the polymer B is covalently bonded to a bridge D. The bridge D is in turn covalently linked to the surface. The bridge D is of the structure -$G^1$-$R^5$-$G^2$-. $G^1$ and $G^2$ of the bridge D are independent from one another an aliphatic bridge of 1 to about 80 carbon atoms, including of 1 to about 70 carbon atoms, about 2 to about 70 carbon atoms, 1 to about 60 carbon atoms, about 2 to about 70 carbon atoms, 1 to about 40 carbon atoms, about 2 to about 40 carbon atoms, about 10 to about 80 carbon atoms, of about 10 to about 60 carbon atoms, of about 25 to about 60 carbon atoms, of about 10 to about 40 carbon atoms, of 1 to about 20 carbon atoms, about 2 to about 20 carbon atoms or 1 to about 10 carbon atoms, such as 1, 2, 3, 4, 5, 6, 7, 8, 9, 10, 11, 12, 13, 14, 15, 16, 17, 18, 19, 20, 24, 25, 26, 27, 28, 29, 30, 31, 32, 33, 34, 35, 36, 37, 38, 39, 40, 41, 42, 43 or 44 carbon atoms. Further, the aliphatic bridges $G^1$ and $G^2$ may include, independent from one another, 0 to about 20 heteroatoms, including 1 to about 20 heteroatoms, about 2 to about 20 heteroatoms, 0 to about 15 heteroatoms, about 1 to about 15 heteroatoms or about 0 to about 5 heteroatoms such as 1, 2, 3, 4, 5, 6, 7, 8, 9, 10, 11, 12, 13, 14, 15, 16, 17, 18, 19, or heteroatoms, such as N, O, S, Se or Si.

$R^5$ is an arylaliphatic or arylalicyclic bridge that includes a triazole ring. Typically the bridge $R^5$ has a main chain of about 2 to about 40 carbon atoms, including of about 2 to about 35 carbon atoms, about 3 to about 40 carbon atoms, of about 3 to about 35 carbon atoms, of about 2 to about 30 carbon atoms, of about 10 to about 30 carbon atoms, of about 5 to about 30 carbon atoms, of about 2 to about 25 carbon atoms, of about 2 to about 20 carbon atoms or about 2 to about 10 carbon atoms, such as 2, 3, 4, 5, 6, 7, 8, 9, 10, 11, 12, 13, 14, 15, 16, 17, 18, 19, 20, 24, 25, 26, 27, 28, 29, 30, 31, 32, 33, 34, 35, 36, 37, 38, 39 or 40 carbon atoms. Further the main chain of $R^5$ may have 1 to about 15 heteroatoms, including 1 to about 12 heteroatoms, about 2 to about 15 heteroatoms, about 2 to about 12 heteroatoms, 1 to about 10 heteroatoms or 1 to about 5 heteroatoms such as 1, 2, 3, 4, 5, 6, 7, 8, 9, 10, 11, 12, 13, 14 or 15 heteroatoms, such as N, O, S, Se or Si.

The nanocrystals of the plurality of nanocrystals are coupled to the surface via the bridge D. This bridge D is covalently bonded to a unit (IV) of a nanocrystal and to the surface, e.g. a metal or metalloid surface. The bridge D is obtained by a reaction involving the terminal C≡C group or the terminal azido group of the aliphatic moiety $R^3$ and a terminal C≡C group or a terminal azido group on the surface. Typically, such a reaction leading to the formation of a respective bridge falls under the so called "click chemistry" as detailed above. A terminal C≡C group or a terminal azido group may be provided on the surface by any suitable means (cf. also above). An illustrative example of providing a terminal C≡C group or a terminal azido group on a surface is depicted in FIG. 11. Further, FIG. 12 illustrates a glass surface covered with a plurality of QDs according to the invention. The dark zone in the middle of the picture represents an area where a layer of the quantum dot coating has been removed by scratching. Fluorescence is present only in areas covered with QDs.

The formation of the bridge D between a surface and a plurality of nanocrystals can be locally restricted to certain areas of the surface. This can be achieved by only bringing the selected areas to be covered in contact with the plurality of nanocrystals that include on their surface a polymer according to the invention. The remaining areas may be covered with other matter in order to avoid contact with the plurality of nanocrystals. No such covering is in some embodiments required, where means are used to specifically direct the plurality of quantum dots to selected areas of the surface. Thereby any desired surface pattern may be created on the surface. As an illustrative example a surface pattern can be formed by using a stamp, e.g. a poly(dimethylsiloxane) (PDMS) stamp as described by Rozkiewicz et al. (*Angew. Chem. Int. Ed.* (2006) 45, 5292-5296). Microcontact printing is carried out by inking the stamp in a plurality of functionalized (supra) nanocrystals. In some embodiments the nanocrystals are provided in a fluid such as a liquid or inking a stamp. The stamp may then be dried, e.g. by the flow of a gas such as nitrogen. Subsequently the stamp with the nanocrystals is brought in contact with the surface.

Figure 13A:
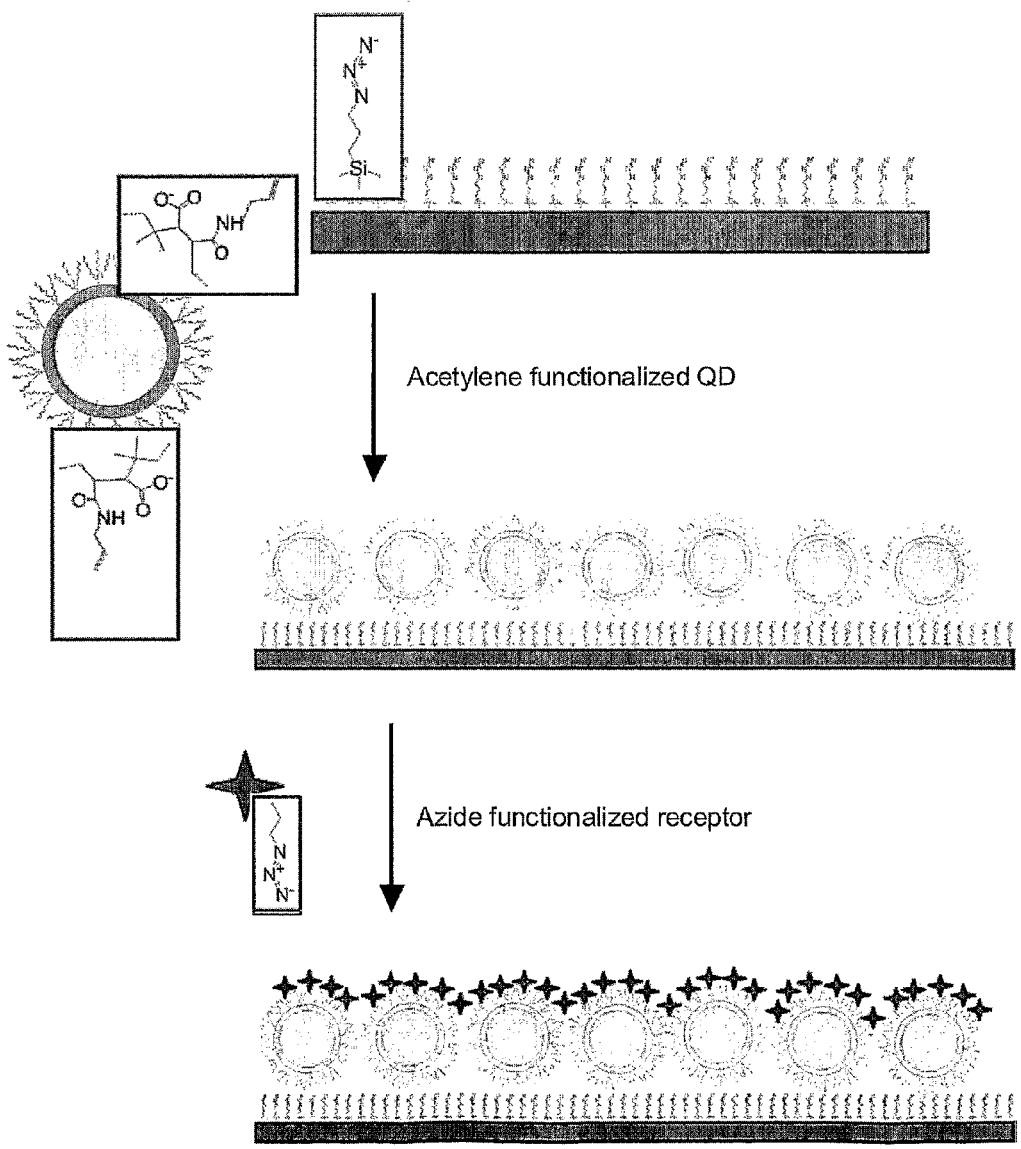
FIG. 13A depicts the formation of surface patterns, which can be carried out as a 2D or 3D fabrication, e.g. by controlled deposition or microcontact printing, using click chemistry and QDs with a polymer of the invention immobilized thereon. Depicted it the use of a poly(dimethylsiloxane) (PDMS) stamp.
Figure 13B:
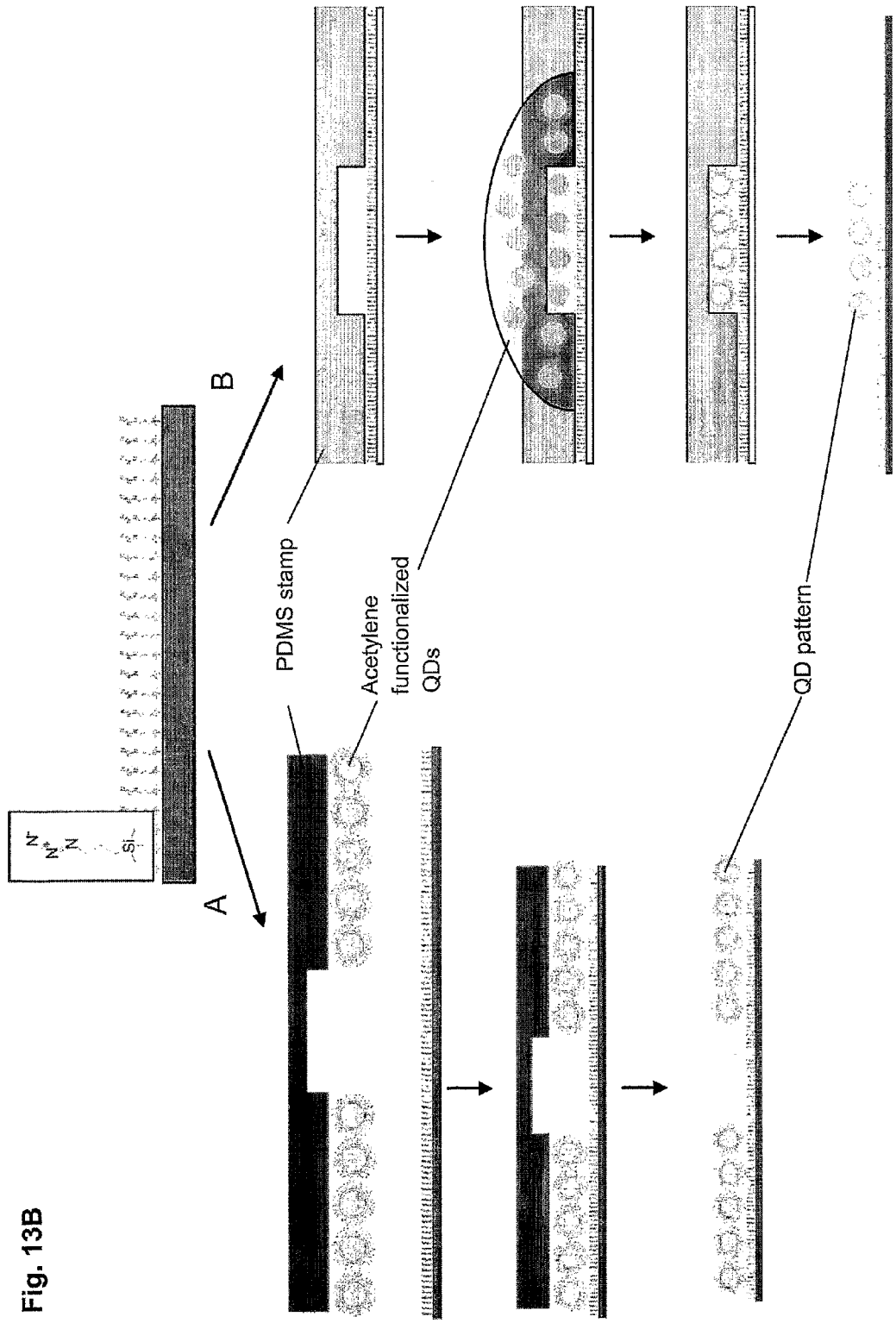
FIG. 13B shows the surface functionalization with QDs and receptors, taking advantage of "click chemistry" and layer-by-layer deposition.
Figure 15:
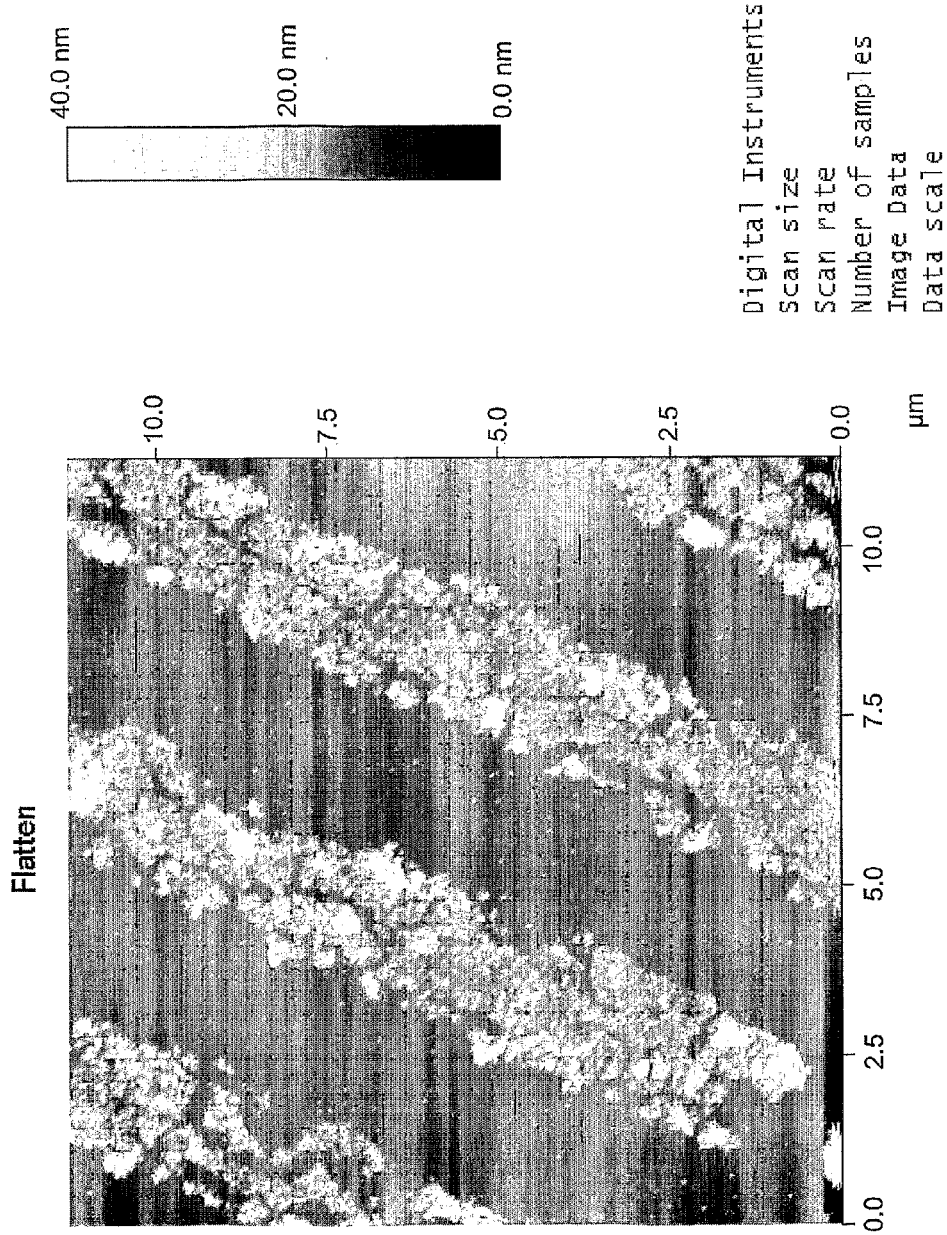
FIG. 15 depicts an Atomic Force Microscopy (AFM) image of a patterned surface of functionalized QDs on a glass substrate, obtained by immobilization of the functionalized glass substrate using click chemistry.
Figure 16A:
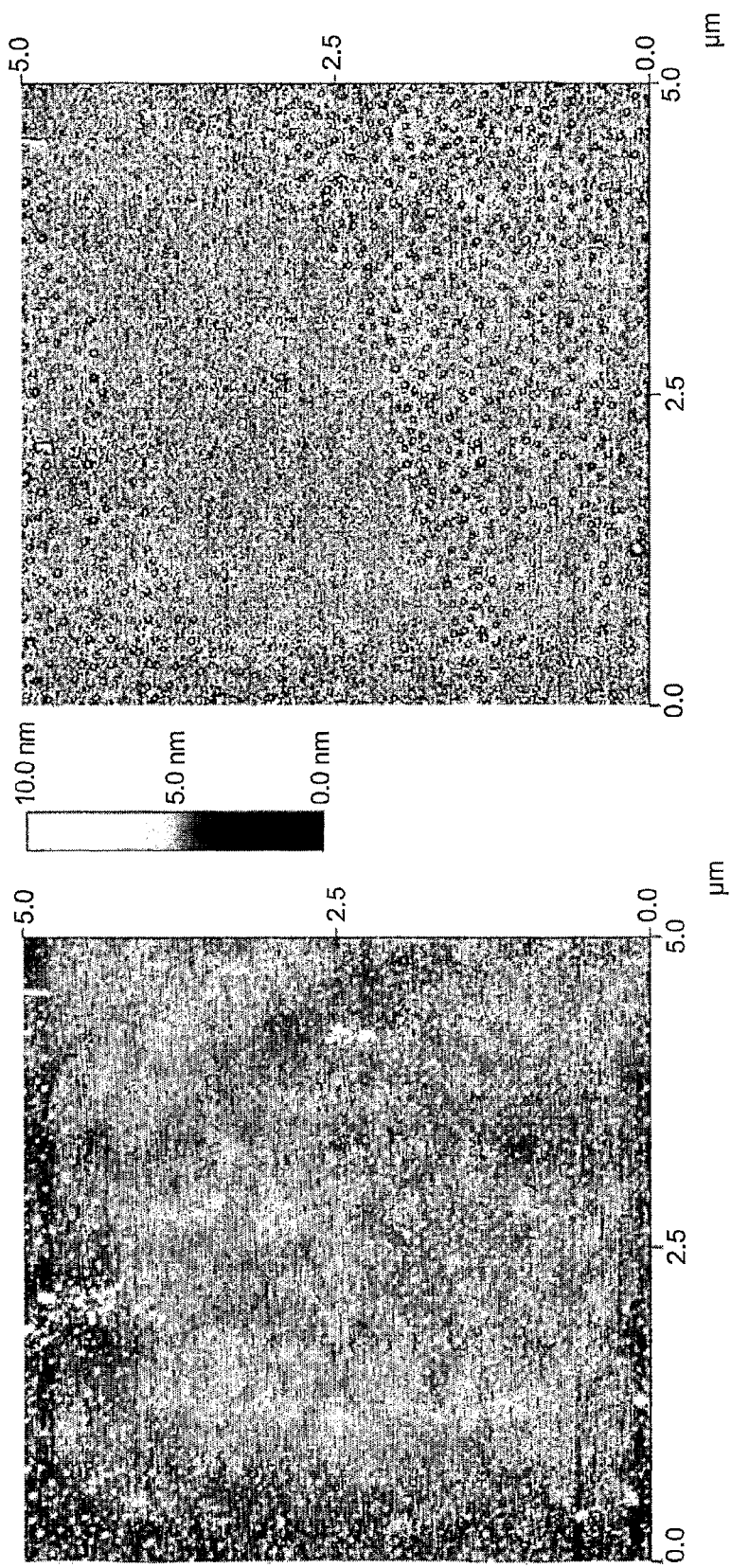
FIG. 16 depicts Atomic Force Microscopy (AFM) height (FIG. 16A) and phase (FIG. 16B) images of glass substrates patterned with functionalized QDs, obtained by immobilization of the functionalized glass substrate using click chemistry. The patterns were created using the MIMIC method. Visibly protruding spots are micelles carrying nano-particles attached to the surface using click chemistry.
Figure 16B:
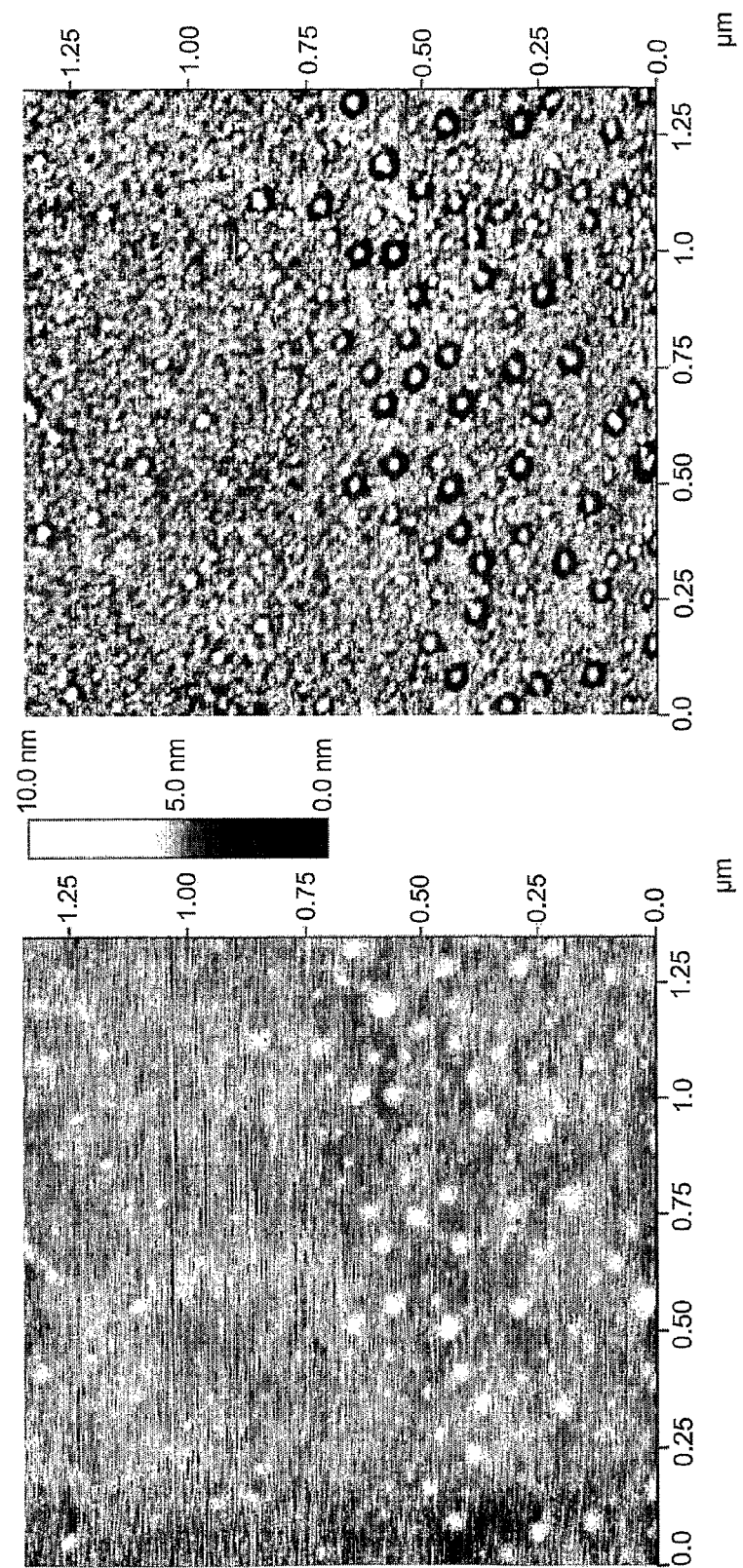

A covalent attachment of functionalized QDs can thereby be directed to obtain an arrangement in a regular fashion. The surface, e.g. a glass surface, typically carries the complementary "click chemistry" precursor. Two illustrative schematics of a corresponding process are shown in FIG. 13 and an example of such a patterned surface is illustrated in FIG. 15.

In another example layer by layer deposition of functionalized QDs onto the correspondingly functionalized surface (e.g. of glass/silicon oxide) is carried out. A recent overview of the layer-by-layer technique has been given by Ariga et al. (*Phys. Chem. Chem. Phys.* (2007) 9, 2319). After deposition, azide or acetylene functionalized receptor or capture molecules can be bound to the QDs via "click chemistry" as shown in FIG. 17. Where desired several layers of QDs can be formed on the surface before functionalization with receptor or capture molecules. The layers of QDs can be linked by a [3+2] cycloaddition reaction between alkyne and azido groups as explained above. In this case alternating layers of QDs functionalized with azido and C≡C groups, respectively, can be used. In other embodiments QDs functionalized with one such group, e.g. an azido group, may be used, in which case the layers are linked by means of a bifunctional compound having two copies of the matching group for "click chemistry", e.g. two C≡C groups. Once al layers are deposited, azide or acetylene functionalized receptor/capture molecules may be linked to the QDs. Such receptor/capture molecules include but are not limited to ionophores, peptide receptors, nucleic acid receptors and mono- and polysaccharides receptors, for example calixarenes, cavitands, porphirines, cryptands, crown ethers, cyclodextrines, peptides, polysacharides, antibodies, DNA and RNA strands, diamides, other ionophores, chromophores, conductive polymers.

In order that the invention may be readily understood and put into practical effect, particular embodiments will now be described by way of the following non-limiting examples. It is understood that modification of detail may be made without departing from the scope of the invention.

EXEMPLARY EMBODIMENTS OF THE INVENTION

As shown in FIG. 1, amphiphilic polymers have previously been synthesised by grafting n-octylamine to poly(isobutylene-alt-maleic anhydride) at different molar ratios. The grafted alkyl chains (like for example n-octylamine chain) have hydrophobic character and serve as anchoring points for attachment to the TOPO terminated quantum dot surface. Alternatively, grafting can be extended to provide different chemical functionality and function. Straightforward nucleophilic reaction was carried out in the presence of additional non nucleophilic base such as diisopropylethyl amine (DIPEA). No coupling agents were required for the grafting process.

These amphiphilic polymers can be further modified to form quantum dot-based systems for sensing schemes based on various schemes including fluorescence quenching and resonance energy transfer (FRET), where the sensing action is being triggered by external stimulus e.g. temperature, pH, presence of analyte.

The development of more sophisticated water-soluble nanoparticles or nanoparticle composites grafted with amphiphilic polymers as an enabling water-solublity shell for use in sensing or nanofabrication can be achieved with the use of coupling chemistry. The coupling chemistry has to be versatile, robust, and easy to perform, have high reaction yield and be cost-effective.

EXAMPLES

Example 1

Synthesis of Quantum Dots—General Procedure

All reagents were purchased from Aldrich or Fluka, including poly(isobutylene-alt-maleic anhydride) (Mw=6000 and 60000 g/mol). NMR spectra were recorded on a Bruker 400 MHz spectrometer. UV-VIS absorption was recorded using a Shimadzu spectrophotometer (UV-1601). A Shimadzu spectrofluorometer (RF-5301PC) was used to obtain the luminescence spectra of the quantum dot solutions.

Cadmium oxide (0.026 g, 0.20 mmol) and stearic acid (0.25 g, 0.88 mmol) were dried in vacuum and subsequently heated in $N_2$ atmosphere up to 220° C. until the solution became transparent. The mixture was cooled to room temperature and subsequently TOPO (4.00 g, 50 mmol) followed by 1-hexadecylamine (2.50 g, 500 mmol) were added. The mixture was warmed up to 220-240° C., and a solution of Se in TOP (0.2 mL, 0.2 mmol) was added. To grow a passivating ZnS layer around the CdSe core, a solution of sulphur in TOP (0.2 mL, 0.2 mmol) was added alternately with solution of $Et_2Zn$ in hexane/TOP (1 mL, 0.2 mmol) in few small portions. The size and size distribution of the nanocrystals was controlled by temperature and time between the addition of Se solution and first portion of S.

Example 2

Representative Procedure for Synthesis of an Amphiphilic Polymer Bearing The Covalently Attached Receptor—Kyptofix-22 for Metal Recognition Applications To the solution of 2.81 g poly(isobutylene-alt-maleic anhydride) (Mw=6000) in 400 mL of dry THF of 70° C. kryptofix 22 (1.45 g, 5.6 mmol) was added. 30 minutes later, n-octylamine (1.8 mL, 10.8 mmol) followed by diisopropylethyl amine (DIPEA, 1 ml) was added and the resultant mixture was stirred for 16 h at 50° C. After THF evaporation the material was suspended in water with small excess of NaOH with respect to the carboxylic groups in the polymer backbone. After evaporation of water and DIPEA, the remaining residue was dissolved in water, and dialyzed against diluted water solution of NaOH and pure water for a few days to obtain polymer in sodium salt form (yield 3.23 g; 63%).
$^1$H-NMR (400 MHz; $D_2O$) 7.22 (12 H, br) 3.62 (49 H, br), 3.25-1.60 (208 H, m), 1.47 (65 H, br), 1.24 (261 H, br), 1.14-0.65 (287 H, m). Composition: carboxylic 69.9%, octyl amide 26.1%, kryptofix-22 function 4.1%.

To identify properly the composition of the polymers obtained, NMR spectra were confronted with NMR of poly (isobutylene-alt-maleic anhydride) backbone opened by treatment with stoichiometric amount of NaOH to carboxyl groups. NMR integration was normalized to the backbone 6000 g/mol (n=38). Weight average molar mass was calculated based on the NMR spectra of purified polymers.

Example 3

Representative Procedure for Synthesis of an Amphiphilic Polymer Bearing the Covalently Attached Receptor—Cyclodextrin for Recognition of PCB Molecules To the solution of 2.00 g poly(isobutylene-alt-maleic anhydride) (Mw=6000) in 400 mL of dry THF 0.8 mL of n-octylamine (0.8 mL, 4.8 mmol) followed by DIPEA (1.7 mL, 14.4 mmol) were added and the mixture was stirred for 1 h at 50° C. Subsequently monoaminated B-cyclodextrin (0.72 g, 0.6 mmol) was added, and mixture was stirred for additional 15 h at r.t. After THF evaporation the material was suspended in water with small excess of NaOH with respect to the carboxylic groups in the polymer backbone. After evaporation of water and DIPEA, the remaining residue was dissolved in water, and dialyzed against diluted water solution of NaOH and pure water for a few days to obtain polymer in sodium salt form. Not dissolved suspension was removed from water solution by centrifugation, resulting with 2.38 g (yield 41%) of product after evaporation. $^1$H-NMR (400 MHz; D$_2$O) 7.34 (10 H, br) 5.11 (10 H, br), 4.05-3.48 (61 H, m), 3.30-1.64 (133 H, m), 1.58 (46 H, br), 1.33 (197 H, br), 1.10-0.80 (282 H, m). Composition based on functional groups: carboxylic 74.5%, octylamide 18.5%, cyclodextrine 2.5%.

Example 4

Representative Procedure for Synthesis of an Amphiphilic Polymer Bearing Acetylene Function for "Click" Attachment To the solution of 2.01 g poly(isobutylene-alt-maleic anhydride) (Mw=6000) in 400 mL of dry THF 0.8 mL of n-octylamine (0.8 mL, 4.8 mmol) followed by DIPEA (1.7 mL, 14.4 mmol) were added and the solution was warmed to 50° C. 1 h later flask was cooled to r.t. and propargyl amine was added (0.23 mL, 4.8 mmol). The mixture was stirred for 16 h. After evaporation of THF the material was suspended in water with a small excess of NaOH with respect to the carboxylic groups in the polymer backbone. After evaporation of water and DIPEA, the remaining residue was dissolved in water, and dialyzed against diluted water solution of NaOH and pure water for a few days to obtain polymer in a sodium salt form (yield 1.76 g; 53%). $^1$H-NMR (400 MHz; D$_2$O) 7.21 (9 H, br) 3.93-3.72 (33 H, br), 3.20-1.63 (205 H, m), 1.46 (70 H, br), 1.22 (215 H, br), 1.08-0.65 (279 H, m). Composition: carboxylic 56%, octylamide 22.5%, propargyl amide 21.6%.

Example 5

Representative Procedure for Synthesis of an Amphiphilic Polymer Bearing Azide Functionalized Peg Side Chain for "Click" Attachment To the solution of 2.00 g poly(isobutylene-alt-maleic anhydride) (Mw=6000) in 400 mL of dry THF 0.8 mL of n-octylamine (0.8 mL, 4.8 mmol) followed by DIPEA (1.7 mL, 14.4 mmol) were added and the solution was warmed to 50° C. 1 h later the flask was cooled to r.t. and 11-azido-3,6,9-trioxaunadecan was added (0.9 mL, 4.8 mmol). The mixture was stirred for 16 h. After evaporation of THF the material was suspended in water with a small excess of NaOH with respect to the carboxylic groups in the polymer backbone. After evaporation of water and DIPEA, the remaining residue was dissolved in water, and dialyzed against diluted water solution of NaOH and pure water for a few days to obtain the polymer in a sodium salt form (yield 3.07 g; 58%). $^1$H-NMR (400 MHz; D$_2$O) 7.21 (11 H, br) 3.77-3.65 (198 H, m), 3.35-1.61 (291 H, m), 1.47 (55 H, br), 1.22 (186 H, br), 1.12-0.65 (274 H, m). Composition: carboxylic 61.3%, octyl amide 20.3%, azide-PEG side chain 18.3%.

Example 6

Synthesis of Quantum Dot/Polymer Assemblies 2 mg of purified quantum dots were dissolved in THF (2 mL) and 0.5 mL of 1.4 mM polymer solution was added followed by 5 mL of water. The mixture was concentrated with a rotary evaporator to 1 mL. Turbid water suspension was filtered through a 0.8 μm filter and the filter was washed with 5 mL of pure water. The supernatant was filtered again according to the same procedure through a hydrophilic filter (0.2 μm) resulting in a clear quantum dot water solution. Excess of water can be removed with a rotary evaporator to reach desirable concentration.

Based on the absorption of quantum dot/polymer assemblies it is estimated that from 10 to 80% of dots is passing the suspension procedure. This yield is however strongly dependent on polymer used and even more dependent on the purity of the quantum dots (excess of hydrophobic ligands lead to formation of aggregates).

Example 7

Preparation of Azide Functionalized Glass/Silicon Oxide Substrate (Glass Slaid Surface) for "Click" Patterning A Glass/Silicon wafer was heated in a furnace (350° C., 5 h) to oxidize and clean its surface. The substrate, cooled to r.t., was subsequently exposed to (3-Bromopropyl)tri-chlorosilane in vacuum for 16 h to deposit a layer of bromosilanes on the surface. Exchange of Br-functionality to azide was carried by immersing of substrate into a warm bath (50° C.) of DMF saturated with sodium azide for 16 h. Washing of the substrate with water and ethanol resulted in a surface ready for "click" chemistry.

Example 8

Patterning of Azide Terminated Glass Substrate Using "Click Chemistry"

An aqueous solution of quantum dots coated with a polymer prepared according to the procedure described in Example 4 (5% of quantum dot assemblies, 1% of Cu(I) Acetate) was drop-casted on a glass slide surface prepared according to the procedure described in example 7. After 10 minutes, the surface was washed with water and ethanol leaving a layer of quantum dot assemblies covalently attached to the surface.

Example 9

Patterning of Azide Terminated Glass Substrate Using "Click Chemistry"—PDMS Stamp Patterning An aqueous solution of quantum dots coated with the polymer prepared according to the procedure described in Example 4 (5% of quantum dot assemblies, 1% of Cu(I) Acetate) was transferred on a glass slide surface prepared according to Example 6 using PDMS stamp. After 1 hour, the surface was washed with water and ethanol leaving a layer of quantum dot assemblies covalently attached to the surface in form of pattern.

Example 10

Patterning of Azide Terminated Glass Substrate Using "Click Chemistry"—MIMIC Technique A dry glass slide prepared according to Example 6 was covered with a PDMS stamp. Subsequently, an aqueous solution of quantum dots coated with the polymer prepared according to the procedure described in the example 4 (5% of quantum dot assemblies, 1% of Cu(I)Acetate) was deposited on the side of the stamp allowing the liquid to be sucked into the patterns by capillary forces. After 1 hour the surface was washed with water and ethanol leaving a layer of quantum dot assemblies covalently attached to the surface in form of a pattern.

One skilled in the art would readily appreciate that the present invention is well adapted to carry out the objects and obtain the ends and advantages mentioned, as well as those inherent therein. Further, it will be readily apparent to one skilled in the art that varying substitutions and modifications may be made to the invention disclosed herein without departing from the scope and spirit of the invention. The compositions, methods, procedures, treatments, molecules and specific compounds described herein are presently representative of preferred embodiments are exemplary and are not intended as limitations on the scope of the invention. Changes therein and other uses will occur to those skilled in the art which are encompassed within the spirit of the invention are defined by the scope of the claims. The listing or discussion of a previously published document in this specification should not necessarily be taken as an acknowledgement that the document is part of the state of the art or is common general knowledge.

The inventions illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed is:

1. An amphiphilic polymer (A) comprising repeat units of the general formulae (I), (II) and (III):

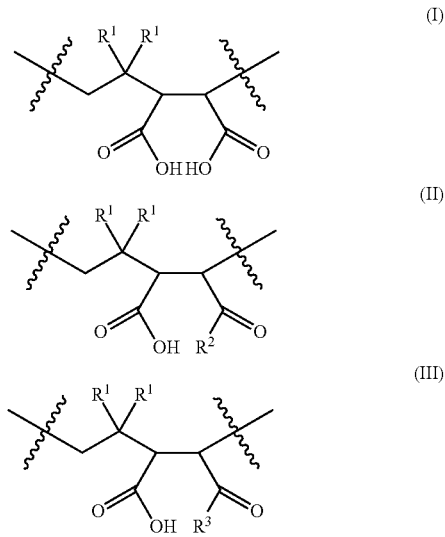

or salts thereof, wherein the repeat unit of general formula (I) is comprised in the amphiphilic polymer with a number of m units, the repeat unit of general formula (II) is comprised in the amphiphilic polymer with a number of o units and repeat unit of general formula (III) is comprised in the amphiphilic polymer with a number of p units, wherein each of m, o and p is an independently selected integer from about 3 to about 400 and wherein the sum of m+o+p is selected in the range from about 10 to about 10000, $R^1$ in repeat units (I)-(III) is H or methyl, $R^2$ in repeat unit (II) is an aliphatic moiety with a main chain of about 3 to about 30 carbon atoms and 0 to about 3 heteroatoms selected from the group N, O, S, Se and Si, and, $R^3$ in repeat unit (III) is one of (i) an alicyclic moiety with a main chain of about 5 to about 80 carbon atoms and 0 to about 30 heteroatoms selected from the group N, O, S, Se and Si, and, (ii) a moiety —Z—$R^4$ wherein $R^4$ is an alicyclic moiety with a main chain of about 5 to about 80 carbon atoms and 0 to about 30 heteroatoms selected from the group N, O, S, Se and Si and Z is an aliphatic bridge of 1 to 3 carbon atoms and 0 to about 2 heteroatoms selected from group of N, O, S, Se and Si, (iii) an aliphatic moiety with a main chain of about 3 to about 80 carbon atoms and 0 to about 30 heteroatoms selected from the group N, O, S, Se and Si, and a C≡C group or an azido group.

2. The amphiphilic polymer of claim 1, wherein the ratio of the repeat unit of general formula (I) to the repeat units of general formulae (II) and (III) m/(o+p) is selected in the range from 0 to about 20.

3. The amphiphilic polymer of claim 1, wherein $R^3$ in repeat unit (III) is a moiety —Z—$R^4$ and wherein the alicyclic moiety $R^4$ is selected from an ionophore, a peptide, a nucleic acid, a monosaccharide, a polysaccharide, a glycolamide, a calixarene, a cavitand, a cryptand, a crown ether, a porphyrin, a cyclodextrin and a chromophore.

4. An amphiphilic polymer (A) comprising repeat units of the general formulae (I), (II) and (III):

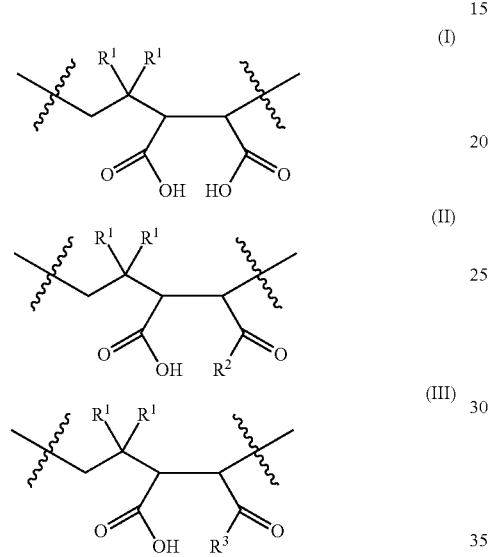

or salts thereof, wherein the repeat unit of general formula (I) is comprised in the amphiphilic polymer with a number of m units, the repeat unit of general formula (II) is comprised in the amphiphilic polymer with a number of o units and repeat unit of general formula (III) is comprised in the amphiphilic polymer with a number of p units, wherein each of m, o and p is an independently selected integer from about 3 to about 400 and wherein the sum of m+o+p is selected in the range from about 10 to about 10000, $R^1$ in repeat units (I)-(III) is H or methyl, $R^2$ in repeat unit (II) is an aliphatic moiety with a main chain of about 3 to about 30 carbon atoms and 0 to about 3 heteroatoms selected from the group N, O, S, Se and Si, and, $R^3$ in repeat unit (III) is one of (i) an alicyclic moiety with a main chain of about 5 to about 80 carbon atoms and 0 to about 30 heteroatoms selected from the group N, O, S, Se and Si, and, (ii) a moiety —Z—$R^4$ wherein $R^4$ is an alicyclic moiety with a main chain of about 5 to about 80 carbon atoms and 0 to about 30 heteroatoms selected from the group N, O, S, Se and Si and Z is an aliphatic bridge of 1 to about 3 carbon atoms and 0 to about 2 heteroatoms selected from the group N, O, S, Se and Si, (iii) an aliphatic moiety with a main chain of about 3 to about 80 carbon atoms and 0 to about 30 heteroatoms selected from the group N, O, S, Se and Si, and a C≡C group or an azido group, wherein $R^3$ in repeat unit (III) is a moiety —Z—$R^4$ and wherein Z is aminoethyl.

5. The amphiphilic polymer of claim 1, wherein $R^2$ in repeat unit (II) is an alkylamino group.

6. An amphiphilic polymer (A) comprising repeat units of the general formulae (I), (II) and (III):

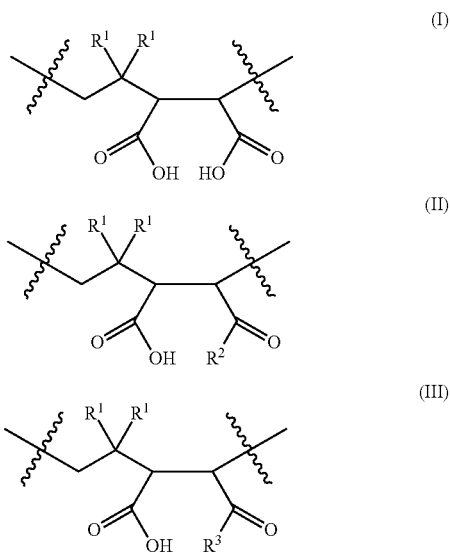

or salts thereof, wherein the repeat unit of general formula (I) is comprised in the amphiphilic polymer with a number of m units, the repeat unit of general formula (II) is comprised in the amphiphilic polymer with a number of o units and repeat unit of general formula (III) is comprised in the amphiphilic polymer with a number of p units, wherein each of m, o and p is an independently selected integer from about 3 to about 400 and wherein the sum of m+o +p is selected in the range from about 10 to about 10000, $R^1$ in repeat units (I)-(III) is H or methyl, $R^2$ in repeat unit (II) is an aliphatic moiety with a main chain of about 3 to about 30 carbon atoms and 0 to about 3 heteroatoms selected from the group N, O, S, Se and Si, and, $R^3$ in repeat unit (III) is one of (i) an alicyclic moiety with a main chain of about 5 to about 80 carbon atoms and 0 to about 30 heteroatoms selected from the group N, O, S, Se and Si, and, (ii) a moiety —Z—$R^4$ wherein $R^4$ is an alicyclic moiety with a main chain of about 5 to about 80 carbon atoms and 0 to about 30 heteroatoms selected from the group N, O, S, Se and Si and Z is an aliphatic bridge of 1 to about 3 carbon atoms and 0 to about 2 heteroatoms selected from the group N, O, S, Se and Si, (iii) an aliphatic moiety with a main chain of about 3 to about 80 carbon atoms and 0 to about 30 heteroatoms selected from the group N, O, S, Se and Si, and a C≡C group or an azido group, wherein the amphiphilic polymer further comprises a repeat unit of the general formula (IV), thereby defining an amphiphilic polymer (B):

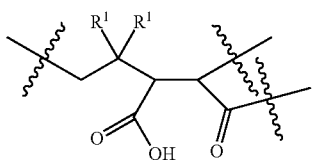
(IV)

wherein $R^1$ is H or methyl, the repeat unit of general formula (IV) being comprised in the amphiphilic polymer with a number of r units, wherein r is an independently selected integer from 1 to about 400, wherein the sum of p+r is selected in the range from about 3 to about 400, wherein the unit (IV) of the polymer is covalently coupled to one of a surface, a further polymer and a sensing molecule via a bridge comprising an aliphatic moiety with a main chain of about 3 to about 80 carbon atoms and 0 to about 20 heteroatoms selected from the group N, O, S, Se and Si, and a triazole ring, wherein the bridge is obtained by a reaction involving the C≡C group or the azido group of the aliphatic moiety $R^3$ and a C≡C group or an azido group on the surface, the further polymer or the sensing molecule.

7. The amphiphilic polymer of claim 6, wherein the sensing molecule is one of a peptide, a protein, a nucleic acid, a saccharide, a polysaccharide, and a lipid.

8. The amphiphilic polymer of claim 6, wherein the surface is one of a metal surface, a metalloid surface, a surface of a cell, and a surface of a virus particle.

9. The amphiphilic polymer of claim 6, wherein the further polymer coupled to the amphiphilic polymer (B) is an amphiphilic polymer (B'), wherein the amphiphilic polymer (B') comprises repeat units of the general formulae (I), (II), (III) and (IV):

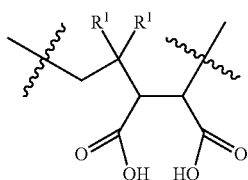
(I)

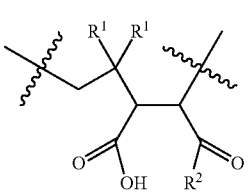
(II)

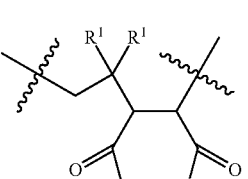
(III)

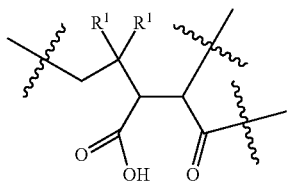
(IV)

or salts thereof, wherein the repeat units of general formulae (I), (II), (III) and (IV) are independently selected from the repeat units of general formulae (I), (II), (III) and (IV) of the amphiphilic polymer (B), the repeat unit of general formula (I) being comprised in the amphiphilic polymer with a number of m units, the repeat unit of general formula (II) being comprised in the amphiphilic polymer with a number of o units, and repeat unit of general formula (III) being comprised in the amphiphilic polymer with a number of p units, the repeat unit of general formula (IV) being comprised in the amphiphilic polymer with a number of r units, wherein each of m, o and p is an independently selected integer from about 3 to about 400, r is an independently selected integer from 1 to about 400, the sum of p+r is selected in the range from about 3 to about 400, the sum of m+o+p+r is selected in the range from about 10 to about 10000, $R^1$ in repeat units (I)-(IV) is H or methyl, $R^2$ in repeat unit (II) is an aliphatic moiety with a main chain of about 3 to about 30 carbon atoms and 0 to about 3 heteroatoms selected from the group N, O, S, Se and Si, and, $R^3$ in repeat unit (III) is one of (i) an alicyclic moiety with a main chain of about 5 to about 80 carbon atoms and 0 to about 30 heteroatoms selected from the group N, O, S, Se and Si, and, (ii) a moiety —Z—$R^4$ wherein $R^4$ is an alicyclic moiety with a main chain of about 5 to about 80 carbon atoms and 0 to about 30 heteroatoms selected from the group N, O, S, Se and Si, and Z is an aliphatic bridge of 1 to about 3 carbon atoms and 0 to about 2 heteroatoms selected from the group N, O, S, Se and Si, (iii) an aliphatic moiety with a main chain of about 3 to about 80 carbon atoms and 0 to about 30 heteroatoms selected from the group N, O, S, Se and Si, and a C≡C group or an azido group, wherein the unit (IV) of the amphiphilic polymer (B') is covalently coupled to the amphiphilic polymer (B) via the bridge.

10. The amphiphilic polymer of claim 6, wherein the bridge is represented by the formula

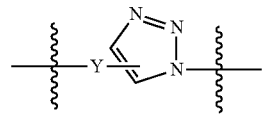

wherein Y is an aliphatic moiety with a main chain of 1 to about 80 carbon atoms and 0 to about 20 heteroatoms selected from the group N, O, S, Se and Si.

11. A water-soluble nanocrystal, the water-soluble nanocrystal comprising on its surface via non-covalent or covalent interaction an amphiphilic polymer according to claim 1.

12. A plurality of water-soluble nanocrystals, the nanocrystals of the plurality of nanocrystals comprising on their surface via non-covalent or covalent interaction an amphiphilic polymer (B), wherein the amphiphilic polymer (B) comprises repeat units of the general formulae (I), (II), (III) and (IV):

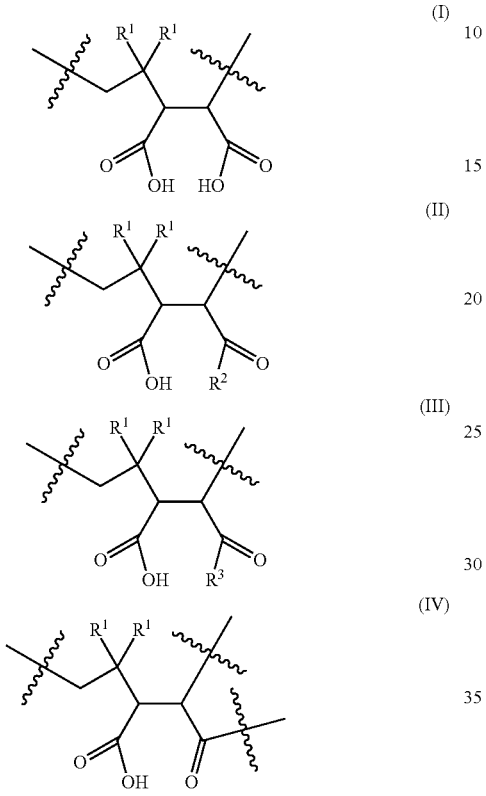

or salts thereof,
wherein the repeat unit of general formula (I) is comprised in the amphiphilic polymer with a number of m units, the repeat unit of general formula (II) is comprised in the amphiphilic polymer with a number of o units, the repeat unit of general formula (III) is comprised in the amphiphilic polymer with a number of p units and the repeat unit of general formula (IV) is comprised in the amphiphilic polymer with a number of q units,
wherein each of m, o and p are an independently selected integer from about 3 to about 400,
q is an independently selected even integer from 1 to about 400,
wherein the sum of p+q is selected in the range from about 3 to about 400,
and wherein the sum of m+o+p+q is selected in the range from about 10 to about 10000,
$R^1$ in repeat units (I)-(IV) is H or methyl,
$R^2$ in repeat unit (II) is an aliphatic moiety with a main chain of about 3 to about 30 carbon atoms and 0 to about 3 heteroatoms selected from the group N, O, S, Se and Si,
$R^3$ in repeat unit (III) is an aliphatic moiety with a main chain of about 3 to about 80 carbon atoms and a C≡C group or an azido group,
wherein a first water-soluble nanocrystal and a second water-soluble nanocrystal of the plurality of nanocrystals are coupled via a bridge D, the bridge D being covalently bonded to a unit (IV) of a first nanocrystal and a unit (IV) of a second nanocrystal,
the bridge D being of the structure —Y—$R^5$—Y—, wherein $R^5$ is an arylaliphatic or arylalicyclic bridge comprising a triazole ring, and Y is an aliphatic bridge of 1 to about 80 carbon atoms and 0 to about 20 heteroatoms selected from the group N, O, S, Se and Si,
wherein the bridge D is obtained by a reaction involving the C≡C group or the azido group of the aliphatic moiety $R^3$ of the amphiphilic polymer (B) on the first water-soluble nanocrystal and a C≡C group or an azido group of the amphiphilic polymer (B) on the second water-soluble nanocrystal.

13. A plurality of water-soluble nanocrystals immobilized on a surface, the nanocrystals of the plurality of nanocrystals comprising on their surface via non-covalent or covalent interaction an amphiphilic polymer (B), the amphiphilic polymer (B) comprising repeat units of the general formulae (I), (II), (III) and (IV):

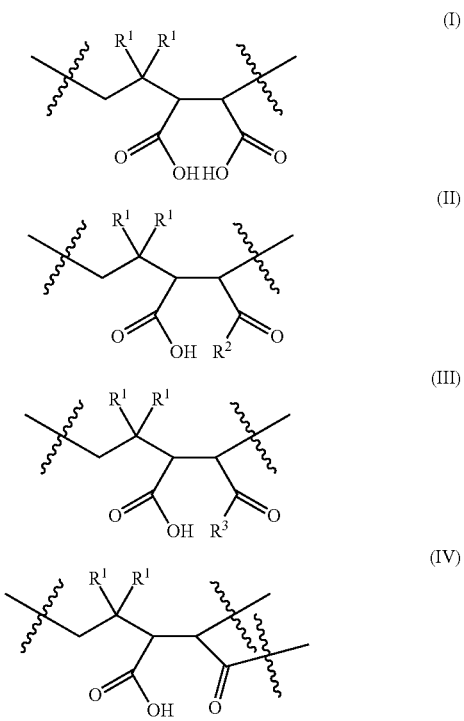

or salts thereof,
wherein the repeat unit of general formula (I) is comprised in the amphiphilic polymer with a number of m units, the repeat unit of general formula (II) is comprised in the amphiphilic polymer with a number of o units, the repeat unit of general formula (III) is comprised in the amphiphilic polymer with a number of p units and the repeat unit of general formula (IV) is comprised in the amphiphilic polymer with a number of r units,
each of m, o and p are an independently selected integer from about 3 to about 400,
wherein the sum of p+r is selected in the range from about 3 to about 400, and
the sum of m+o+p+r is selected in the range from about 10 to about 10000,
wherein $R^1$ in repeat units (I)-(IV) is H or methyl, $R^2$ in repeat unit (II) is an aliphatic moiety with a main chain of about 3 to about 30 carbon atoms and 0 to about 3 heteroatoms selected from the group N, O, S, Se and Si, $R^3$ in repeat unit (III) is an aliphatic moiety with a main chain of about 3 to about 80 carbon atoms and a C≡C group or an azido group, wherein the nanocrystals of the plurality of nanocrystals are coupled to the surface via a bridge D, the bridge D being covalently bonded to a unit (IV) of a nanocrystal and to the surface, wherein the bridge D is of the structure —$G^1$—$R^5$—$G^2$—, wherein $G^1$ and $G^2$ are independent from one another an aliphatic bridge of 1 to about 80 carbon atoms and 0 to about 20 heteroatoms selected from the group N, O, S, Se and Si, and $R^5$ is an arylaliphatic or arylalicyclic bridge comprising a triazole ring, wherein the bridge D is obtained by a reaction involving the C≡C group or the azido group of the aliphatic moiety $R^3$ and a C≡C group or an azido group on the surface.

14. A process of forming an amphiphilic polymer (A), the amphiphilic polymer comprising repeat units of the general formulae (I), (II) and (III):

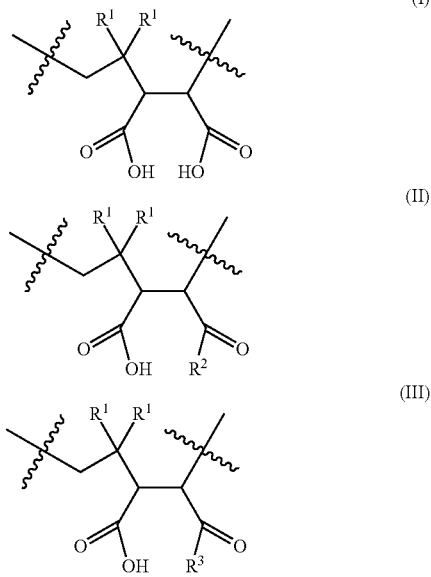

or salts thereof, wherein the repeat unit of general formula (I) is comprised in the amphiphilic polymer with a number of m units, the repeat unit of general formula (II) is comprised in the amphiphilic polymer with a number of o units and repeat unit of general formula (III) is comprised in the amphiphilic polymer with a number of p units, wherein each of m, o and p is an independently selected integer from about 3 to about 400 and wherein the sum of m+o+p is selected in the range from about 10 to about 10000, $R^1$ in repeat units (I)-(III) is H or methyl, $R^2$ in repeat unit (II) is an aliphatic moiety with a main chain of about 3 to about 30 carbon atoms and 0 to about 3 heteroatoms selected from the group N, O, S, Se and Si, and, $R^3$ in repeat unit (III) is one of (i) an alicyclic moiety with a main chain of about 5 to about 80 carbon atoms and 0 to about 30 heteroatoms selected from the group N, O, S, Se and Si, (ii) a moiety —Z—$R^4$ wherein $R^4$ is an alicyclic moiety with a main chain of about 5 to about 80 carbon atoms and 0 to about 30 heteroatoms selected from the group N, O, S, Se and Si, and Z is an aliphatic bridge of 1 to 3 carbon atoms and 0 to about 2 heteroatoms selected from group of N, O, S, Se and Si, (iii) an aliphatic moiety with a main chain of about 3 to about 80 carbon atoms and 0 to about 20 heteroatoms selected from the group N, O, S, Se and Si, and a C≡C group or an azido group, the process comprising reacting in a suitable solvent a maleic anhydride polymer of formula (V),

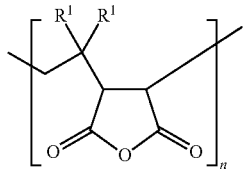

wherein n is an integer from about 10 to about 10000, and R1 is H or methyl, with:
a first compound, the first compound being a monofunctional aliphatic compound carrying a functional group capable of forming a linkage with an anhydride, wherein the aliphatic compound has an alkyl chain of about 3 to about 30 carbon atoms and 0 to about 2 heteroatoms selected from the group N, O, S, Se and Si; and a second compound, the second compound being an alicyclic or aliphatic compound carrying a functional group capable of forming a linkage with an anhydride, wherein the alicyclic compound has a main chain of about 5 to about 80 carbon atoms and 0 to about 30 heteroatoms selected from the group N, O, S, Se and Si, and wherein the aliphatic compound (i) is an aliphatic bridge of 1 to about 3 carbon atoms and 0 to about 2 heteroatoms selected from the group N, O, S, Se and Si, substituted with an alicyclic moiety $R^4$, wherein $R^4$ is an alicyclic moiety with a main chain of about 5 to about 80 carbon atoms and 0 to about 30 heteroatoms selected from the group N, O, S, Se and Si, or (ii) has a main chain of about 3 to about 80 carbon atoms and 0 to about 20 heteroatoms selected from the group N, O, S, Se and Si, and additionally a C≡C group or an azido group.

15. The process of claim 14, wherein the functional groups capable of forming a linkage with an anhydride of the first compound and of the second compound are independently one of an amino group, a hydroxyl group, a thiol group, a selenol group, a halogen, an ether group and a thioether group.

16. The process of claim 14, wherein the second compound is an alkylamine.

17. The process of claim 14, wherein the amphiphilic polymer (A) is formed using a first compound that is an aliphatic compound having a main chain of about 3 to about 80 carbon atoms and 0 to about 20 heteroatoms selected from the group N, O, S, Se and Si, the aliphatic compound having a C≡C group in addition to the functional group capable of forming a linkage with an anhydride, the process further comprising reacting the amphiphilic polymer (A) with a compound or a surface, wherein the compound or the surface carries an azido group, thereby allowing the formation of a bridge between the amphiphilic polymer (A) and the compound or the surface, the bridge comprising a triazole ring.

18. The process of claim 17, wherein the compound or surface reacted with the amphiphilic polymer (A) is an amphiphilic polymer (A') comprising repeat units of the general formulae (I), (II) and (III):

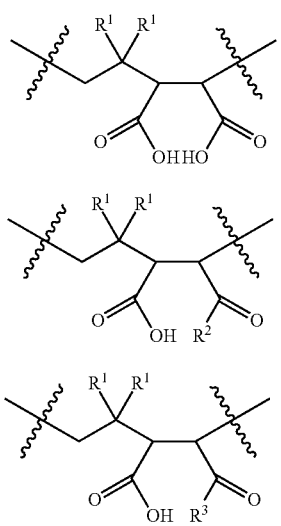

or salts thereof, wherein the repeat unit of general formula (I) is comprised in the amphiphilic polymer with a number of m units, the repeat unit of general formula (II) is comprised in the amphiphilic polymer with a number of o units and repeat unit of general formula (III) is comprised in the amphiphilic polymer with a number of p units, wherein each of m, o and p is an independently selected integer from about 3 to about 400 and wherein the sum of m+o+p is selected in the range from about 10 to about 10000, $R^1$ in repeat units (I)-(III) is H or methyl, $R^2$ in repeat unit (II) is an aliphatic moiety with a main chain of about 3 to about 30 carbon atoms and 0 to about 3 heteroatoms selected from the group N, O, S, Se and Si, and, $R^3$ in repeat unit (III) is one of (i) an alicyclic moiety with a main chain of about 5 to about 80 carbon atoms and 0 to about 30 heteroatoms selected from the group N, O, S, Se and Si, (ii) a moiety —Z—$R^4$ wherein $R^4$ is an alicyclic moiety with a main chain of about 5 to about 80 carbon atoms and 0 to about 30 heteroatoms selected from the group N, O, S, Se and Si, and Z is an aliphatic bridge of 1 to 3 carbon atoms and 0 to about 2 heteroatoms selected from group of N, O, S, Se and Si (iii) an aliphatic moiety with a main chain of about 3 to about 80 carbon atoms and 0 to about 20 heteroatoms selected from the group N, O, S, Se and Si, and a C≡C group or an azido group, and wherein A' is obtained by the process comprising reacting in a suitable solvent a maleic anhydride polymer of formula (V),

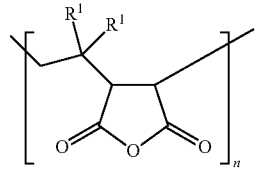

wherein n is an integer from about 10 to about 10000, and R1 is H or methyl, with:
a first compound, the first compound being an aliphatic compound having a main chain of about 3 to about 80 carbon atoms and 0 to about 20 heteroatoms selected from the group N, O, S, Se and Si, the aliphatic compound having an azido group in addition to the functional group capable of forming a linkage with an anhydride; and a second compound, the second compound being an alicyclic or aliphatic compound carrying a functional group capable of forming a linkage with an anhydride, wherein the alicyclic compound has a main chain of about 5 to about 80 carbon atoms and 0 to about 30 heteroatoms selected from the group N, O, S, Se and Si, and wherein the aliphatic compound (i) is an aliphatic bridge of 1 to about 3 carbon atoms and 0 to about 2 heteroatoms selected from the group N, O, S, Se and Si, substituted with an alicyclic moiety $R^4$, wherein $R^4$ is an alicyclic moiety with a main chain of about 5 to about 80 carbon atoms and 0 to about 30 heteroatoms selected from the group N, O, S, Se and Si, or (ii) has a main chain of about 3 to about 80 carbon atoms and 0 to about 20 heteroatoms selected from the group N, O, S, Se and Si, and additionally a C≡C group or an azido group.

19. The process of claim 14, wherein the amphiphilic polymer (A) is formed using a first compound that is an aliphatic compound having a main chain of about 3 to about 80 carbon atoms and 0 to about 20 heteroatoms selected from the group N, O, S, Se and Si, the aliphatic compound having an azido group in addition to the functional group capable of forming a linkage with an anhydride, the process further comprising reacting the amphiphilic polymer (A) with a compound or a surface, wherein the compound or the surface carries a C≡C group, thereby allowing the formation of a bridge between the amphiphilic polymer (A) and the compound or the surface, the bridge comprising a triazole ring.

20. A method of forming a water-soluble nanocrystal, the method comprising:
(i) providing a nanocrystal in a suitable solvent,
(ii) contacting the nanocrystal with an amphiphilic polymer (A) according to claim 1, and
(iii) allowing non-covalent or covalent interaction between the amphiphilic polymer and the nanocrystal to occur, thereby forming a water-soluble nanocrystal.

21. The method of claim 20, wherein the provided nanocrystal comprises a semiconducting material.

22. The method of claim 20, wherein the amphiphilic polymer has repeat units (III) with $R^3$ being an aliphatic moiety with a main chain of about 3 to about 80 carbon atoms and 0 to about 20 heteroatoms selected from the group N, O, S, Se and Si, and a C≡C group or an azido group, the method further comprising contacting the amphiphilic polymer (A) with a compound or with a surface, wherein the compound or the surface carries an azido group or a C≡C group, thereby allowing a reaction to occur, the reaction involving the C≡C group or the azido group of the aliphatic moiety $R^3$ of the amphiphilic polymer (B) on the water-soluble nanocrystal and a C≡C group or an azido group of the compound or on the surface, thereby allowing the formation of a bridge between the amphiphilic polymer (A) and the compound or the surface, the bridge comprising a triazole ring.

23. The method of claim 22, wherein (i) the compound or the surface carries an azido group, and the aliphatic moiety $R^3$ of the polymer (B) on the nanocrystal carries a C≡C group or (ii) the compound or the surface carries a C≡C group, and the aliphatic moiety $R^3$ of the polymer (B) on the nanocrystal carries an azido group, and wherein the reaction is a reaction between the C≡C group or the azido group of the compound or on the surface, and the azido group or the C≡C group, respectively of the aliphatic moiety $R^3$ of the polymer (B) on the nanocrystal.

* * * * *

UNITED STATES PATENT AND TRADEMARK OFFICE
CERTIFICATE OF CORRECTION

| | |
|---|---|
| PATENT NO. | : 8,716,420 B2 |
| APPLICATION NO. | : 13/124113 |
| DATED | : May 6, 2014 |
| INVENTOR(S) | : Dominik Janczewski |

Page 1 of 1

It is certified that error appears in the above-identified patent and that said Letters Patent is hereby corrected as shown below:

In the Specification

Column 27, line 67 "... that furthermore bi-, and higher ..."
　　should be --... that furthermore bi-, tri- and higher ...--.

Column 28, line 26, "... thus the functional groups) ..."
　　should be --... thus the functional group(s) ...--.

Column 36, line 26-27, "... 17, 18, 19, or heteroatoms ..."
　　should be --... 17, 18, 19, or 20 heteroatoms ...--.

Signed and Sealed this
Nineteenth Day of August, 2014

Michelle K. Lee
*Deputy Director of the United States Patent and Trademark Office*